(12) United States Patent
Sanders et al.

(10) Patent No.: US 12,178,710 B2
(45) Date of Patent: Dec. 31, 2024

(54) FLEXIBLE INTERBODY SPACER AND METHODS FOR USE

(71) Applicant: REVIVO MEDICAL, LLC, Loudonville, NY (US)

(72) Inventors: Glenn Patrick Sanders, Troy, NY (US); Eric Howard Ledet, Schenectady, NY (US)

(73) Assignee: REVIVO MEDICAL, LLC, Loudonville, NY (US)

( * ) Notice: Subject to any disclaimer, the term of this patent is extended or adjusted under 35 U.S.C. 154(b) by 28 days.

(21) Appl. No.: 18/055,668

(22) Filed: Nov. 15, 2022

(65) Prior Publication Data

US 2023/0190487 A1 Jun. 22, 2023

Related U.S. Application Data

(63) Continuation of application No. 17/301,157, filed on Mar. 26, 2021, now Pat. No. 11,497,614, which is a continuation of application No. PCT/US2019/053276, filed on Sep. 26, 2019.

(60) Provisional application No. 62/737,095, filed on Sep. 26, 2018.

(51) Int. Cl.
*A61F 2/44* (2006.01)
*A61F 2/28* (2006.01)

(52) U.S. Cl.
CPC ...... *A61F 2/442* (2013.01); *A61F 2002/2835* (2013.01)

(58) Field of Classification Search
USPC .......................................... 623/17.11–17.16
See application file for complete search history.

(56) References Cited

U.S. PATENT DOCUMENTS

| 5,192,327 | A | 3/1993 | Brantigan |
|---|---|---|---|
| 6,106,557 | A | 8/2000 | Robioneck |
| 6,315,797 | B1 | 11/2001 | Middleton |
| 7,578,849 | B2 | 8/2009 | Trieu |
| 8,092,533 | B2 | 1/2012 | Melkent |
| 8,236,055 | B2 | 8/2012 | Cordaro |
| 8,753,399 | B2 | 6/2014 | Sharifi-Mehr |
| 2004/0220580 | A1 | 11/2004 | Johnson |
| 2005/0060034 | A1 | 3/2005 | Berry |
| 2005/0149194 | A1 | 7/2005 | Ahlgren |
| 2005/0234553 | A1 | 10/2005 | Gordon |
| 2006/0030943 | A1 | 2/2006 | Peterman |
| 2006/0200241 | A1 | 9/2006 | Rothman |
| 2009/0118836 | A1 | 5/2009 | Cordaro |
| 2010/0004748 | A1 | 1/2010 | Cordaro |
| 2010/0152856 | A1 | 6/2010 | Overes |

(Continued)

FOREIGN PATENT DOCUMENTS

| CN | 202458786 | 10/2012 |
|---|---|---|
| CN | 103300949 | 9/2013 |

(Continued)

*Primary Examiner* — Eduardo C Robert
*Assistant Examiner* — Christina Negrellirodriguez
(74) *Attorney, Agent, or Firm* — Heslin Rothenberg Farley & Mesiti P.C.; Jacquelyn A. Graff, Esq.

(57) ABSTRACT

The present disclosure includes implant systems, devices, and implants. The interbody spacers including a first endplate, a second endplate, and a coupling member coupled to and extending between the first endplate and the second endplate. Methods of using the interbody spacers are also disclosed.

19 Claims, 39 Drawing Sheets

(56) References Cited

U.S. PATENT DOCUMENTS

| | | |
|---|---|---|
| 2011/0029087 A1 | 2/2011 | Haider |
| 2011/0093075 A1* | 4/2011 | Duplessis ............. A61F 2/4425 623/17.16 |
| 2011/0125270 A1 | 5/2011 | Paul |
| 2012/0109305 A1 | 5/2012 | Park |
| 2012/0277748 A1* | 11/2012 | Trescony ............... A61B 17/80 606/70 |
| 2014/0018924 A1 | 1/2014 | McManus et al. |
| 2014/0257395 A1* | 9/2014 | Ledet ................. A61B 17/7029 606/279 |
| 2016/0022432 A1 | 1/2016 | Lorio |
| 2016/0354124 A1 | 12/2016 | Bucci et al. |

FOREIGN PATENT DOCUMENTS

| | | |
|---|---|---|
| CN | 203354708 | 12/2013 |
| CN | 204698761 | 10/2015 |
| EP | 0880950 | 12/1998 |
| JP | 2009195313 | 9/2009 |
| JP | 2011152156 | 8/2011 |
| KR | 101052833 | 7/2011 |
| WO | 0023014 | 4/2000 |
| WO | 2009129605 | 10/2009 |
| WO | 2011028236 | 3/2011 |
| WO | 2017190236 | 11/2017 |

\* cited by examiner

FLEXIBLE INTERBODY SPACER AND METHODS FOR USE

CROSS REFERENCE TO RELATED APPLICATION

This application is a continuation of U.S. application Ser. No. 17/301,157 filed on Mar. 26, 2021 and entitled Flexible Interbody Spacer and Methods for Use, which issued as U.S. Pat. No. 11,497,614 on Nov. 15, 2022, and which is a continuation of International Application No. PCT/US2019/053276 filed on Sep. 26, 2019 and entitled Flexible Interbody Spacer and Methods for Use, which claims priority benefit under 35 U.S.C. § 119(e) of U.S. provisional application No. 62/737,095 filed Sep. 26, 2018 and entitled Flexible Interbody Spacer and Methods for Use, which are incorporated herein by reference in their entireties.

FIELD OF THE INVENTION

The present disclosure relates generally to general surgery, orthopaedic and neurosurgical implants used for insertion between two bone segments of a patient. More specifically, but not exclusively, the present disclosure concerns interbody cage devices, systems and methods of using the same.

BACKGROUND OF THE INVENTION

The present disclosure generally relates to devices and methods that provide structural support to aspects of a spine, and in particular to interbody cages, vertebral body replacements, and/or corpectomy cages and related methods that facilitate arthrodesis, interbody fusion, and/or dynamic stabilization of a motion segment of a spine.

Spinal pathology and surgery are common in patients with spinal cord compression and/or nerve root compression when conservative treatments have failed. The current standard and most commonly utilized procedure in the cervical spine is an anterior cervical discectomy and fusion (ACDF). Commonly, in ACDF, one or multiple levels of the cervical spine are exposed from an anterior approach. The spine is then distracted and discectomy and decompression are performed. A bone graft or interbody implant (referred to as a "cage" or "spacer") is often placed to fill the vacated disc space and to assist in maintaining disc height. In the cervical and lumbar regions of the spine, it is common to remove two or more adjacent intervertebral discs and the interconnecting vertebral bodies and replacing them with a single construct. This procedure is commonly referred to as a corpectomy and the device is commonly referred to as a corpectomy cage or vertebral body displacement. In this disclosure, corpectomy cages, vertebral body replacements, and interbody cages may be used interchangeably.

Interbody cages typically serve two main purposes. First, some interbody cages may act as a containment device for a bone graft. Secondly, some interbody cages may fill a vertebral body defect or an intervertebral defect and, potentially, resist axial loading of the spine. In the cervical, thoracic and lumbar regions of the spine, corpectomies, or removal of the vertebrae, is often performed, such as in cases of degenerative disease, trauma (burst fractures), tumors of the spine, and infections of the disc and vertebrae. In such cases, an interbody cage is usually inserted from the anterior or lateral regions of the vertebrae, though they may be inserted through a posterior approach.

In typical practice, once an interbody cage is implanted between adjacent endplates of the spine, a spinal fixation plate, screws, and/or rods are used to stabilize the spine and to foster arthrodesis. Spinal fixation plates/rods may span a single intervertebral disc and affix to two adjacent vertebrae for a single level procedure. Multiple level applications may also be performed. Most commonly, spinal fixation plates/rods are affixed to the vertebrae using bone fixation devices, such as bone screws.

While static bone plates/rods and interbody cages may be effective at stabilizing the spine in some applications, the inventors have appreciated that they may cause graft stress shielding, graft overloading, subsidence, and/or graft failure. Another common complication associated with plate fixation in the spine, such as in the cervical spine, following anterior interbody arthrodesis is dysphagia. Dysphagia is commonly caused by irritation of the esophagus and surrounding tissue due to the implant which may extend at least partially out of the intervertebral disc space. In some embodiments, dynamic plate implants have been designed to provide load sharing during flexion/extension of the spine to minimize graft overloading and/or promote loading through the bone graft.

All-in-one cage-plate implants may provide some of the advantages of plating including resistance to flexion-extension motion, lateral bending motion, and torsion. Cage-plate implants may also provide the advantages of cages including resistance to flexion (compression) and support for bone graft. The goal of these devices is to stabilize the spine to facilitate bony fusion. However, typical cage-plates are formed of static components that are fraught with the complications associated with static plate fixation, namely graft stress shielding, graft overloading, subsidence, and graft failure. Graft stress shielding or graft overloading can lead to fibrous tissue formation or bone resorption, ultimately resulting in pseudarthrosis. For example, excessive strain on a bone graft and forming bone may lead to a fibrous non-union. As another example, inadequate strain on a bone graft and forming bone may lead to protracted bone formation. Excessive motion may also lead to bone resorption and pseudarthrosis. Micromotion which exceeds 100 microns can lead to osteolysis and loss of osseointegration.

Total disc replacement and dynamic stabilization is an alternative to arthrodesis for some patients with spinal degeneration. However, total disc replacement has different goals than arthrodesis and fusion. Total disc replacements attempt to return the disc to physiologic motion including flexion, extension, lateral bending, and torsion. Disc replacement devices are often structured to prohibit bony through-growth to facilitate long term motion preservation of the spinal motion segment.

As a result, a need exists for devices and methods that utilize a bone graft and provide for the appropriate balance of facilitating load sharing while eliminating and/or reducing stress shielding and excessive motion to achieve arthrodesis and/or fusion.

SUMMARY OF THE INVENTION

Aspects of the present disclosure provide interbody cage devices, systems and methods of using the same.

In one aspect, the present disclosure provides an interbody cage including superior and inferior members each including an engagement surface for engaging a corresponding vertebra. The interbody cage also includes a flexible connecting member that extends between the superior and inferior members and spaces them from each other in a superior-inferior direction. The connecting member is comprised of a shape that facilitates elastic deformation and relative translation between the superior and inferior members. The superior and inferior members extend in a posterior-to-anterior direction and define anterior free ends to form a substantially open anterior end between the superior member and the inferior member. The engagement surfaces of the superior and inferior members may substantially diverge from each other in the superior-inferior direction along the posterior-to-anterior direction. The superior and inferior members each include first apertures extending therethrough in the superior-inferior direction that define a pathway through the interbody cage in the superior-inferior direction.

In another aspect, provided herein is an interbody spacer including a first endplate, a second endplate, and a coupling member coupled to and extending between the first endplate and the second endplate. The coupling member including at least two lateral members and at least one gap formed between every two adjacent lateral members of the at least two lateral members.

In yet another aspect, provided herein is an interbody spacer. The interbody spacer including a first endplate, a second endplate, and a coupling member coupled to and extending between the first endplate and the second endplate. The coupling member including a posterior member extending between the first endplate and the second endplate, at least one first longitudinal member extending from the first endplate on an anterior side of the interbody spacer, and at least one second longitudinal member extending from the second endplate on an anterior side of the interbody spacer.

In still another aspect, provided herein is an interbody spacer. The interbody spacer including a first cage and a second cage. The first cage including a first endplate, a second endplate with a first portion of a connecting feature positioned on an inferior surface of the second endplate, and at least one connecting member extending between and coupled to the first endplate on a first end and the second endplate on a second end. The second cage including a third endplate, a fourth endplate with a second portion of the connecting feature positioned on a superior surface of the fourth endplate, and at least one connecting member extending between and coupled to the third endplate on a first end and the fourth endplate on a second end. The first portion of the connecting feature coupled to the second portion of the connecting feature to secure the first cage to the second cage.

In yet another aspect, provided herein is a surgical method for using the interbody cage.

These, and other objects, features and advantages of this disclosure will become apparent from the following detailed description of the various aspects of the disclosure taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion.

DETAILED DESCRIPTION FOR CARRYING OUT THE INVENTION

Generally stated, disclosed herein are bone fusion systems, implants, devices and instruments. Further, surgical methods for inserting the implants are discussed.

In this detailed description and the following claims, the words proximal, distal, anterior, posterior, medial, lateral, superior, inferior, cephalad and caudally are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the implant, "posterior" means a direction towards the back side of the implant, "medial" means towards the midline of the implant, "lateral" is a direction towards the sides or away from the midline of the implant, "superior" means a direction above and "inferior" means a direction below another object or structure, "cephalad" means a direction toward the head and "caudally" means a direction toward the inferior part of the body.

Similarly, positions or directions may be used herein with reference to anatomical structures or surfaces. For example, as the current devices and methods are described herein with reference to use with the bones of the spine, the bones of the spine may be used to describe the surfaces, positions, directions or orientations of the devices, instrumentation and methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the device and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices and methods, and the aspects, components, features and the like thereof, described herein with respect to a right side of the spine may be mirrored so that they likewise function with a left side of the spine and vice versa.

Figure 1:
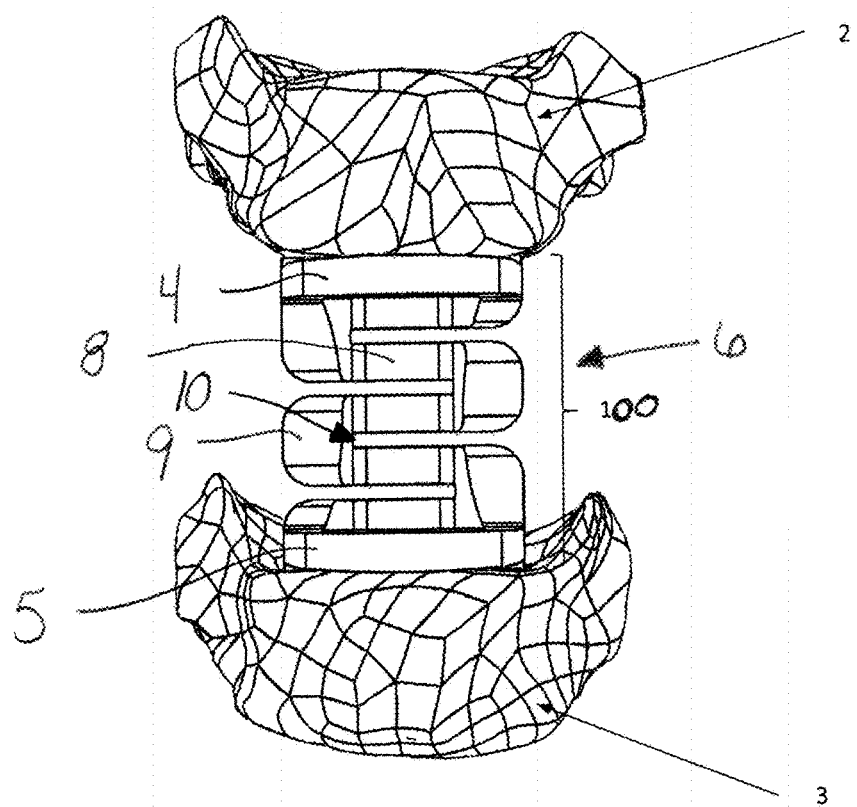
FIG. 1 is a first end view of an interbody spacer positioned between two vertebrae, in accordance with an aspect of the present disclosure.
Figure 77:
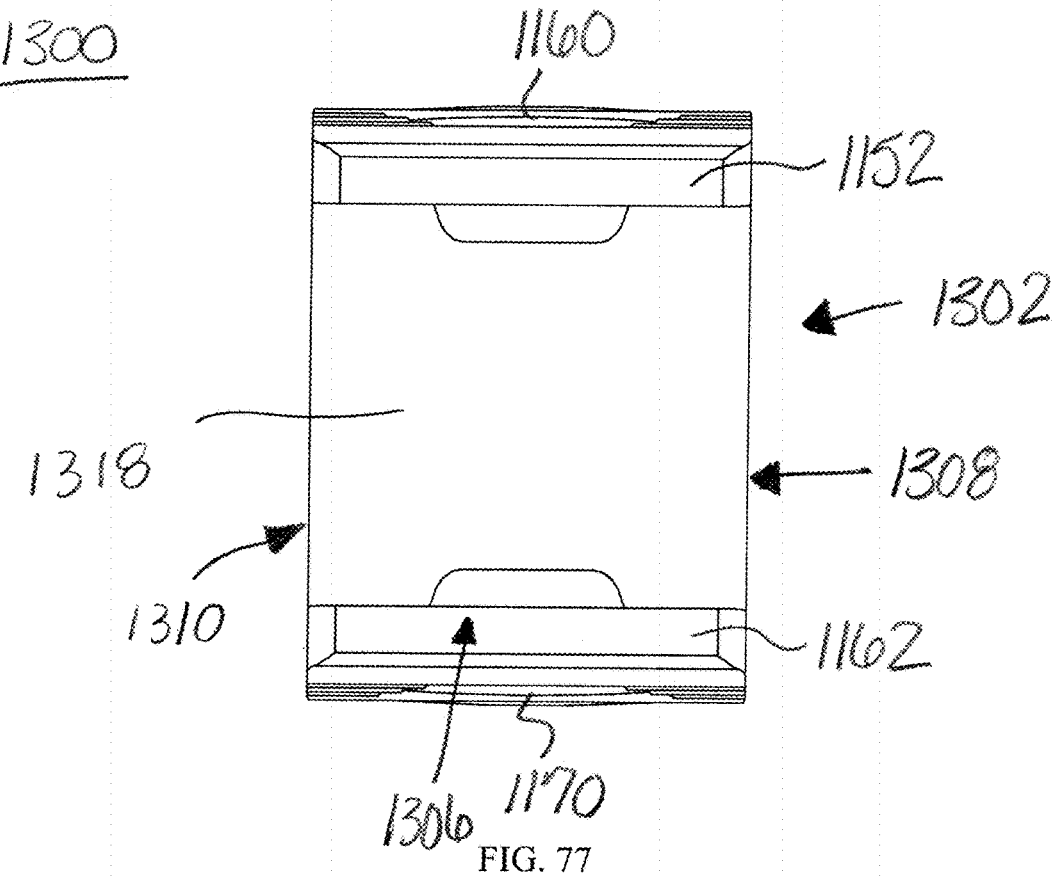
FIG. 77 is a second end view of the interbody spacer of FIG. 72, in accordance with an aspect of the present disclosure.

Referring to the drawings, wherein like reference numerals are used to indicate like or analogous components throughout the several views, and with particular reference to FIGS. 1-77 corpectomy cages or implants 100, 150, 200, 250, 300, 350, 400, 450, 500, 550, 600, 650, 700, 750, 800, 850, 900, 950, 1000, 1050, 1100, 1150, 1200, 1250, 1300. The terms "interbody spacer," "spacer," "deformable interbody cages," "vertebral body replacements," "corpectomy cages," "cages," "vertebral body displacement," "implants," and "devices" may be used interchangeably herein to refer to the spinal support structures described in the disclosure.

Figure 2:
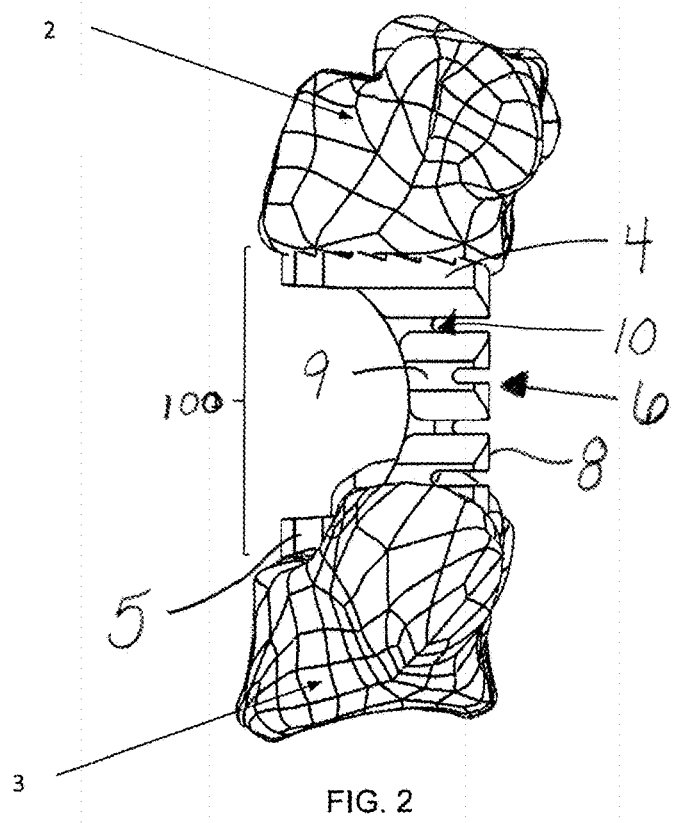
FIG. 2 is a first side view of the interbody spacer and vertebrae of FIG. 1, in accordance with an aspect of the present disclosure.
Figure 3:
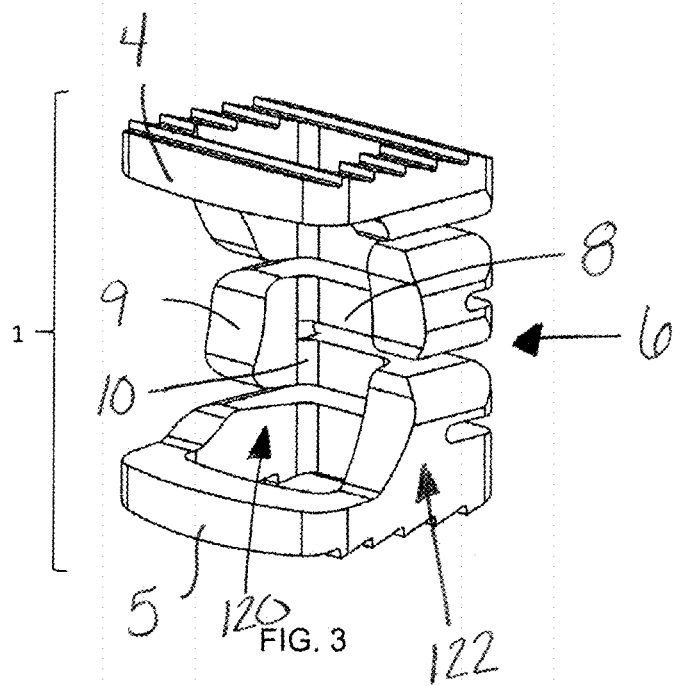
FIG. 3 is a perspective view of the interbody spacer of FIG. 1, in accordance with an aspect of the present disclosure.
Figure 4:
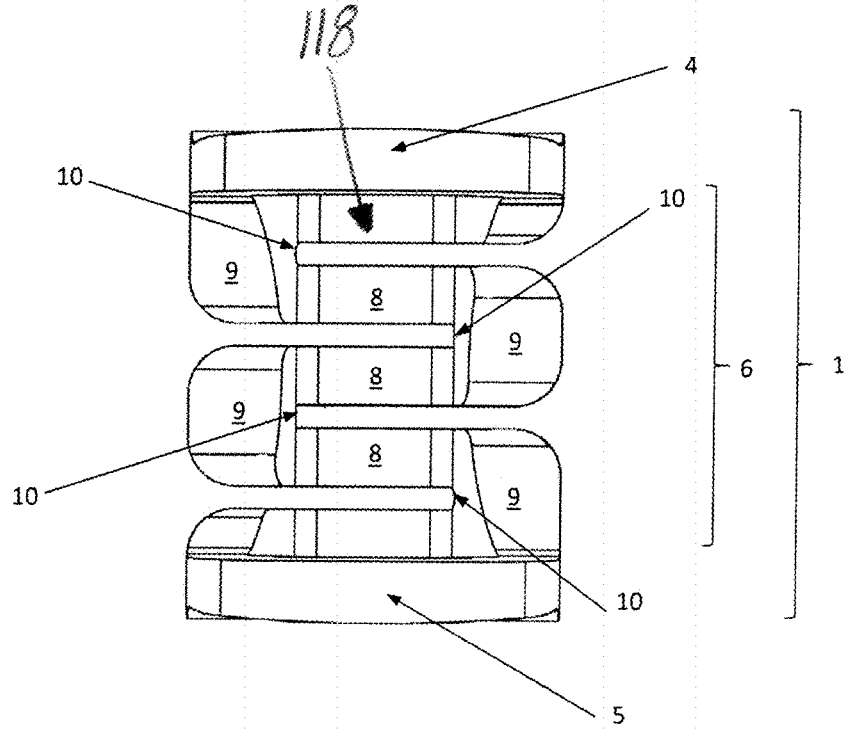
FIG. 4 is a first end view of the interbody spacer of FIG. 1, in accordance with an aspect of the present disclosure.

Referring now to FIGS. 1-8, corpectomy cages or implants 100, 100' are shown. FIGS. 1 and 2 shows an anterior view and lateral view, respectively, of the corpectomy cage 100 positioned between two vertebral bodies 2, 3. The vertebral bodies 2, 3 may be located in the cervical, thoracic, or lumbar regions of the spine. As shown, the corpectomy cage 100 spans across two intervertebral disc spaces and one vertebral body height; however, it is understood that the corpectomy cage 100 may also span more than two disc spaces and more than one vertebral body height if multiple vertebral bodies were removed during the procedure. The corpectomy cage 100 is also shown without vertebral bodies in various orientations in FIGS. 3-6. The implant includes a superior endplate 4, an inferior endplate 5, and a connecting member 6 extending between and coupling the superior endplate 4 to the inferior endplate 5. The superior and inferior endplates 4, 5 may be, for example, rigid endplates.

Figure 5:
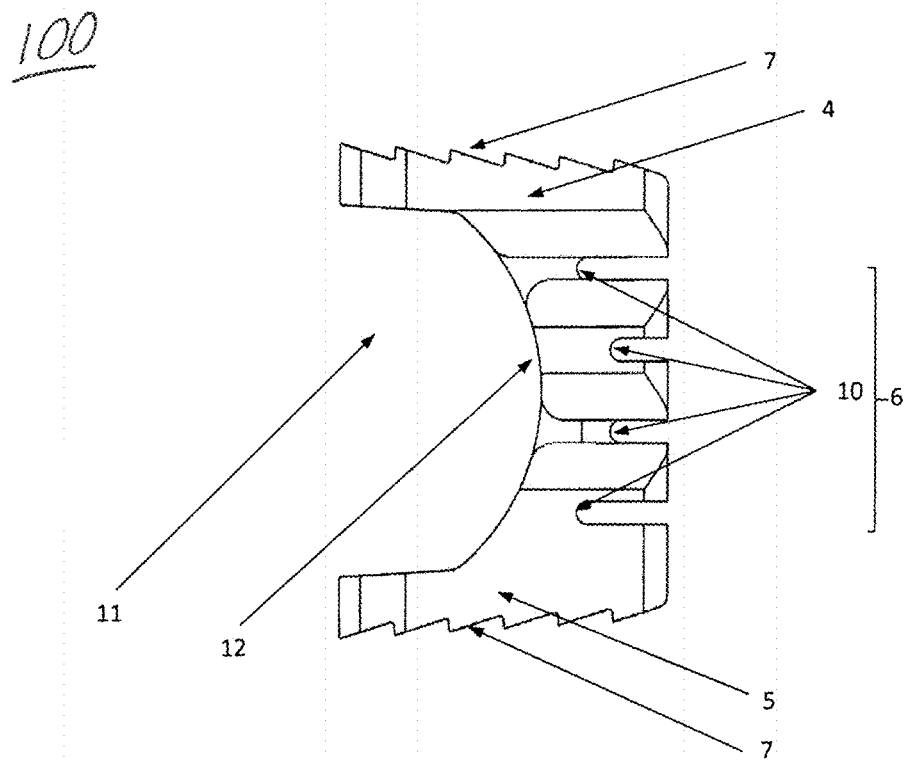
FIG. 5 is a first side view of the interbody spacer of FIG. 1, in accordance with an aspect of the present disclosure.

The endplates 4, 5 may include a textured surface 7 to improve connection with adjacent vertebral bodies 2, 3 and minimize relative motion and/or expulsion between the implant 100 and the vertebral bodies 2, 3. As shown in FIG. 5, the textured surface 7 may be, for example, "teeth" with a substantially triangular cross-section. It is also contemplated that the textured surface 7 may include, for example, roughened or porous surfaces, as well as other surface textures as would be known by one of ordinary skill in the art. The triangular cross-section is depicted as scalene and oriented in such a way that the cage 100 is inserted into the interbody space more easily than it would be removed/expelled. The endplates 4, 5 are depicted as diverging in a posterior-to-anterior direction. It is also contemplated that the endplates 4, 5 may be, for example, parallel, concave, convex, or any combinations thereof as the endplates 4, 5 extend in a posterior-to-anterior direction. The first endplate 4 may be, for example, the same or similar to a first or superior endplate 1152, as described in greater detail below with reference to FIGS. 54-59, which will not be described again here for brevity sake. The second endplate 5 may be, for example, the same or similar to a second or inferior endplate 1162, as described in greater detail below with reference to FIGS. 54-59, which will not be described again here for brevity sake.

With continued reference to FIGS. 1-8, the connecting member 6 is shown to be "serpentine in shape." The connecting member 6 includes lateral members, straight members, or substantially horizontal members 8 and longitudinal members, curved members, or substantially vertical members 9. As used herein the term "horizontal members" may refer to structures which are positioned perpendicular to a superior-inferior axis of the implants, as well as structures which are positioned slightly offset from or angled with respect to the superior-inferior axis, such that the structures are substantially horizontal, which means the angle with respect to the superior-inferior axis is larger than an angle with respect to a medial-lateral axis. In addition, as used herein the term "vertical members" may refer to structures which are positioned parallel with the superior-inferior axis of the implants, as well as structures which are positioned slightly offset from or angled with respect to the superior-inferior axis, such that the structures are substantially vertical, which means the angle with respect to the superior-inferior axis is smaller than the angle with respect to the medial-lateral axis. The connecting member 6 may also include a posterior portion 118 and two lateral portions 120, 122.

With respect to implant 100 and as described in greater detail below with respect to implants 1150, 1200, 1300, the lateral members 8, 1184, 1190, 1216, 1316 may extend along a first plane or horizontal plane when the implant 100, 1150, 1200, 1300 is inserted into a patient. In some embodiments, the lateral members 8, 1184, 1190, 1216, 1316 may be aligned with, i.e. parallel to, the horizontal plane and in other embodiments, the lateral members 8, 1184, 1190, 1216, 1316 may be rotationally or angularly adjustable with respect to the horizontal plane. The longitudinal members 9, 1186, 1192 may extend along a second plane or sagittal plane when the implant 100, 1150 is inserted into a patient. In some embodiments, the longitudinal members 9, 1186, 1192 may be aligned with, i.e. parallel to, the sagittal plane and in other embodiments, the longitudinal members 9, 1186, 1192 may be rotationally or angularly adjustable with respect to the sagittal plane.

Figure 7:
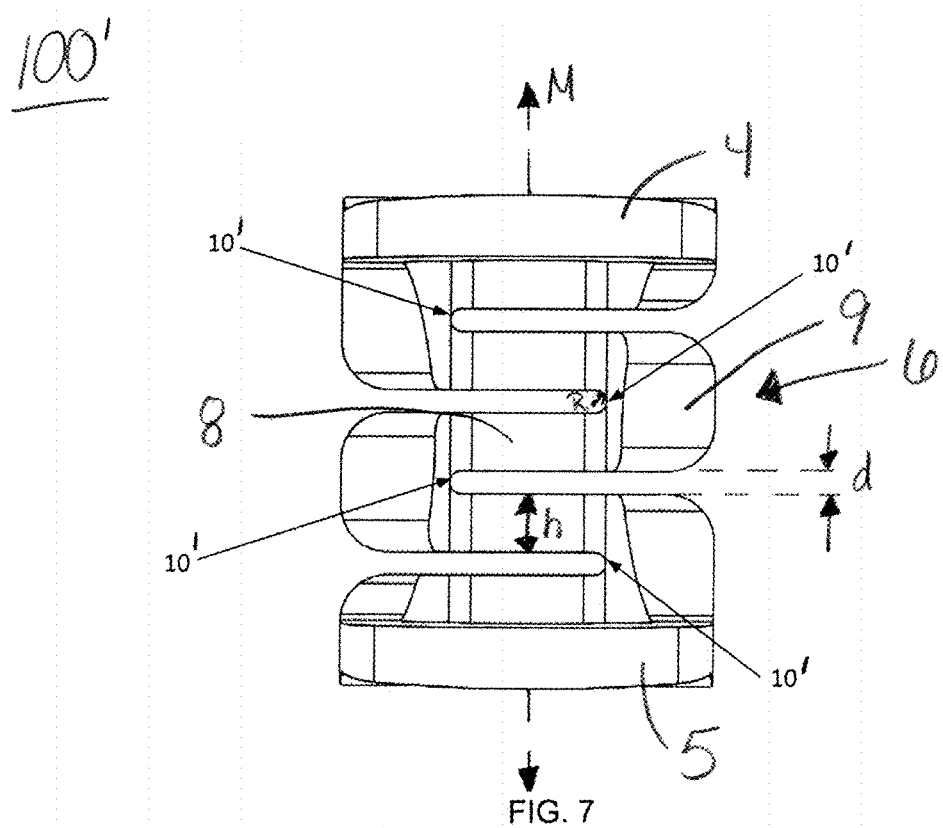
FIG. 7 is the first end view of an alternative embodiment of the interbody spacer of FIG. 1 showing a midline M and the radii of the junctions terminating in the posterior side of the interbody spacer, in accordance with an aspect of the present disclosure.
Figure 8:
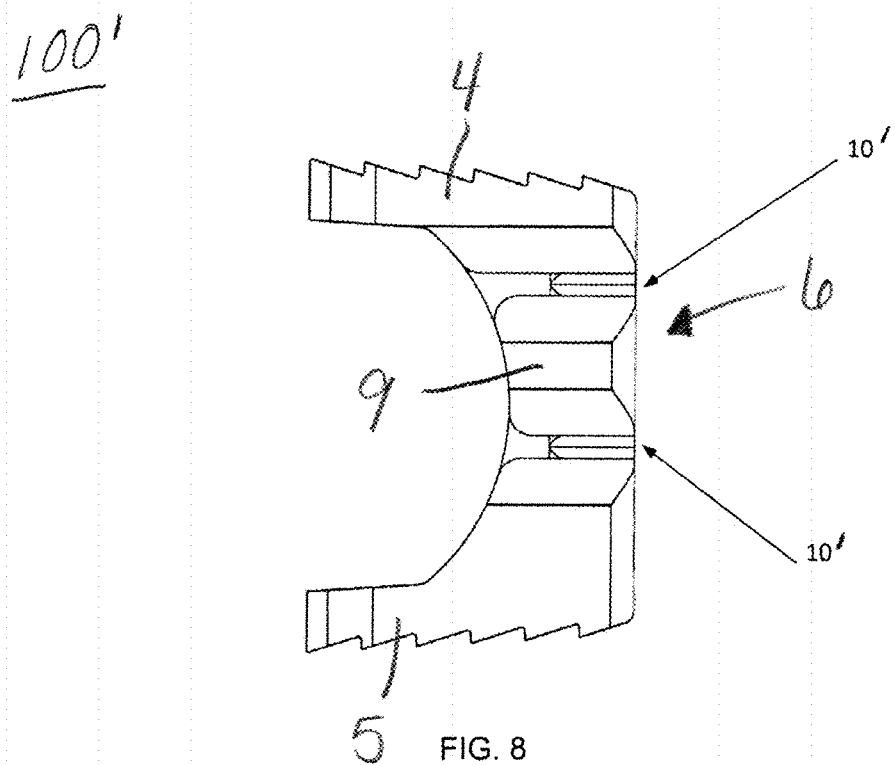
FIG. 8 is a first side view of the interbody spacer of FIG. 7, in accordance with an aspect of the present disclosure.

The horizontal members 8 connect to the vertical members 9 at a junction 10. In the embodiment shown in FIGS. 1-6, the junction 10 is located on the two lateral portions 120, 122 of the connecting member 6. In an alternative embodiment, FIGS. 7-8 depict the junction 10' being located on a posterior portion, wall, or side 118 of the implant 100' and positioned near the lateral portions 120, 122. The junction 10' may include, for example, a radius R that is equal to half of the distance d between two horizontal members 8, as shown in FIG. 7. It is also contemplated that this radius R may be, for example, larger or smaller with respect to the relative distance d between the two horizontal members 8. It is also understood that the distance d between horizontal members may also vary. As shown, the distance d between horizontal members 8 is approximately one-half of the height h of one of the horizontal members 8. The height h of one of the horizontal members 8 may also be smaller than the distance between two horizontal members 8. In the depicted embodiment, the connecting member 6 is attached to the superior endplate 4 on one side of a midline M and to the inferior endplate 5 on the contralateral side of midline M. In alternative embodiments, the connecting member 6 may be attached, for example, to at least one of the superior endplate 4 and the inferior endplate 5 at the midline M.

In the depicted embodiment, the posterior portion 118 and lateral portions 120, 122 of the connecting member 6 are present substantially posterior to the anterior surface of the implant, resulting in an open anterior portion 11 of the implant 100. The open anterior portion 11 allows for, for example, relative translation between the superior endplate 4 and inferior endplate 5 during physiologic loading. In addition, the open anterior portion 11 allows for improved post-surgical assessment of the region during radiographic imaging. The interbody and corpectomy cages 100 may, for example, facilitate a spinal fusion, where bone grows from one vertebra 2 to the adjacent vertebra 3. The bone growth is primarily assessed via x-ray or computed tomography (CT) scan. The presence of an interbody cage 100 can impede the assessment of bone growth. The substantially open anterior portion 11 of the implant 100 provides an improved assessment of the bone fusion during radiographic imaging. As shown in FIG. 5, the anterior surfaces 12 of the connecting member 6 may form an arcuate shape in a lateral view. The arcuate shape may allow for controlled elastic deformation. The radius of curvature of this anterior surface 12 can range in magnitude to control the compliance of the device 100. Similarly, the attachment portion between the connecting member 6 and the superior and inferior endplates 4, 5 can vary along the anterior-posterior direction. Doing such, will also allow for control of the compliance of the device 100.

Figure 6:
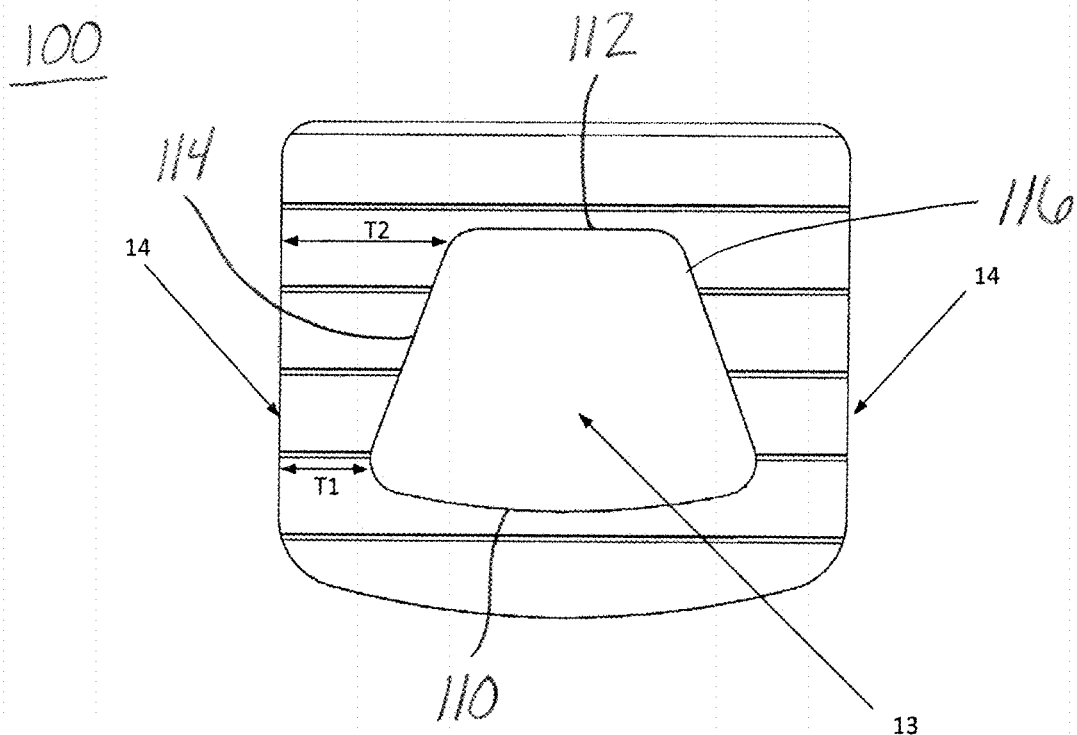
FIG. 6 is a top view of the interbody spacer of FIG. 1, in accordance with an aspect of the present disclosure.

As shown in the axial view of FIG. 6, each endplate 4, 5 of implant 100 may contain, for example, at least one aperture 13. The at least one aperture 13 allows for bone to grow through the implant 100 during a spinal fusion. It is also contemplated that in motion preservation devices, such as a dynamic stabilization device, the endplates 4, 5 may not contain an aperture 13. In the depicted embodiment, the anterior portion of the aperture 13 is, for example, larger than the posterior portion. In other words, the thickness of the lateral portion of the endplate 4, 5 may be, for example, smaller at the anterior portion T1 than it is at the posterior portion T2. It is also contemplated that these two thicknesses T1, T2 may be equal or the anterior thickness T1 may be larger than the posterior thickness T2. The aperture 13 may include, for example, a first end 110 opposite a second end 112 and a first side 114 opposite the second side 116. The first side 114 may engage the first end 110 at one end and the second end 112 at the other end. The second side 116 may also engage the first end 110 at one end and the second end 112 at the other end. The first and second sides 114, 116 may be, for example, angled or curved as the sides extend between the first and second ends 110, 112.

FIG. 6 also depicts the lateral sides 14 of the implant 100 to be parallel in a posterior-anterior direction. In another embodiment, the lateral sides 14 of the implant 100 may be, for example, divergent in a posterior-to-anterior direction. In other embodiments, the lateral sides 14 may, for example, converge or may contain a radius such that a portion of the lateral sides 14 converge while another portion may diverge.

As depicted in FIGS. 7 and 8, the junctions 10 between the horizontal and vertical members 8, 9 are located on the posterior portion 118 of the connecting member 6. This location may provide for, for example, a less compliant construct than alternative embodiments.

The implant 100 may include horizontal members 8 extending along a posterior side of the implant 100. A portion of the horizontal members 8 may also extend from the posterior side of the implant 100 along the lateral sides toward the anterior side of the implant 100. The vertical members 9 may also be positioned on the lateral sides of the implant 100. The anterior surfaces 12 of the connecting member 6 may be, for example, curved or arced as the anterior surfaces 12 extend between the first endplate 4 and the second endplate 5.

Figure 9:
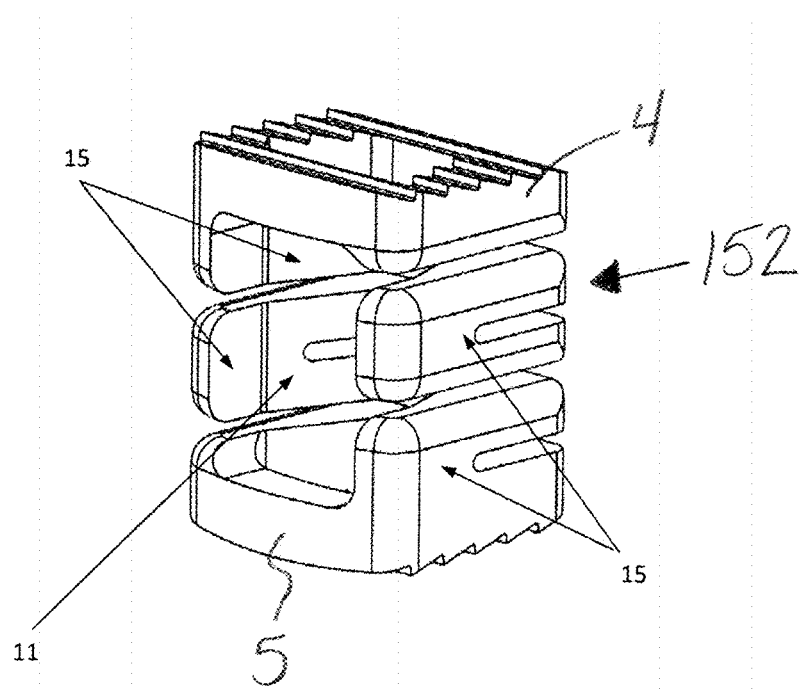
FIG. 9 is a perspective view of another interbody spacer, in accordance with an aspect of the present disclosure.
Figure 10:
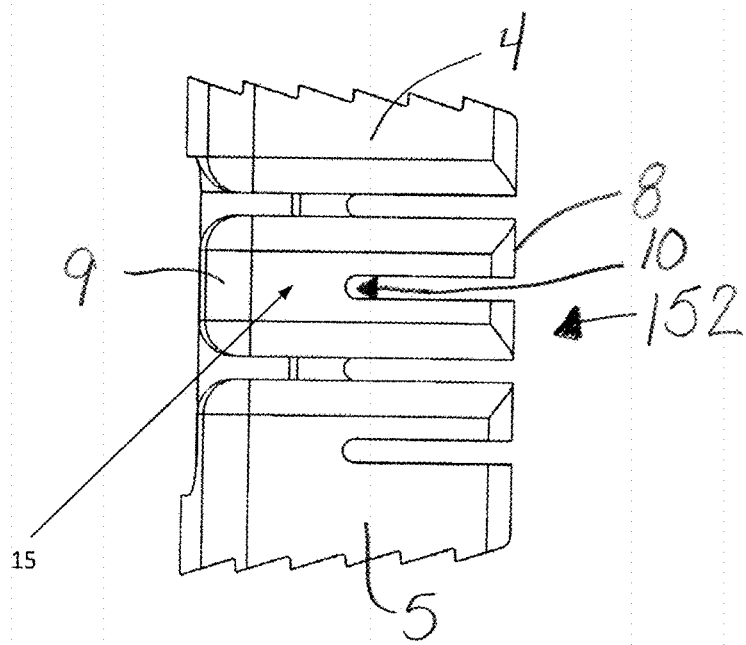
FIG. 10 is a side view of an interbody spacer of FIG. 9, in accordance with an aspect of the present disclosure.

Another implant, cage, or device 150 is depicted in FIGS. 9 and 10. The implant 150 may include endplates 4, 5 coupled together by a connecting member 152. The connecting member 152 may include lateral portions 15, which may extend so that the lateral portions 15 are in proximity to the anterior portion of the implant 150, such that the open anterior portion 11 cannot be seen in a lateral view of the implant 150 but can be seen in an anterior view. The lateral portions 15, as shown, may provide greater containment of bone graft material within the implant 150, which may be desirable.

Figure 11:
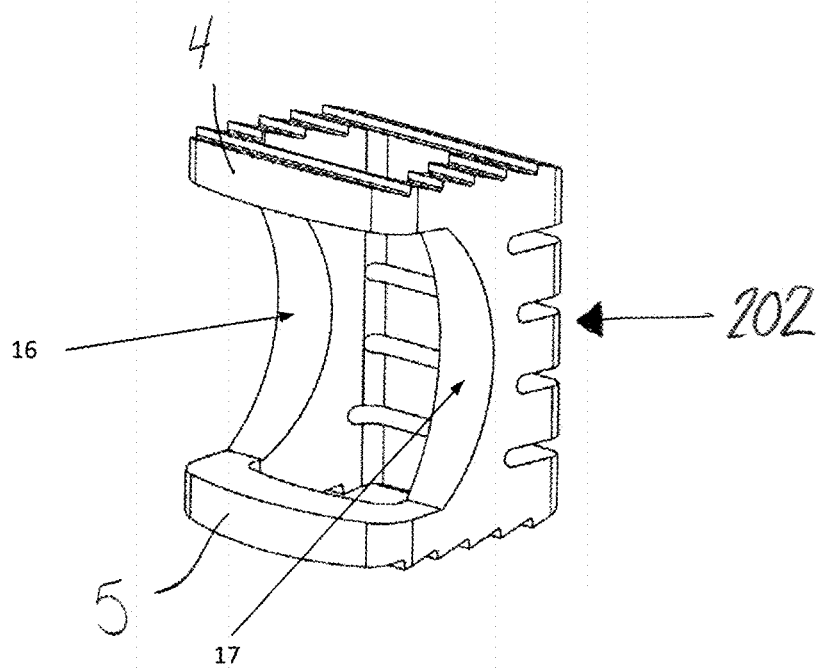
FIG. 11 is a perspective view of yet another interbody spacer, in accordance with an aspect of the present disclosure.
Figure 12:
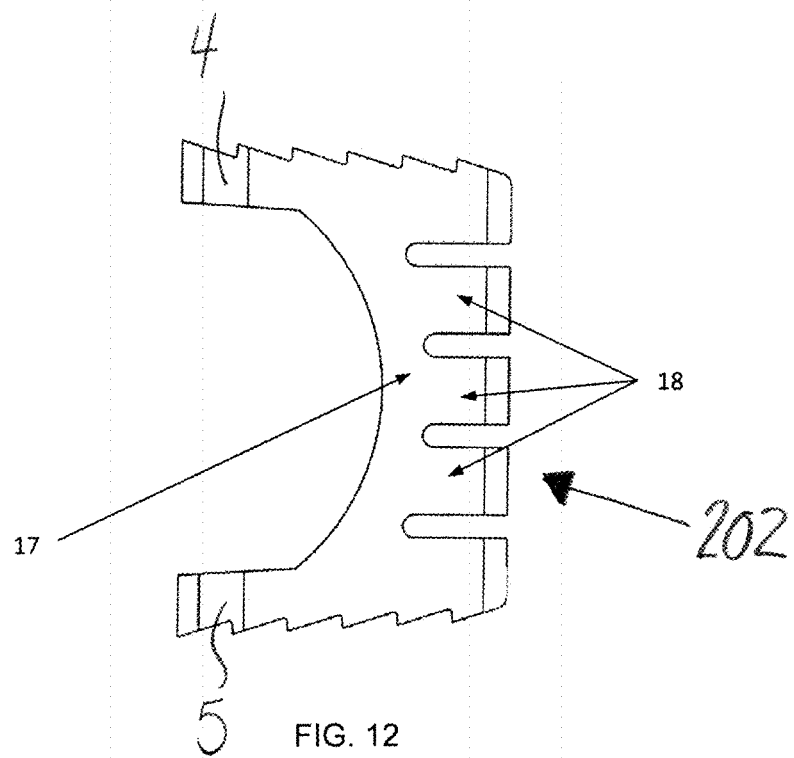
FIG. 12 is a side view of the interbody spacer of FIG. 11, in accordance with an aspect of the present disclosure.
Figure 13:
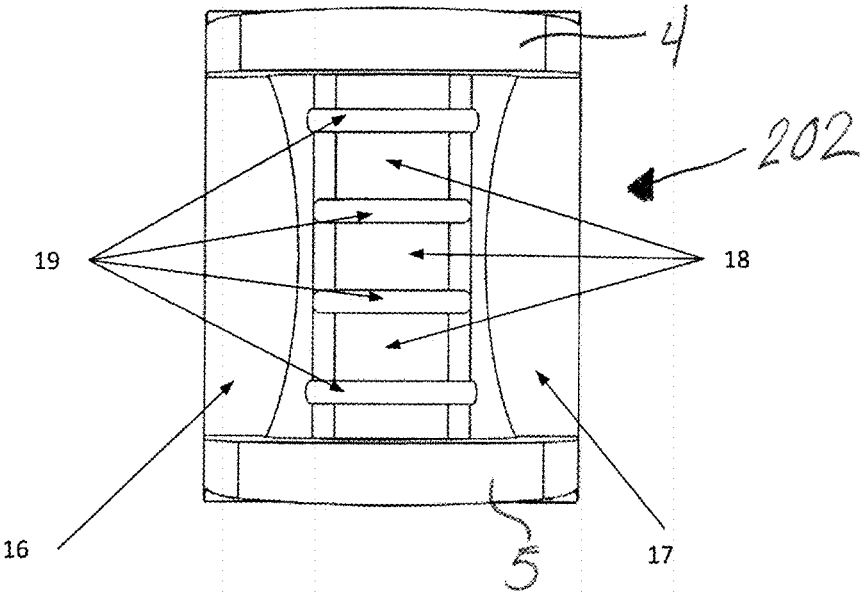
FIG. 13 is a first end view of the interbody spacer of FIG. 11, in accordance with an aspect of the present disclosure.
Figure 14:
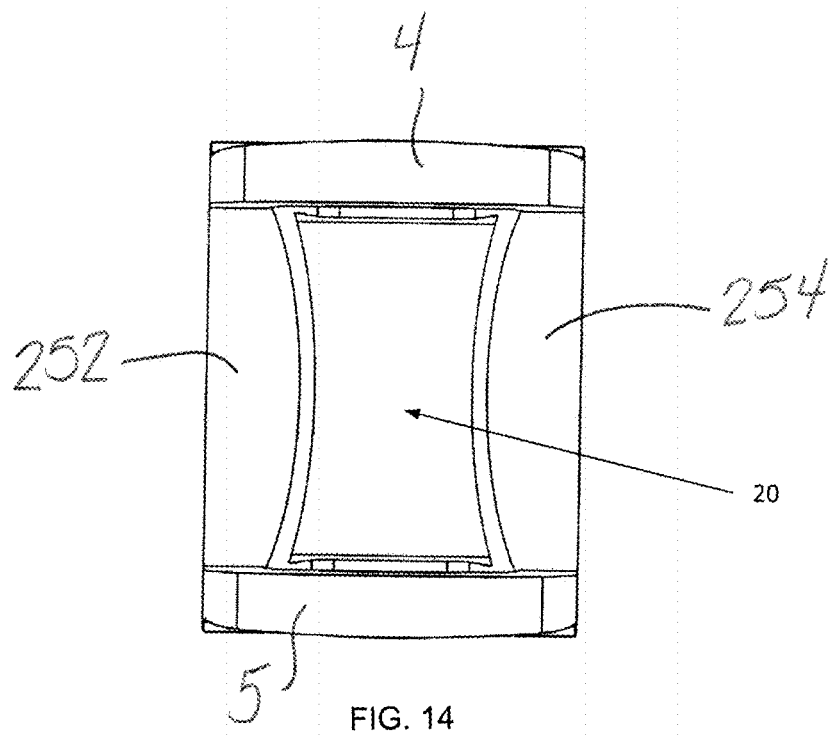
FIG. 14 is a first end view of another interbody spacer, in accordance with an aspect of the present disclosure.
Figure 15:
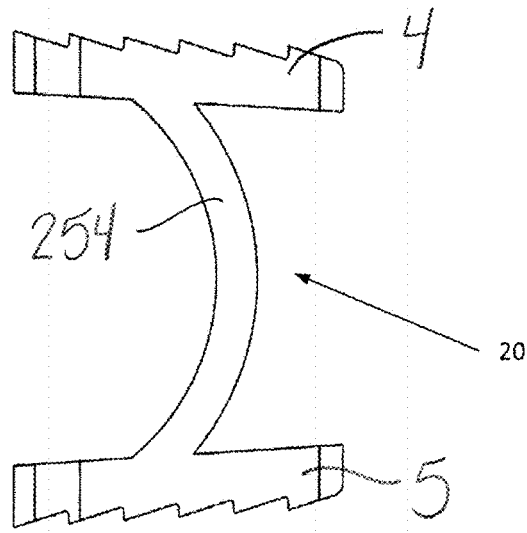
FIG. 15 is a first side view of one embodiment of the interbody spacer of FIG. 14, in accordance with an aspect of the present disclosure.
Figure 16:
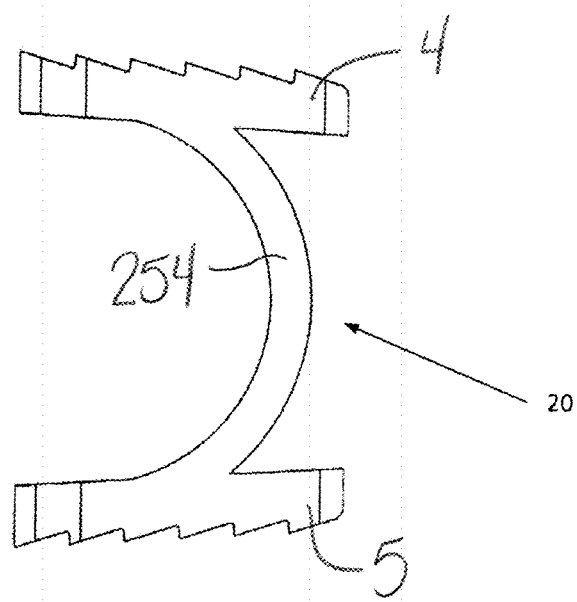
FIG. 16 is a first side view of another embodiment of the interbody spacer of FIG. 14, in accordance with an aspect of the present disclosure.
Figure 17:
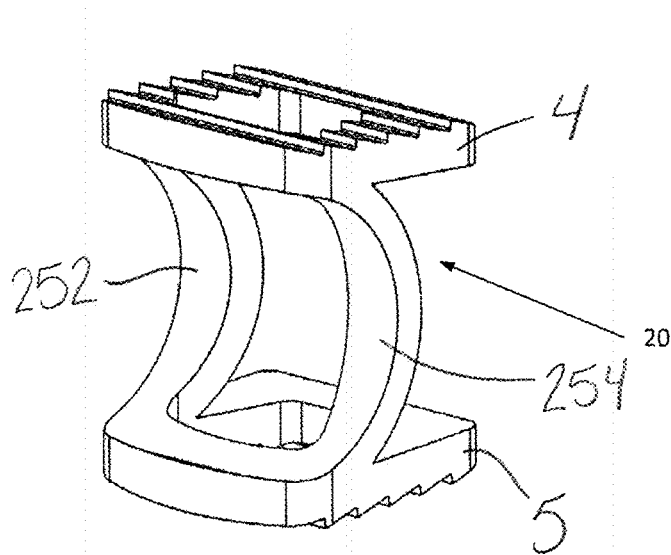
FIG. 17 is a perspective view of the interbody spacer of FIG. 14, in accordance with an aspect of the present disclosure.

Referring now to FIGS. 11-13, another implant, cage, device 200 is shown. The implant 200 may include endplates 4, 5 and a connecting member 202. The connecting member 202 is not serpentine in shape, but includes two arcuate members 16, 17 that connect the superior and inferior members 4, 5 on each lateral portion 15 of the implant 200. The arcuate members 16, 17 may be connected by at least one reinforcement member 18. The reinforcement members 18 may be positioned at posterior and/or anterior regions of the implant 200. The reinforcement members 18 may serve to contain bone graft, may facilitate a desired amount of compliance, and/or may allow for visualization of the spinal cord and/or dura via pores 19.

Figure 18:
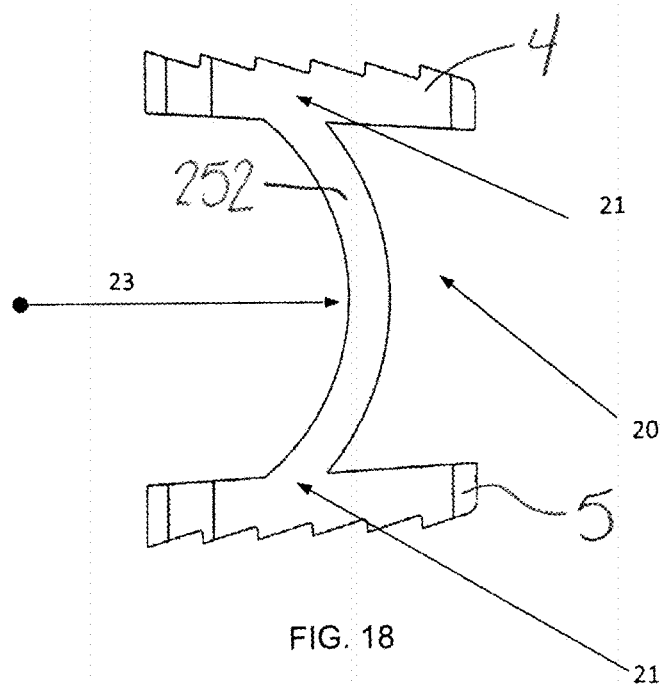
FIG. 18 is a first side view of the interbody spacer of FIG. 15 showing a radius of curvature of the connecting member, in accordance with an aspect of the present disclosure.
Figure 19:
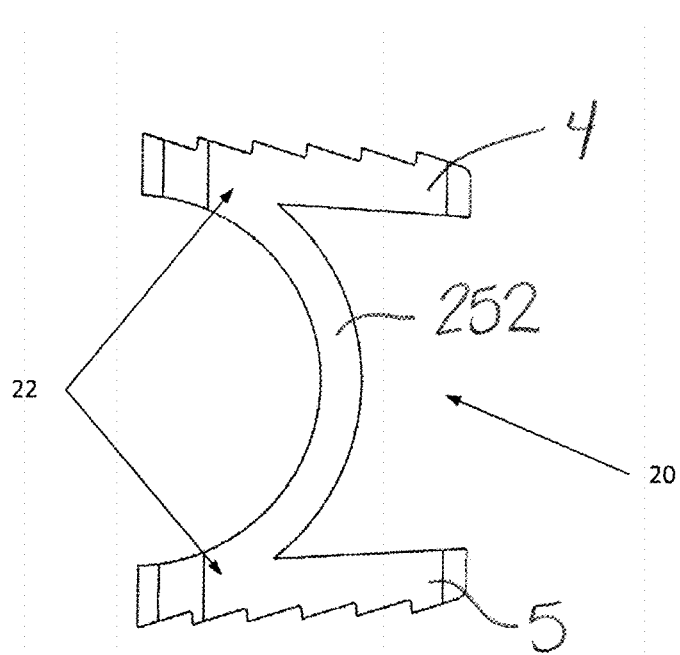
FIG. 19 is a first side view of another embodiment of the interbody spacer of FIG. 14 showing a radius of curvature of the connecting member, in accordance with an aspect of the present disclosure.
Figure 20:
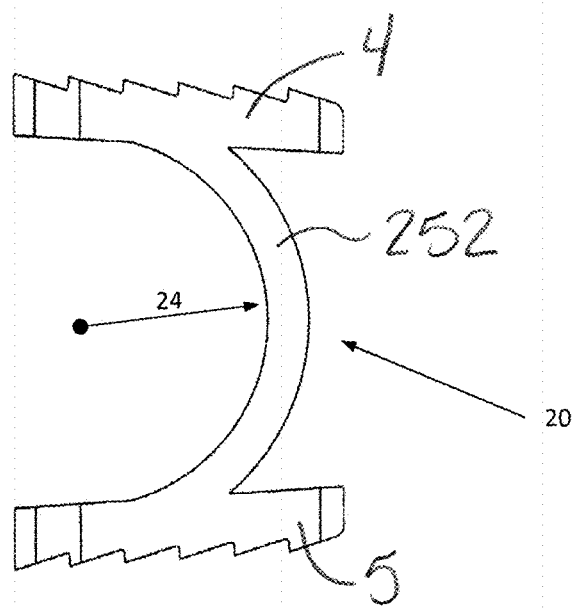
FIG. 20 is a first side view of the interbody spacer of FIG. 16 showing a radius of curvature of the connecting member, in accordance with an aspect of the present disclosure.
Figure 21:
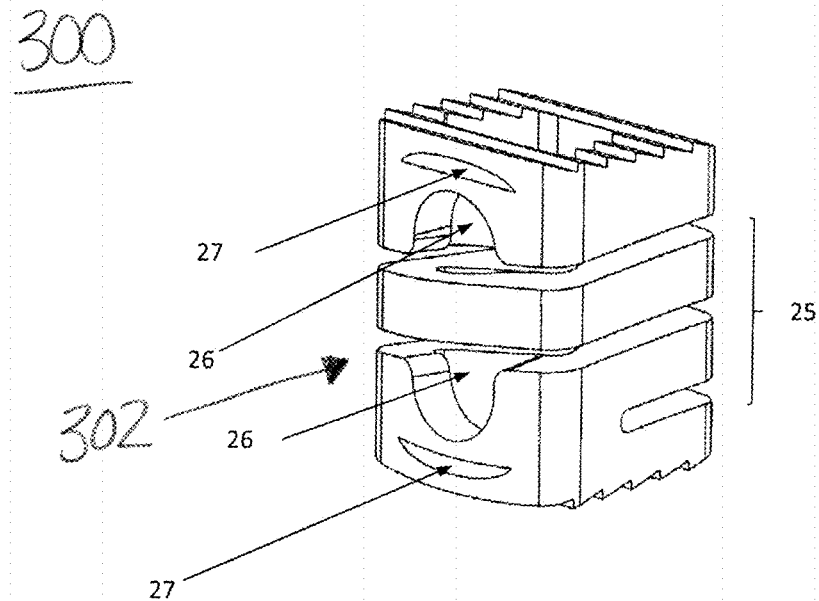
FIG. 21 is a perspective view of another interbody spacer, in accordance with an aspect of the present disclosure.
Figure 22:
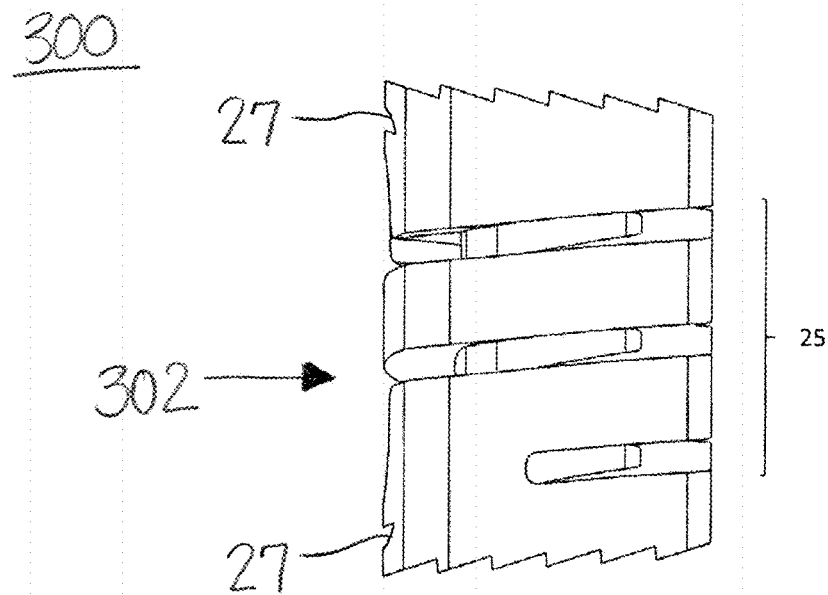
FIG. 22 is a side view of the interbody spacer of FIG. 21, in accordance with an aspect of the present disclosure.

Referring now to FIGS. 14-20, another implant, cage, or device 250 is shown. The implant 250 may have a region 20 which does not include reinforcement members that connect to the lateral connecting members. The region 20 may be an opening extending through the implant 250. The opening in region 20 facilitates full visualization of the all anatomy posterior to the implant 250. The implant 250 may also include lateral connecting members 252, 254 that attach to the superior and inferior members 4, 5 at various locations in the anterior-posterior direction. FIG. 18 illustrates the connecting members 252, 254 with connections near the middle 21 of the superior and inferior endplate 4, 5 in the lateral view. While FIG. 19 illustrates the connecting members 252, 254 with connections near the anterior portion 22 of the superior and inferior endplates 4, 5 in the lateral view. The radius of curvature of the lateral connecting members 252, 254 may also vary, which may facilitate various amounts of compliance. The various amount of compliance are depicted by a larger radius of curvature 23 in FIG. 18 and a smaller radius of curvature 24 in FIG. 20. The radius of lateral connecting members 252, 254, as well as their attachment locations to the superior and inferior members 4, 5 can vary in all embodiments shown herein.

In another embodiment, as depicted in FIGS. 21-24, another implant, cage or device 300 is shown. The implant 300 includes a connecting member 302 that is helical 25, rather than serpentine in shape. As shown, the helix shape 25 is attached to the superior endplate 4 on one side of midline of the implant 300 and to the inferior endplate 5 on the contralateral side of the implant 300. The helical connecting member 302 may substantially contain any bone graft material. In another embodiment, the connecting member 302 and/or endplates 4, 5 may contain additional pores 26. The pores 26 may allow for visualization through the implant 300 or may act as a feature to facilitate implant insertion. The implants 300 are often times temporarily affixed to an instrument so that the implant can be securely passed from the surgical preparation table into the patient. Once positioned in the patient, the implants 300 may be impacted using a blunt instrument or mallet. As such, it is often desirable to have features for attaching the implant 300 to insertion or removal instruments.

Figure 23:
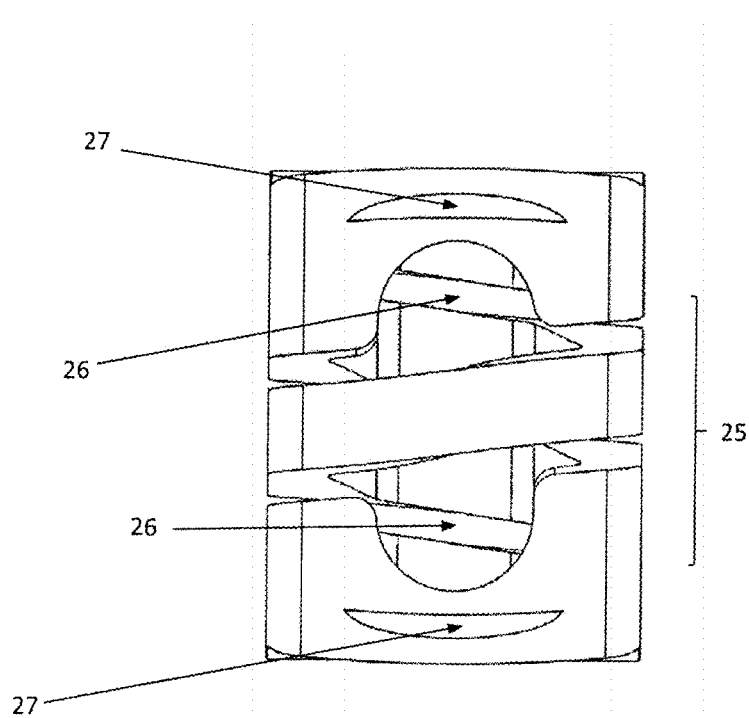
FIG. 23 is a first end view of the interbody spacer of FIG. 21, in accordance with an aspect of the present disclosure.
Figure 24:
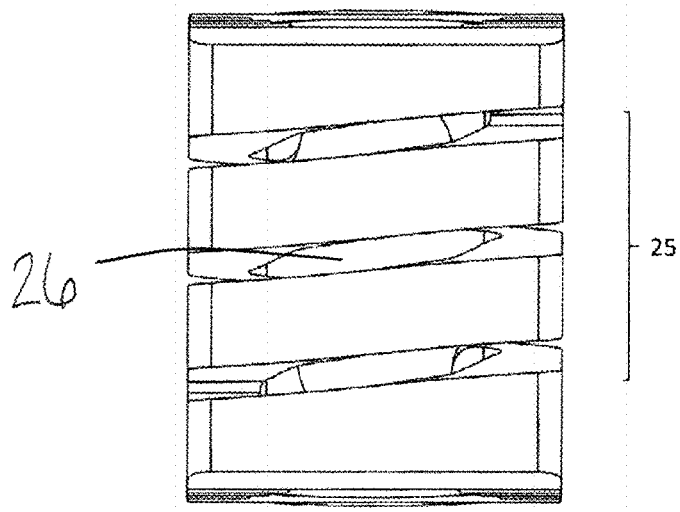
FIG. 24 is a second end view of the interbody spacer of FIG. 21, in accordance with an aspect of the present disclosure.

The pores 26 may also act as an access point for inserting bone graft material into the implant 300. The bone graft material can be inserted prior to insertion or in situ. FIG. 23 also depicts additional attachment features 27 for attachment to an insertion/removal instrument. These attachment features 27 can take many forms and shapes. As shown, the additional attachment features 27 may be, for example, grooves that mate with features of an instrument. The attachment features 27 are located on the anterior portion of the implant 300; however, it is understood that the attachment features 27 may be in other locations including the lateral, superior, inferior, posterior, or internal portions of the implant 300. The grooves 27 may be, for example, included on alternative implants described herein.

Figure 25:
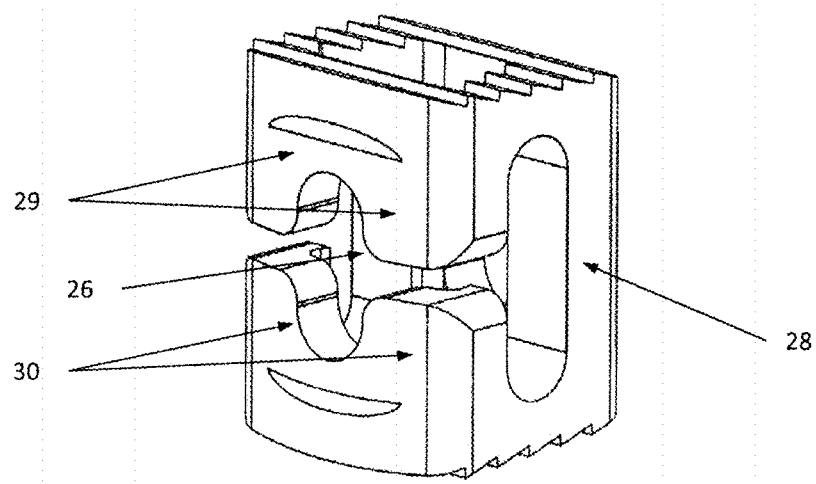
FIG. 25 is a perspective view of yet another interbody spacer, in accordance with an aspect of the present disclosure.
Figure 26:
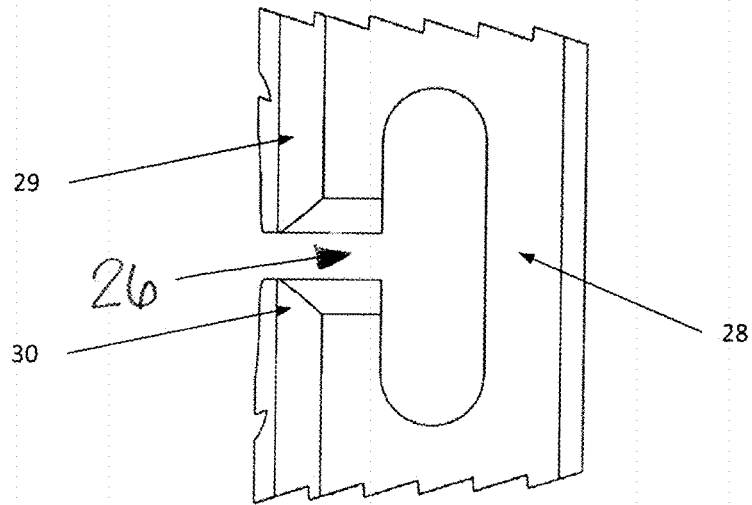
FIG. 26 is a side view of the interbody spacer of FIG. 25, in accordance with an aspect of the present disclosure.
Figure 27:
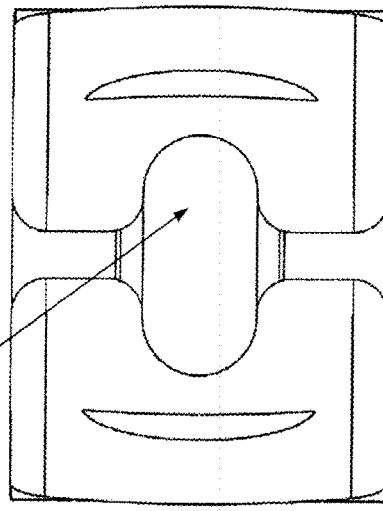
FIG. 27 is a first end view of the interbody spacer of FIG. 25, in accordance with an aspect of the present disclosure.

Referring now to FIGS. 25-27, another implant 350 is shown. The implant 350 may include a connecting member 28, which may be affixed to the posterior regions of the superior and inferior endplates 4, 5. The implant 350 may also include anterior members 29, 30 that are not directly connected to each other. The anterior members 29, 30 allows for relative displacement between the superior and inferior endplates 4, 5, particularly at the anterior region, but also provides an obstruction that contains the bone graft material within the implant. The anterior members 29, 30 may also act as a "hard stop" to prevent excessive relative displacement of the superior and inferior endplates. The implant 350 may also contain pores 26 on the anterior members 29, 30 to provide the same function as previously described. In the embodiment shown, the posterior member also contains a pore 31, that may provide the same function as previously described.

Figure 28:
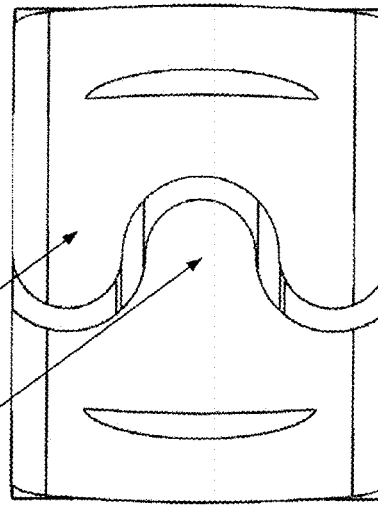
FIG. 28 is a first end view of another interbody spacer, in accordance with an aspect of the present disclosure.

In another embodiment, as shown in FIG. 28, another implant 400 is shown. The implant 400 includes the anterior members which may include, for example, alternative geometry 32, 33. The geometry 32, 33 may increase or decrease the amount of obstruction that is provided to the bone graft material.

Figure 29:
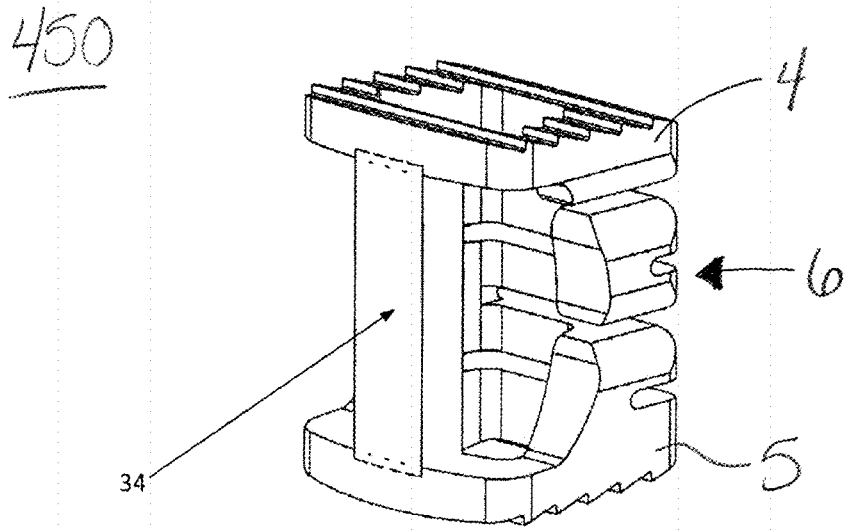
FIG. 29 is a perspective view of another interbody spacer, in accordance with an aspect of the present disclosure.
Figure 30:
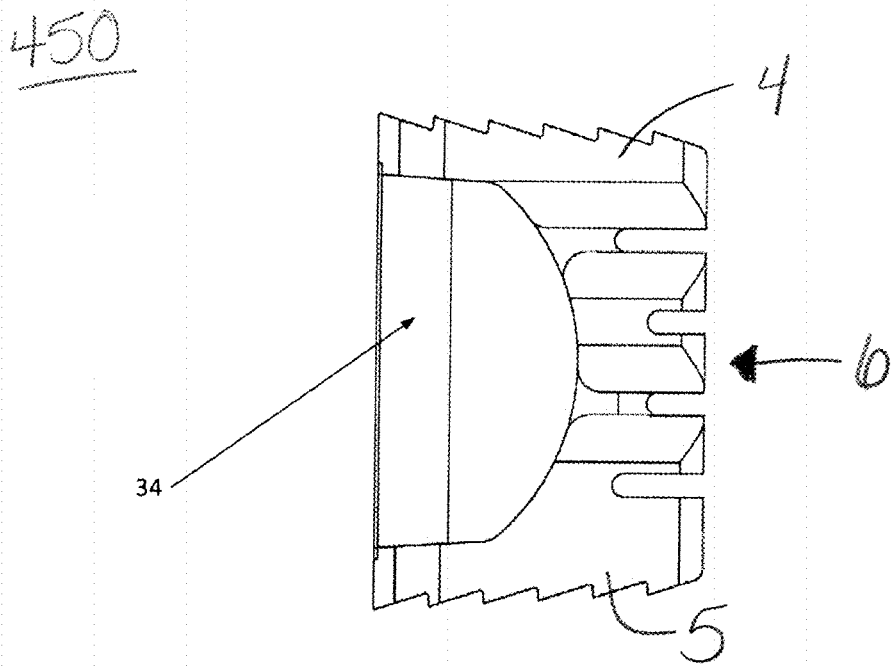
FIG. 30 is a first side view of the interbody spacer of FIG. 29, in accordance with an aspect of the present disclosure.

In another embodiment, as depicted in FIGS. 29 and 30, an implant 450 is shown. The implant 450 includes an anterior member 34 that connects the superior and inferior members 4, 5. The member 4, 5 may be, for example, integral to all other features of the implant 450 or it may be a separate component that is attached to the endplates 4, 5 of the implant 450. The anterior member 34 may be made of, for example, the same material as the implant 450, or it may be made of a different material. In addition, the anterior member 34 may be made of an elastic material. For example, the connector member 34 may be made of a polymer, such as PEEK. PEEK is biocompatible, more compliant than most metals, and is also radiolucent, which will aid in the assessment of the spinal fusion via radiograph.

Figure 31:
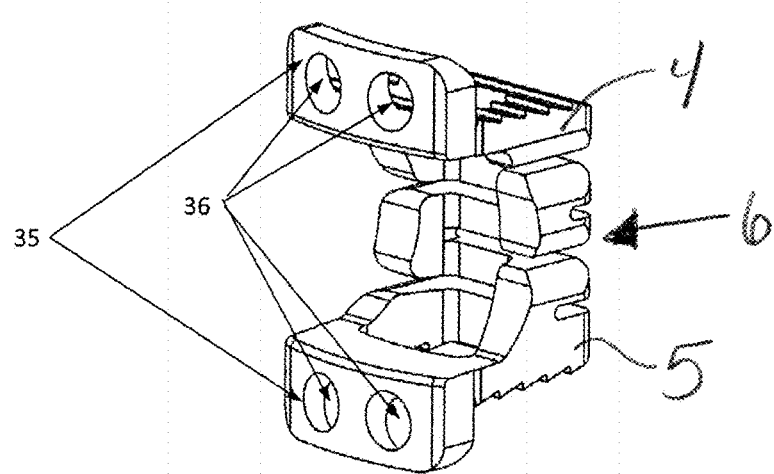
FIG. 31 is a perspective view of another interbody spacer, in accordance with an aspect of the present disclosure.
Figure 32:
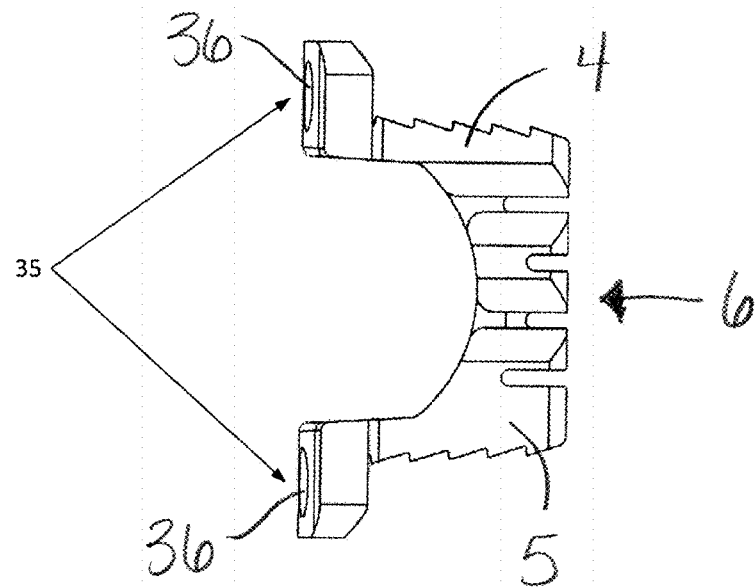
FIG. 32 is a first side view of the interbody spacer of FIG. 31, in accordance with an aspect of the present disclosure.
Figure 33:
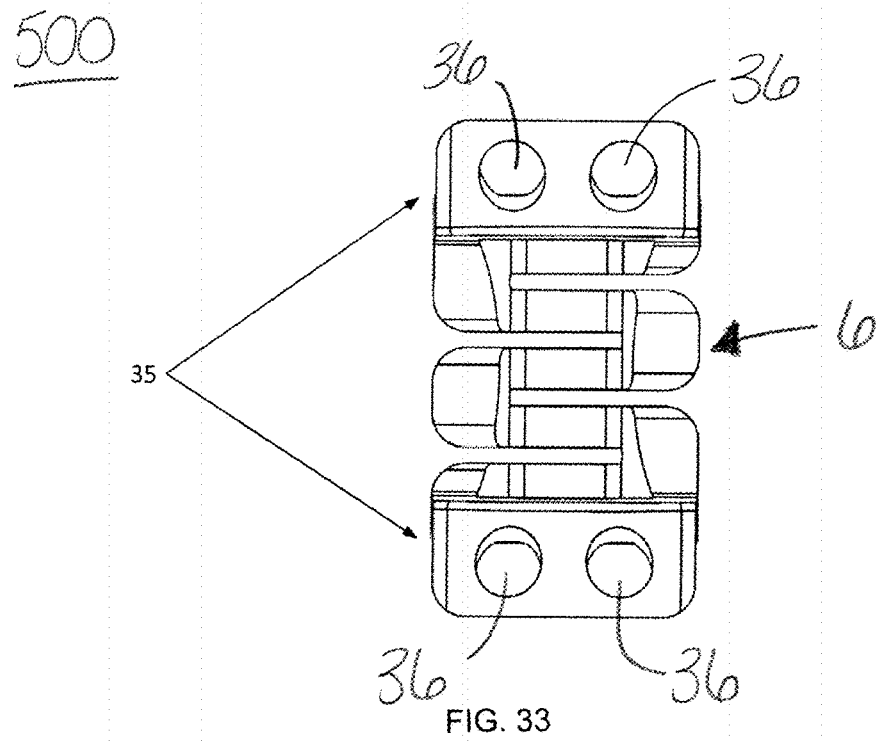
FIG. 33 is a first end view of the interbody spacer of FIG. 31, in accordance with an aspect of the present disclosure.

As discussed in greater detail above, interbody cages are typically used in conjunction with supplemental fixation, such as plates, screws, and rods. Alternatively, cages may contain features to directly provide supplemental fixation. These devices are typically termed all-in-one cages or plate-cage devices. FIGS. 31-37 depict various embodiments of all-in-one cages, for example, implants 500, 550, 600. FIGS. 31-33 show a corpectomy cage 500 with tabs 35 located at the anterior portion of the superior and inferior endplates 4, 5. The tabs 35 each extend away from an endplate 4, 5 in a generally perpendicular direction, as shown in FIG. 32. Each tab 35 contains at least one aperture 36, which accommodates a screw, pin, other fixation device, or the like as known by one of ordinary skill in the art, that can be inserted directly into the adjacent vertebral bodies 2, 3. As shown, the tabs 35 include two apertures 36 in each tab 35; however, it is understood that the tabs 35 may contain any number of apertures 36, including zero. It is also understood that the device 500 may contain features to prevent the screws from backing out. These anti-backout features may be made of, for example, lips, interference fits, or a separate component that prevents the screws from backing out while in the patient. The tabs 35 may also contain an integral fixation feature (not shown), such as a pin or nail that is directly attached to the posterior side of the tab 35. This feature may penetrate the cortex of the adjacent vertebral bodies during insertion, while not requiring any additional steps or multiple components.

Figure 34:
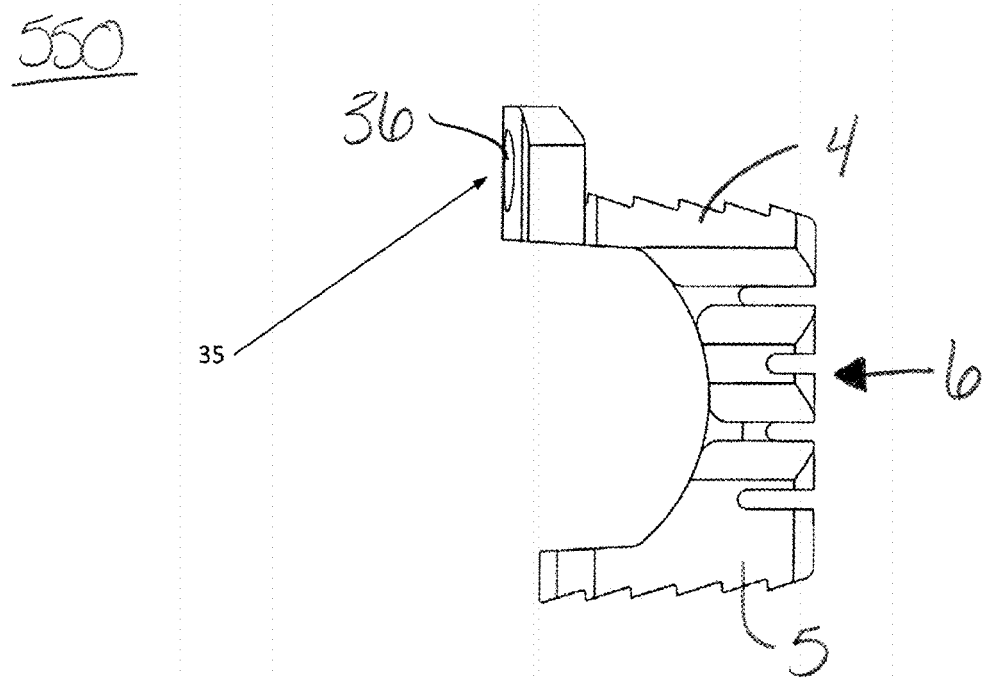
FIG. 34 is a first side view of another interbody spacer, in accordance with an aspect of the present disclosure.
Figure 35:
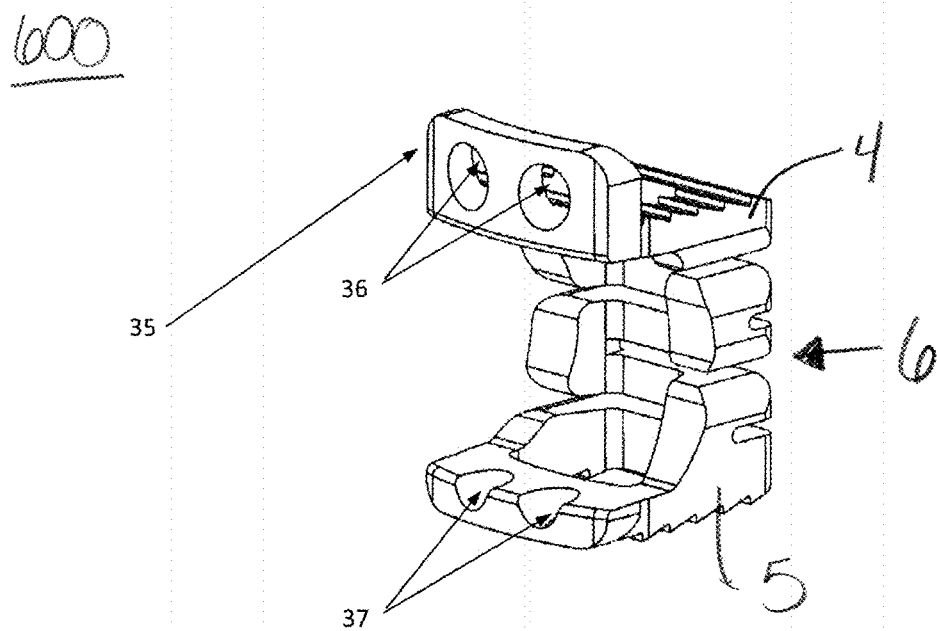
FIG. 35 is a perspective view of a further interbody spacer, in accordance with an aspect of the present disclosure.
Figure 36:
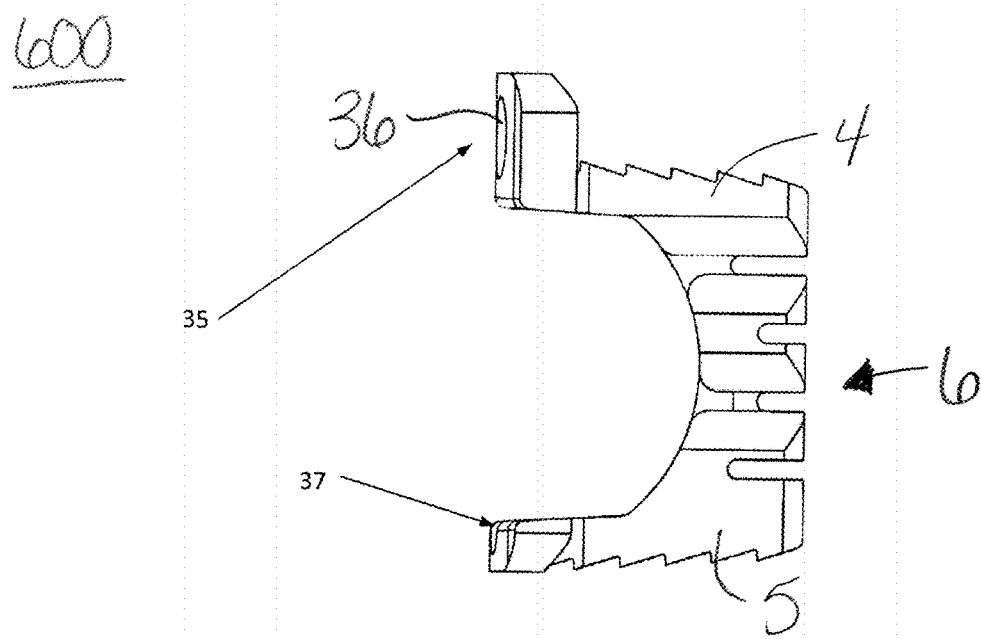
FIG. 36 is a first side view of the interbody spacer of FIG. 35, in accordance with an aspect of the present disclosure.
Figure 37:
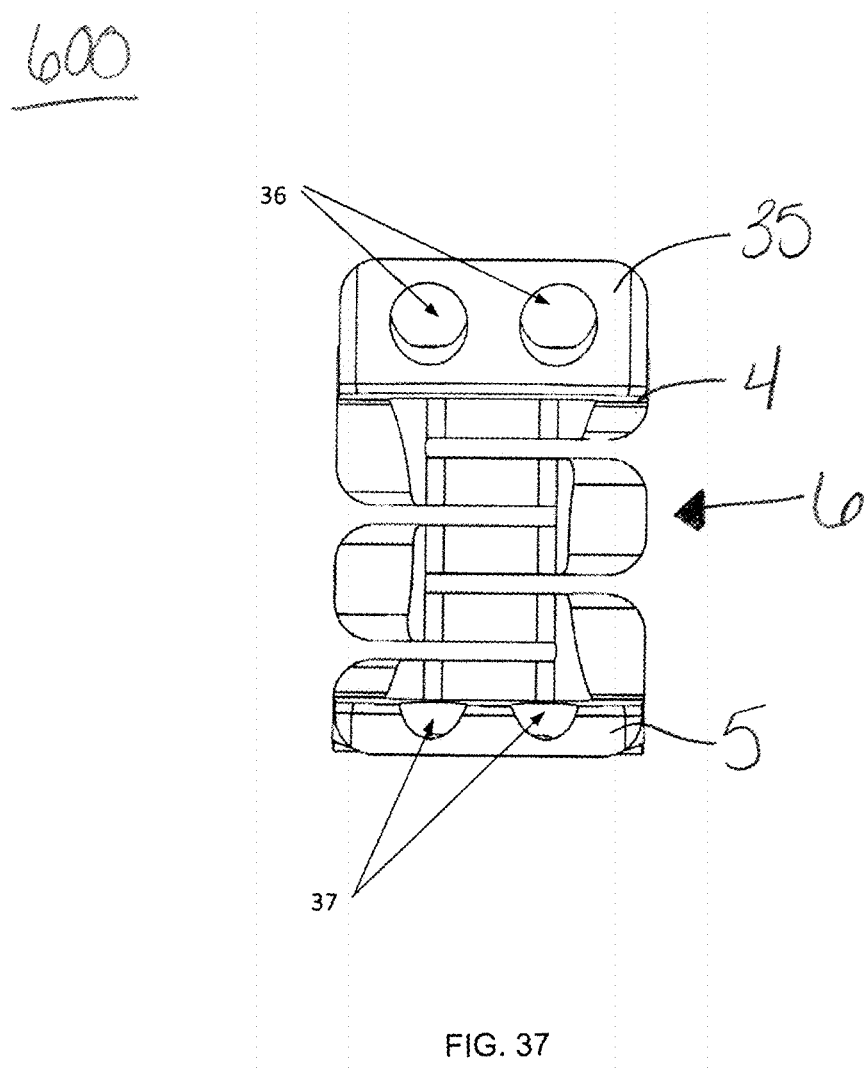
FIG. 37 is a first end view of the interbody spacer of FIG. 35, in accordance with an aspect of the present disclosure.

FIG. 34 depicts the implant 550 which includes only one tab 35 and apertures 36 extending through that one tab 35. Although the implant 550 shows the tab 35 extending generally perpendicularly away from the superior endplate 4, it is also contemplated that the implant 550 could instead have a tab 35 extending generally perpendicularly away from the inferior endplate 5. Another implant 600 is shown in FIGS. 35-37. The implant 600 includes only one tab 35 extending generally perpendicularly away from the superior endplate 4 with at least one aperture 36 extending through the tab 35. The implant 600 may also include at least one aperture 37 extending directly through the inferior endplate 5. The at least one aperture 37 may be, for example, two apertures 37 as shown in FIG. 35, although alternative numbers of apertures 37 are also contemplated. Positioning the apertures 37 to extend directly through the endplate 5 allows for the inferior end of the implant 600 not to have anterior profile that may irritate soft tissue that is located adjacent to the vertebral body. An alternative embodiment (not shown) may not include tabs at either the superior or inferior end, but the alternative embodiment may include apertures 37 that extend directly through both the superior and inferior endplates 4, 5. The apertures 37 may accommodate screws, pins, or other fixation components. It is understood by one of ordinary skill in the art that the implants 500, 550, 600 are depicted with the superior endplate 4 on the top, but the implants 500, 550, 600 may be rotated such that the superior endplate 4 is on the bottom. This may facilitate easier insertion of screws, particularly in embodiments that contain only one tab 35.

Figure 38:
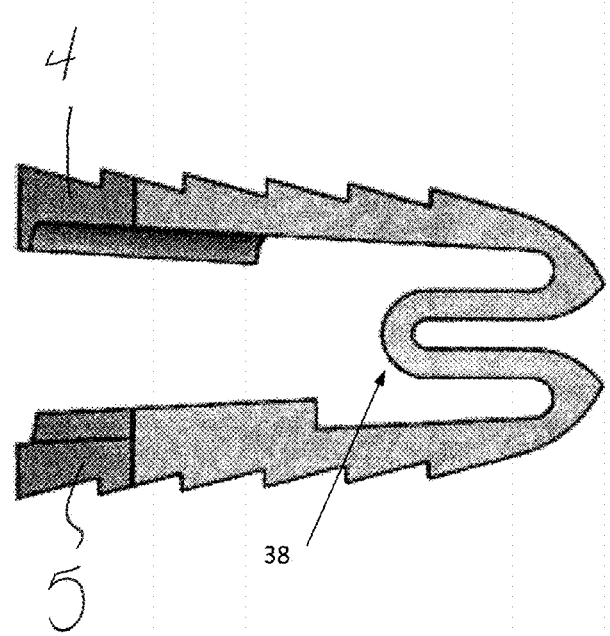
FIG. 38 is a first side view of another interbody spacer, in accordance with an aspect of the present disclosure.
Figure 39:
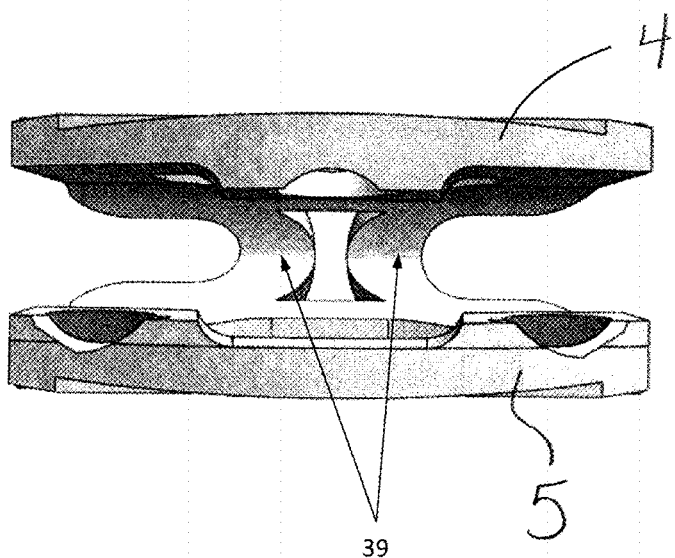
FIG. 39 is a first end view of a further interbody spacer, in accordance with an aspect of the present disclosure.

Referring now to FIG. 38, another implant 650 is shown. The implant 650 may include a first or superior endplate 4, a second or inferior endplate 5, and one or more connecting members 38. The connecting members 38 may have a serpentine shape that is oriented substantially in the sagittal plane. In another embodiment, as depicted in the posterior view in FIG. 39, another implant 700 is shown. The implant 700 may include multiple connecting members 39 extending between a first or superior endplate 4 and a second or inferior endplate 5. The connecting members 39 may be, for example, serpentine in shape and are oriented substantially in the coronal plane. It is also contemplated that the connecting members 38, 39 may be oriented in other planes or combinations thereof. For example, the connecting members 38, 39 in FIGS. 38 and 39 may be oriented in an oblique plane, 45 degrees from the sagittal and coronal planes. It is also understood that the radii of curvatures in the connecting members 38, 39 may vary to facilitate a desired amount of compliance, as would be known by one of ordinary skill in the art.

Figure 40:
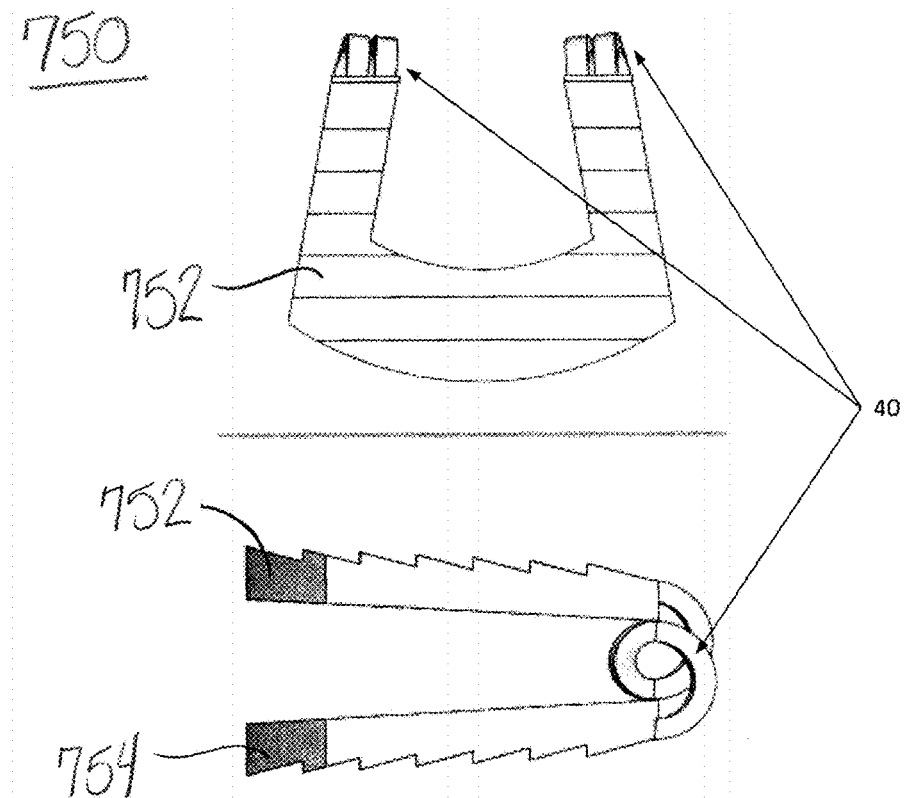
FIG. 40 is a top view and a first side view of another interbody spacer, in accordance with an aspect of the present disclosure.
Figure 41:
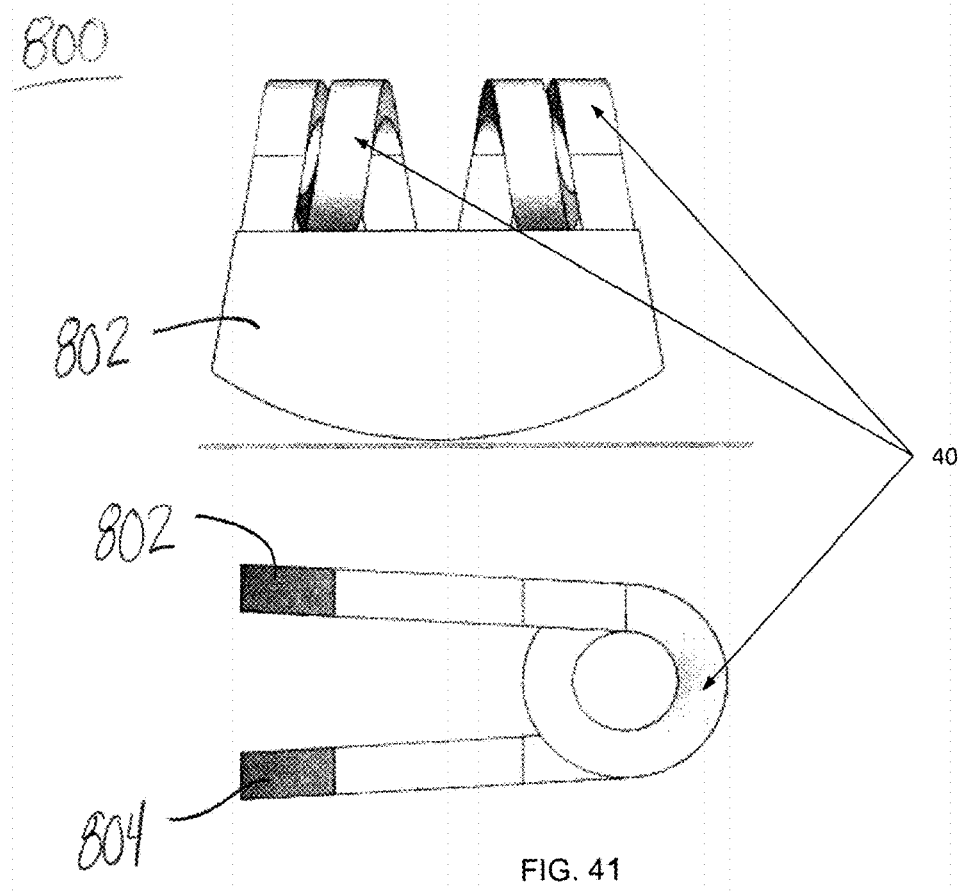
FIG. 41 is a top view and a first side view of yet another interbody spacer, in accordance with an aspect of the present disclosure.
Figure 42:
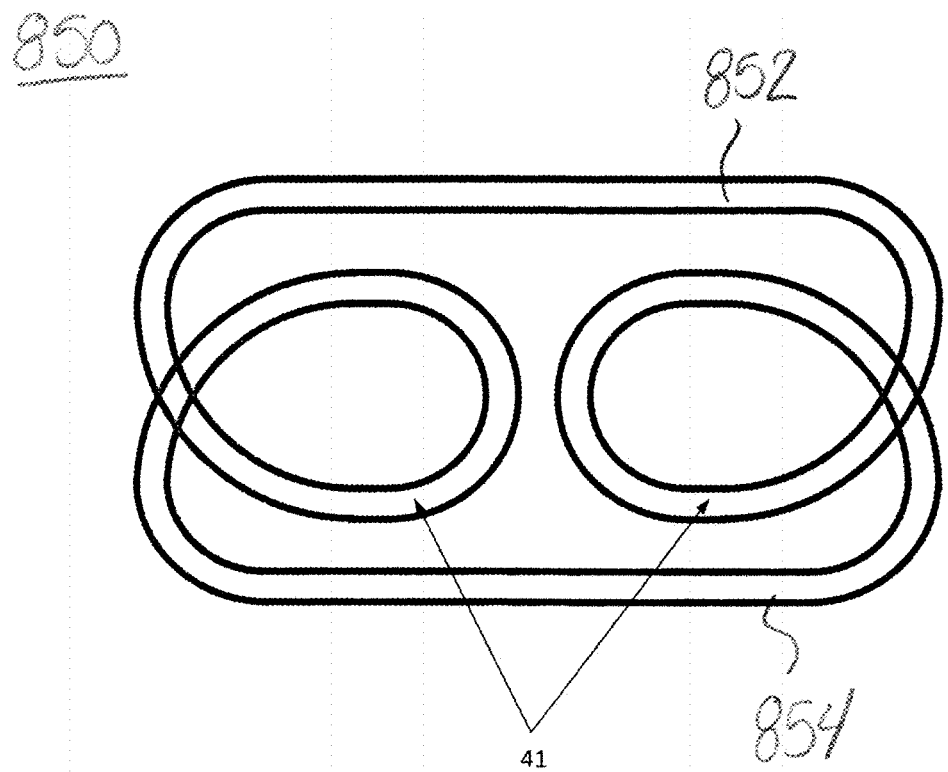
FIG. 42 is a first end view of another interbody spacer, in accordance with an aspect of the present disclosure.
Figure 43:
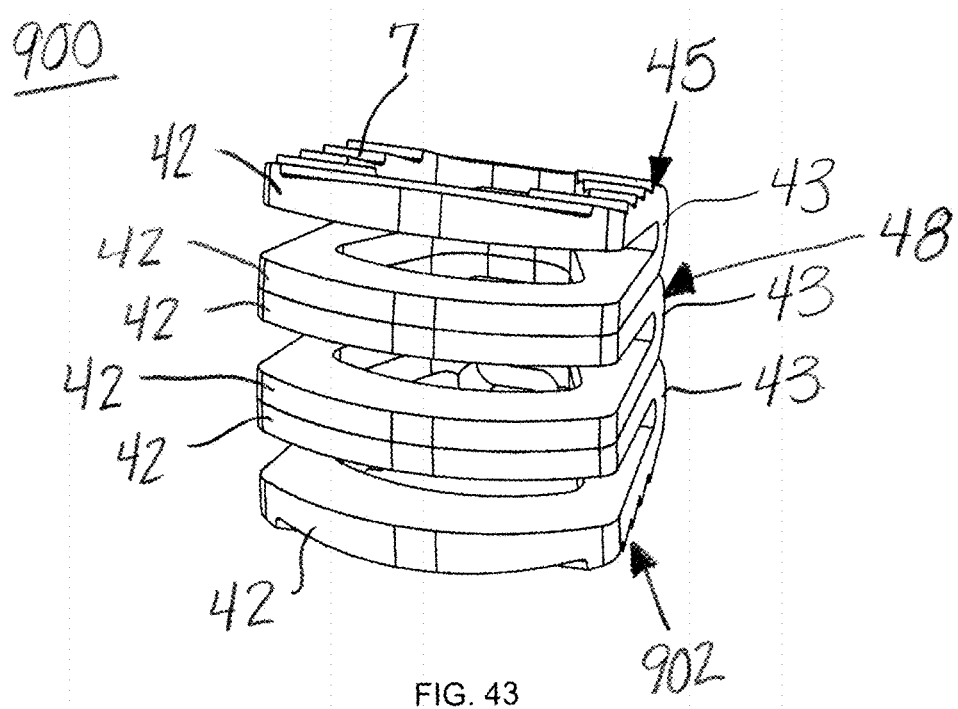
FIG. 43 is a perspective view of a further interbody spacer, in accordance with an aspect of the present disclosure.
Figure 44:
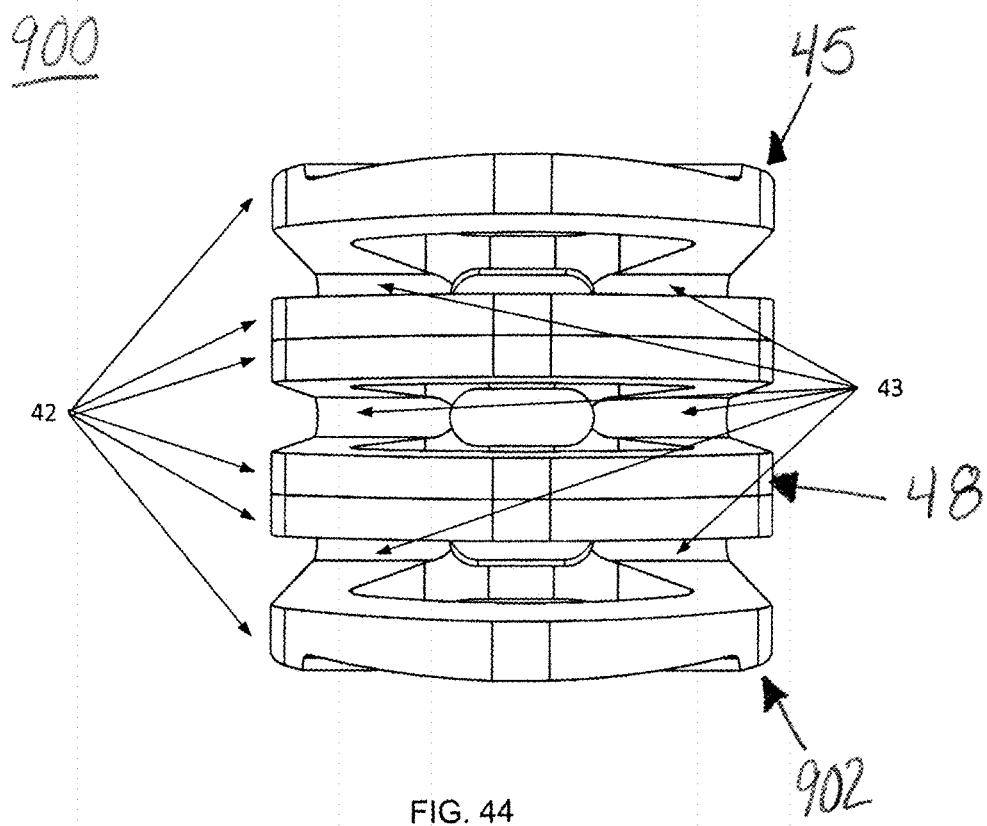
FIG. 44 is an end view of the interbody spacer of FIG. 43, in accordance with an aspect of the present disclosure.

As depicted in the lateral and axial views shown in FIGS. 40 and 41, implants 750, 800 may include at least one connecting members 40 extending between superior endplates 752, 802 and inferior endplates 752, 804. The at least one connecting member 40 may have helical shapes that are oriented substantially in the sagittal plane. In another embodiment, as shown in the posterior view of FIG. 42, the implant 850 may include multiple connecting members 41 positioned between a superior endplate 852 and an inferior endplate 854. The multiple connecting members 41 may have, for example, a helical shape and may be oriented substantially in the coronal plane. It is also understood that the connecting members 40, 41 may be oriented in other planes or combinations thereof. For example, the connecting members 40, 41 shown in FIGS. 40-42 may be oriented in a plane 45 degrees from both the sagittal and coronal planes. It is also understood that the radii of curvatures in the connecting members 40, 41 may vary to facilitate a desired amount of compliance.

In all embodiments described thus far, the corpectomy cages 100, 150, 200, 250, 300, 350, 400, 450, 500, 550, 600, 650, 700, 750, 800, 850 have been monolithic. It is understood that the implants described in greater detail above may include multiple components that are assembled prior to surgery or in situ, such as shown in FIGS. 43-53. The corpectomy cages 900, 950, 1000, 1050, 1100 each may include more than one smaller cage. Each cage includes two endplates 42 and at least one connecting member 43 coupling the two endplates 42 together. The endplates 42 and connecting members 43 may take any of the forms of the any one or more of implants 100, 150, 200, 250, 300, 350, 400, 450, 500, 550, 600, 650, 700, 750, 800, 850 described in greater detail above, which are hereby incorporated by reference here and will not be described again for brevity sake.

Figure 45:
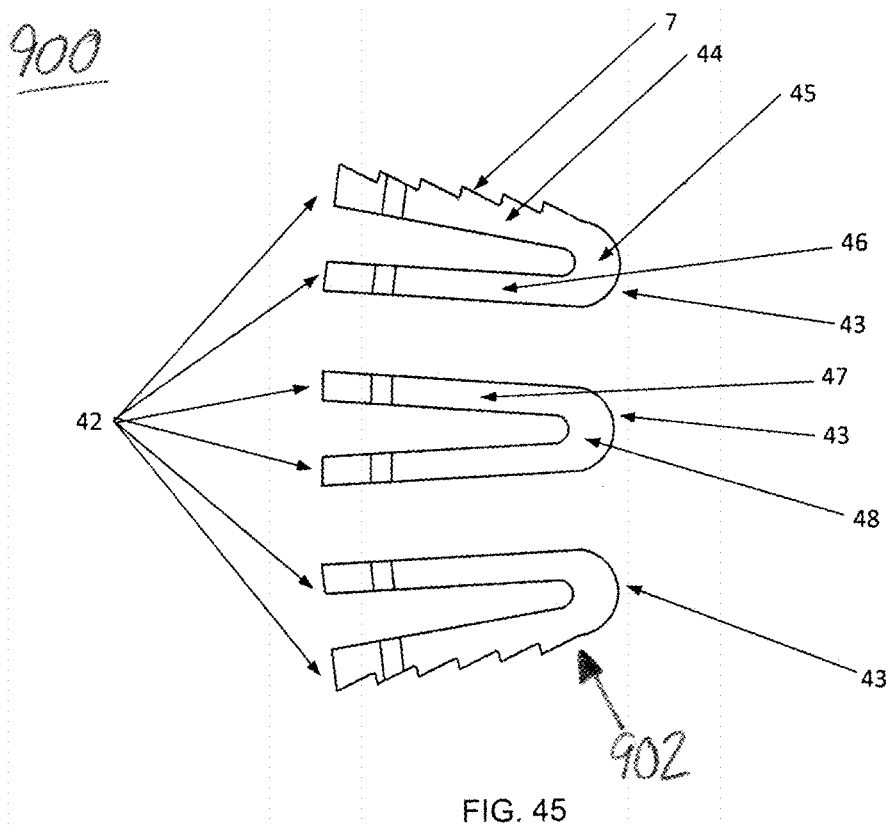
FIG. 45 is an exploded, first side view of the interbody spacer of FIG. 43, in accordance with an aspect of the present disclosure.
Figure 46:
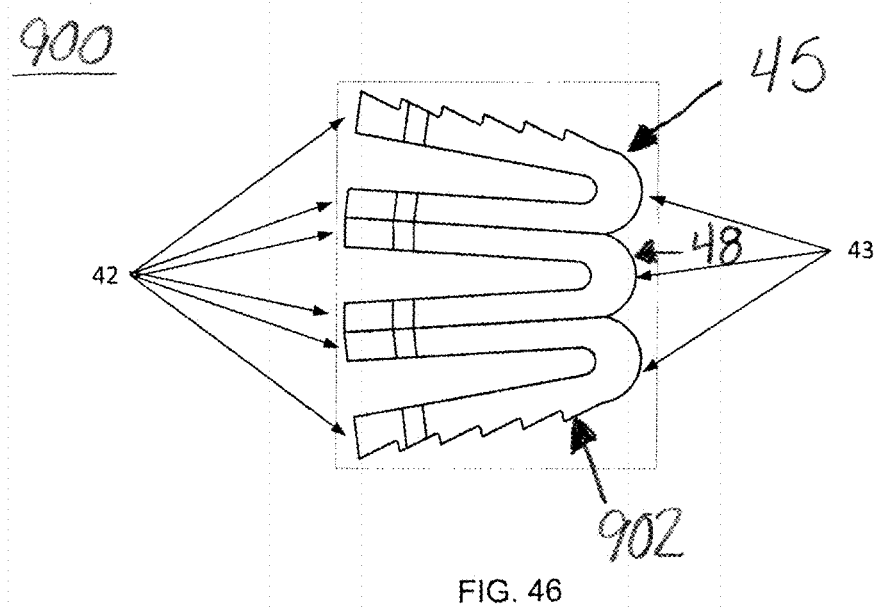
FIG. 46 is an assembled, first side view of the interbody spacer of FIG. 43, in accordance with an aspect of the present disclosure.
Figure 47:
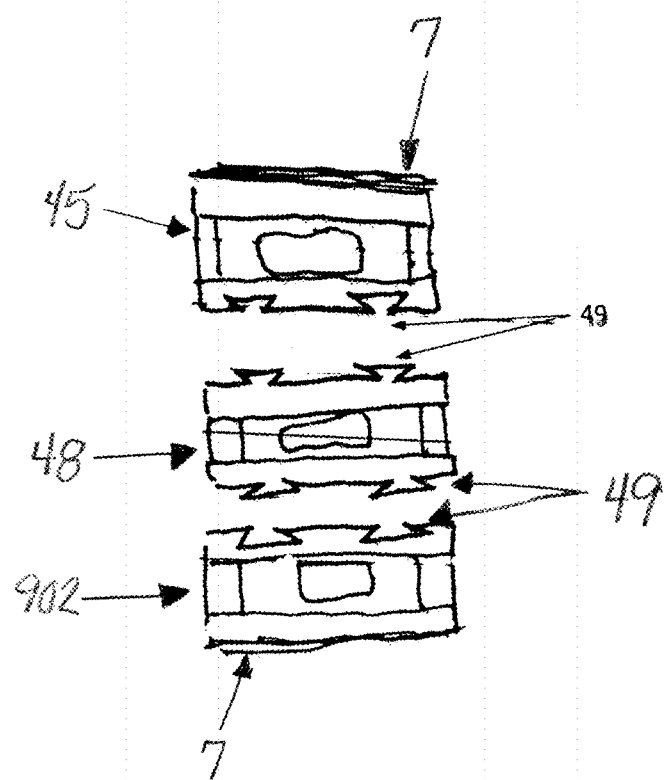
FIG. 47 is an exploded, first end view of another interbody spacer, in accordance with an aspect of the present disclosure.

Referring now to FIGS. 43-46, an implant 900 is shown and includes three smaller cages 45, 48, 902 coupled together to form the implant 900. FIG. 45 shows an exploded view of the three smaller cages 45, 48, 902 of the modular implant or modular device 900 which are coupled together to form the implant 900 as shown in FIG. 46. As shown, upper cage 45 may include an upper endplate 42 on the superior end 44 of the cage 45 and a lower endplate 42 on the inferior end 46 of the cage 45. The upper endplate 42 of the upper cage 45 may include teeth 7 that improve connection with the adjacent vertebra. The lower endplate 42 on the inferior end 46 of the upper cage 45 may include a shape and geometry that mates with the upper endplate 42 on the superior end 47 of an adjacent cage 48. It is understood that the mating surfaces of adjacent cages 45, 48, 902 may not include teeth 7 for mating with vertebral bodies but include connecting features that allow for fixation between the adjacent cages 45, 48, 902. The connecting features may include, for example, dovetails 49, as depicted in FIG. 47, tongue-and-groove, press-fit, and the like as known by one of ordinary skill in the art.

Figure 48:
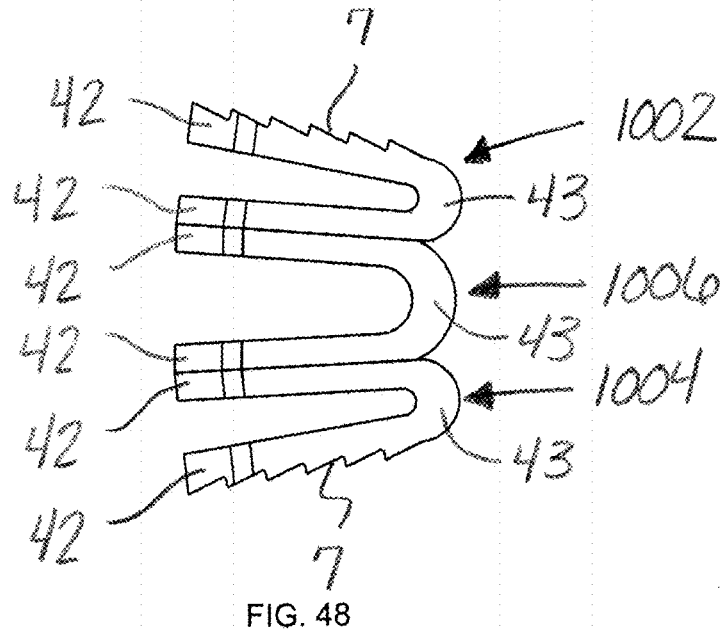
FIG. 48 is a first side view of another interbody spacer, in accordance with an aspect of the present disclosure.
Figure 51:
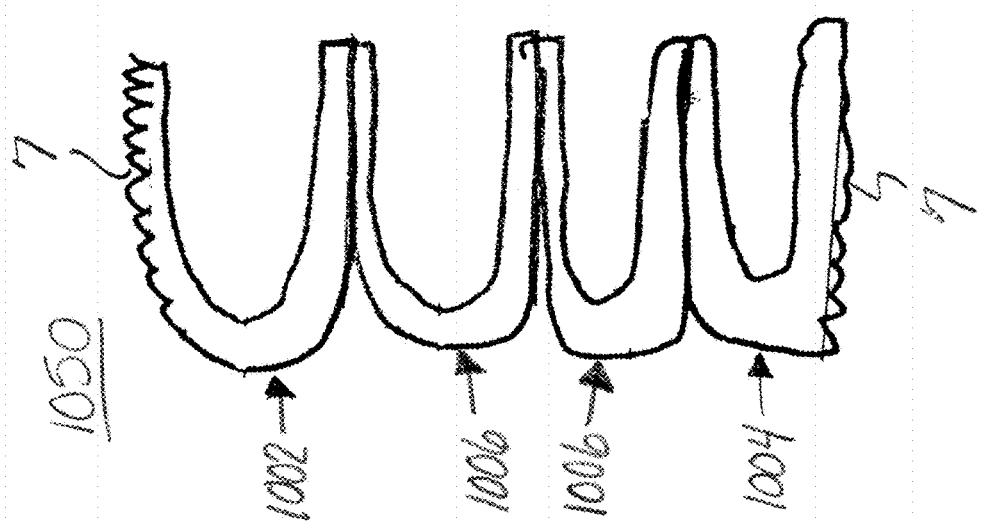
FIG. 51 is a second side view of a third embodiment of the interbody spacer of FIG. 49, in accordance with an aspect of the present disclosure.
Figure 50:
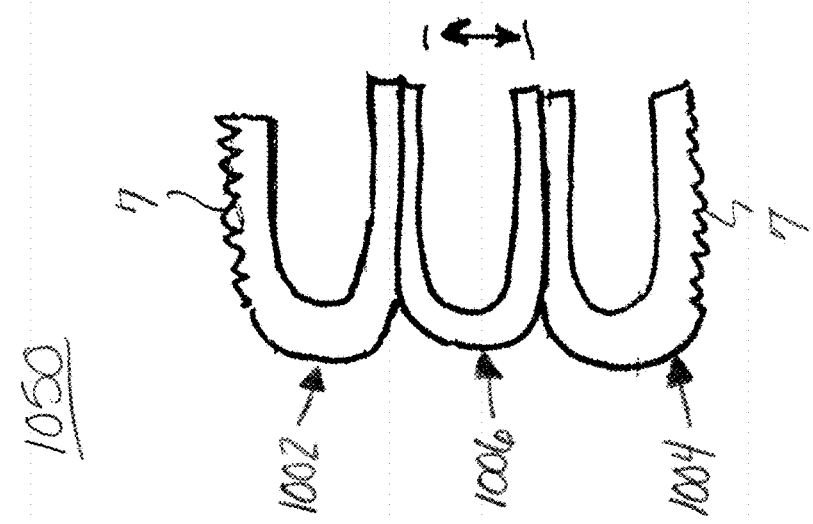
FIG. 50 is a second side view of a second embodiment of the interbody spacer of FIG. 49, in accordance with an aspect of the present disclosure.
Figure 49:
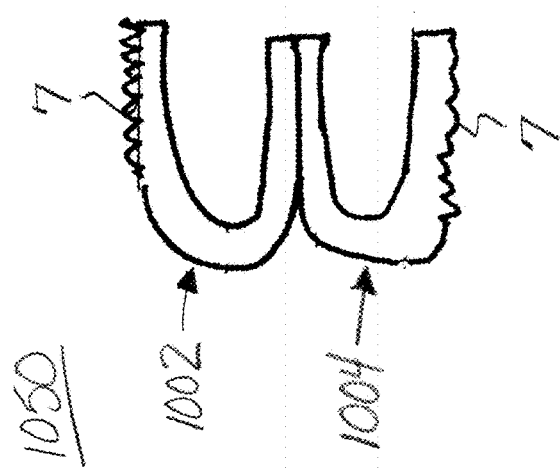
FIG. 49 is a second side view of a first embodiment of an interbody spacer, in accordance with an aspect of the present disclosure.

The corpectomy cages may come in different sizes, as such, the upper cage 1002, lower cage 1004, and middle cage 1006 may have varying heights, such as shown in FIG. 48. It is recognized that a collection of cages 1002, 1004, 1006 with varying heights may be supplied during a surgical procedure, such than any assortment of total construct heights can be assembled. It is also recognized that the construct does not need to be required of three cages 1002, 1004, 1006 but may include two or more cages 1002, 1004, 1006, as shown in FIGS. 49-51. During a surgical procedure, bone graft material may be inserted into the cage, for example, prior to insertion or in situ.

Figure 52:
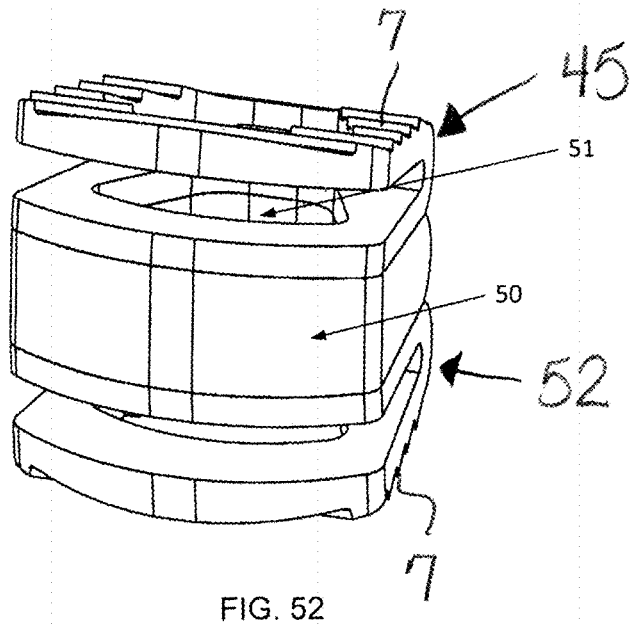
FIG. 52 is a perspective view of another interbody spacer, in accordance with an aspect of the present disclosure.
Figure 53:
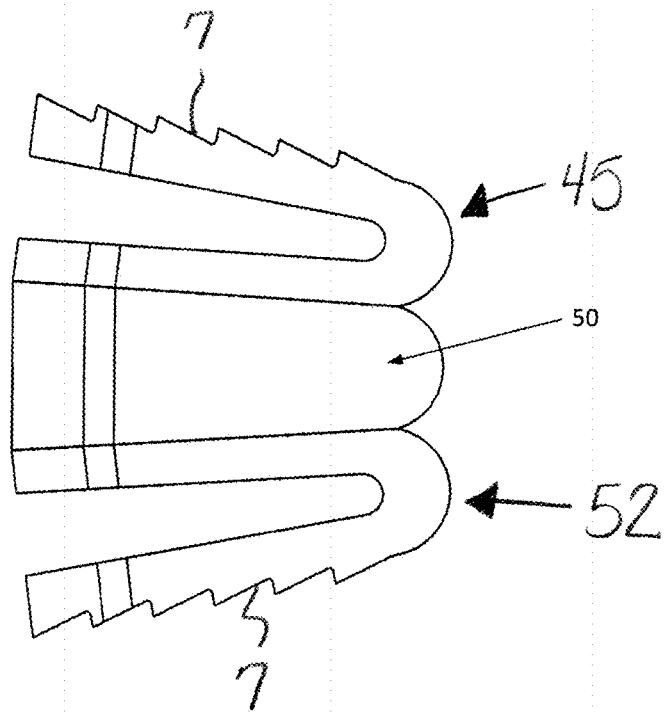
FIG. 53 is a first side view of the interbody spacer of FIG. 52, in accordance with an aspect of the present disclosure.

Referring now to FIGS. 52 and 53, another implant or cage 1100 is shown. The cage 1100 may include an upper cage 45, a lower cage 52, and at least one intermediate cage 50 coupled to an inferior side of the upper cage 45 and a superior side of the lower cage 52. The intermediate cage(s) 50 may include, for example, a block of material with or without an aperture 51 that can accommodate bone graft material, as shown in FIG. 52. The block of material may be, for example, a rigid material or a compliant material, such as an elastomer or polymer.

In the embodiments described in FIGS. 43-53, it is understood that the modular device 900, 950, 1000, 1050, 1100 may be assembled, for example, prior to insertion or in situ. It is also understood that there may be additional benefits to assembling the device in situ, such as it being more minimally invasive. A second benefit may be that the device may provide relative displacement between the endplates of the vertebral bodies if it were assembled in situ. In this example, the surgical method may include, for example, the upper most and lower most cages being inserted into position against their respective vertebral bodies. One or more slightly oversized intermediate cages may then be positioned between the upper and lower cages. When the intermediate cage(s) are inserted, it would cause the relative distance between the upper and lower vertebral bodies to increase. This may lead to decompression of adjacent soft tissue.

Referring now to FIGS. 54-59, an implant 1150 is shown. The implant 1150 may include a first or superior endplate 1152, a second or inferior endplate 1162, and a connecting member 1172 coupling the superior endplate 1152 to the inferior endplate 1162. The superior endplate 1152 may include a top or superior surface 1154 opposite a bottom or inferior surface 1156. The top surface 1154 may include a surface texture 1158, such as, teeth as shown in FIGS. 54-59 or alternative roughened or porous surfaces as known by one of ordinary skill in the art. The superior endplate 1152 may also include a through hole 1160 extending through the endplate 1152 from the superior surface 1154 to the inferior surface 1156. The shape of the through hole 1160 may be as described above with reference to the aperture 13, which will not be described again here for brevity sake.

With continued reference to FIGS. 54-59, the inferior endplate 1162 may include a top or superior surface 1164 opposite a bottom or inferior surface 1166. The bottom surface 1166 may include a surface texture 1168, such as, teeth as shown in FIGS. 54-59 or alternative roughened or porous surfaces as known by one of ordinary skill in the art. The inferior endplate 1162 may also include a through hole 1170 extending through the endplate 1162 from the superior surface 1164 to the inferior surface 1166. The shape of the through hole 1170 may be as described above with reference to the aperture 13, which will not be described again here for brevity sake. The through hole 1170 in the endplate 1162 may be positioned to align with the through hole 1160 in the endplate 1152 to allow for bone grafts to be inserted into the implant 1150.

The connecting member 1172 may include a posterior side 1174, a first lateral side 1176 extending away from a first end of the posterior side 1174, and a second lateral side 1178 extending away from a second end of the posterior side 1174. The posterior side 1174 may include at least one first vertical member 1180 extending away from the inferior surface 1156 of the superior endplate 1152 and at least one second vertical member 1182 extending away from the superior surface 1164 of the inferior endplate 1162.

Figure 54:
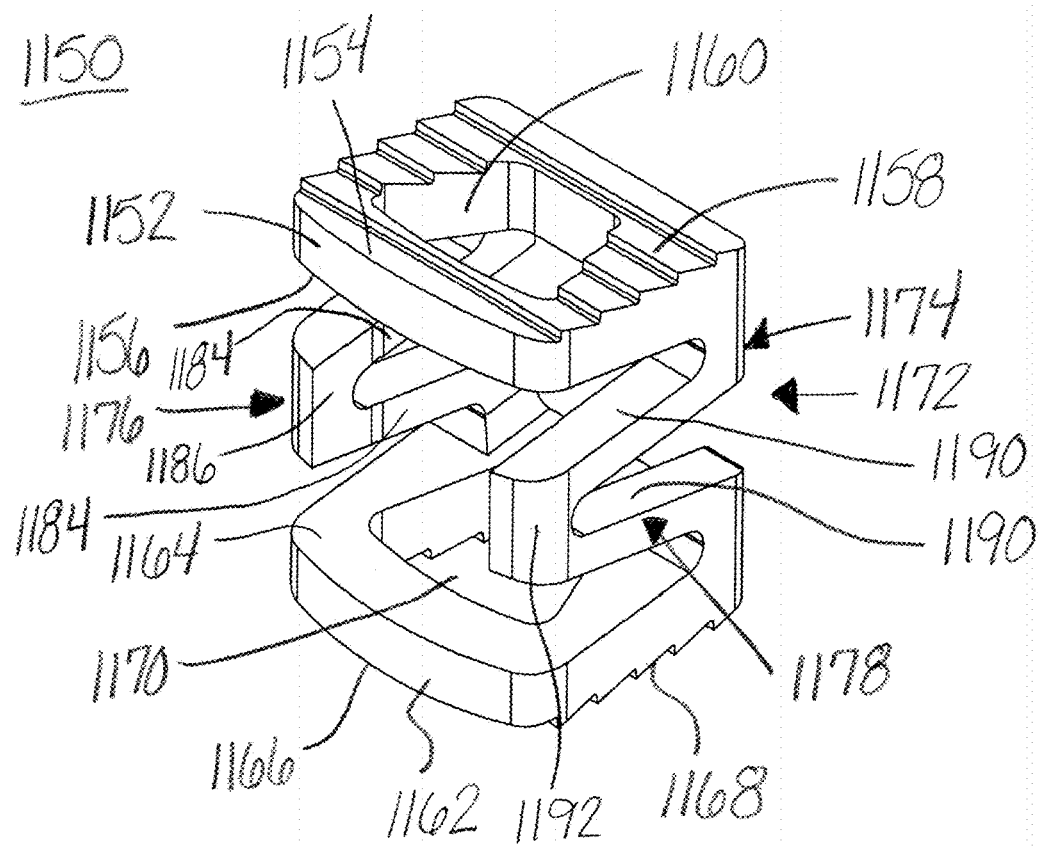
FIG. 54 is a first perspective view of another interbody spacer, in accordance with an aspect of the present disclosure.
Figure 55:
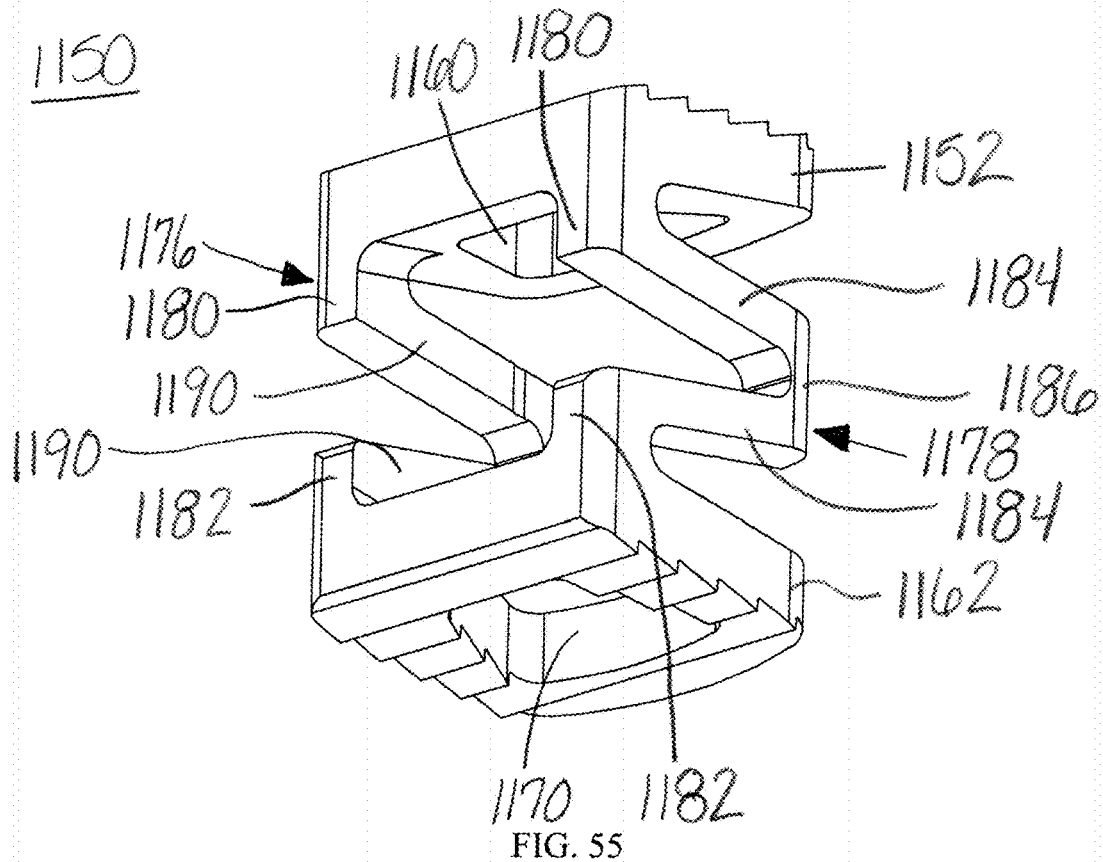
FIG. 55 is a second perspective view of the interbody spacer of FIG. 54, in accordance with an aspect of the present disclosure.
Figure 56:
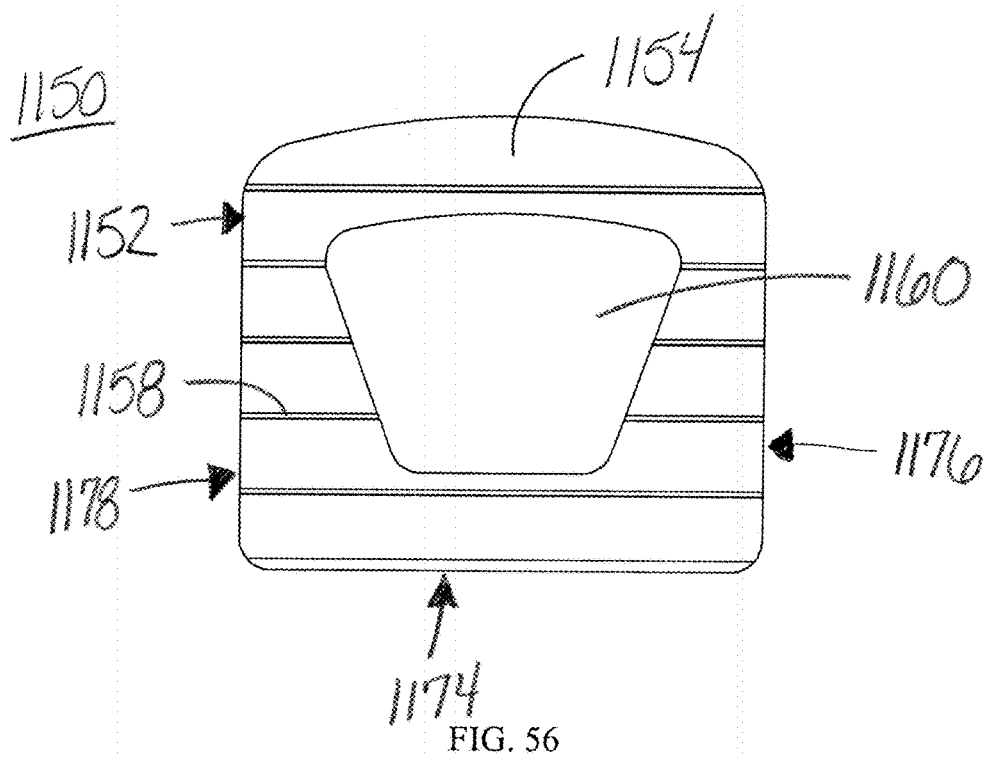
FIG. 56 is a top view of the interbody spacer of FIG. 54, in accordance with an aspect of the present disclosure.
Figure 57:
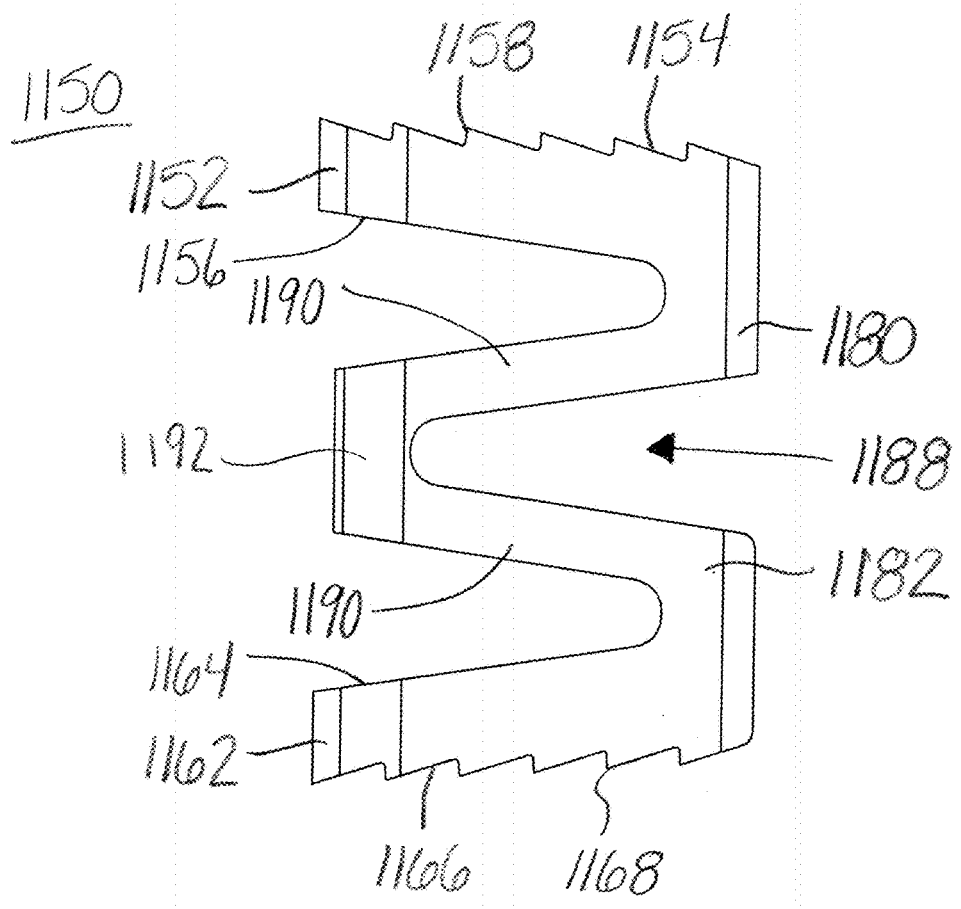
FIG. 57 is a first side view of the interbody spacer of FIG. 54, in accordance with an aspect of the present disclosure.
Figure 58:
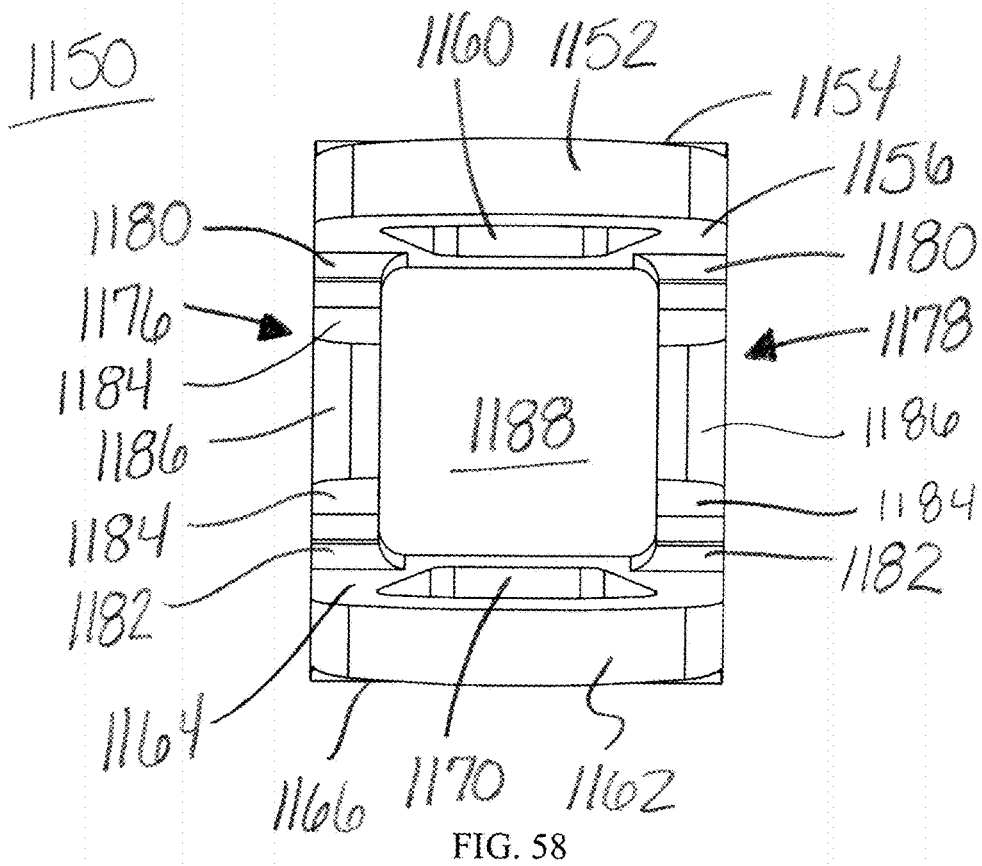
FIG. 58 is a first end view of the interbody spacer of FIG. 54, in accordance with an aspect of the present disclosure.
Figure 59:
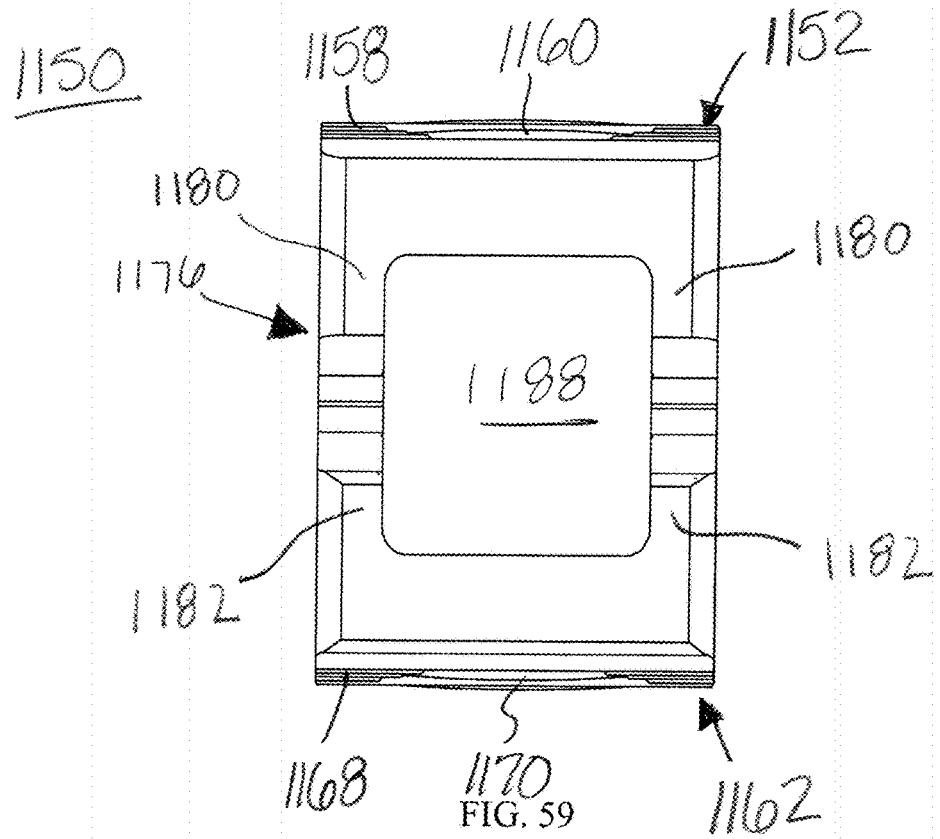
FIG. 59 is a second end view of the interbody spacer of FIG. 54, in accordance with an aspect of the present disclosure.
Figure 60:
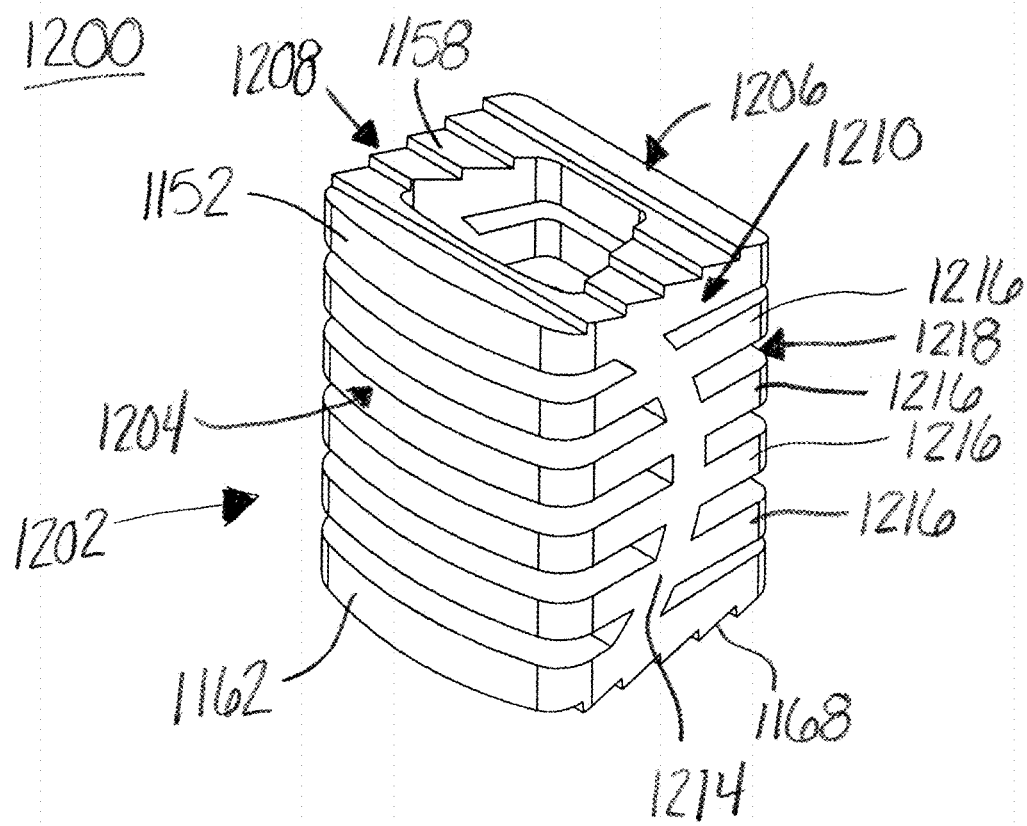
FIG. 60 is a first perspective view of another interbody spacer, in accordance with an aspect of the present disclosure.
Figure 61:
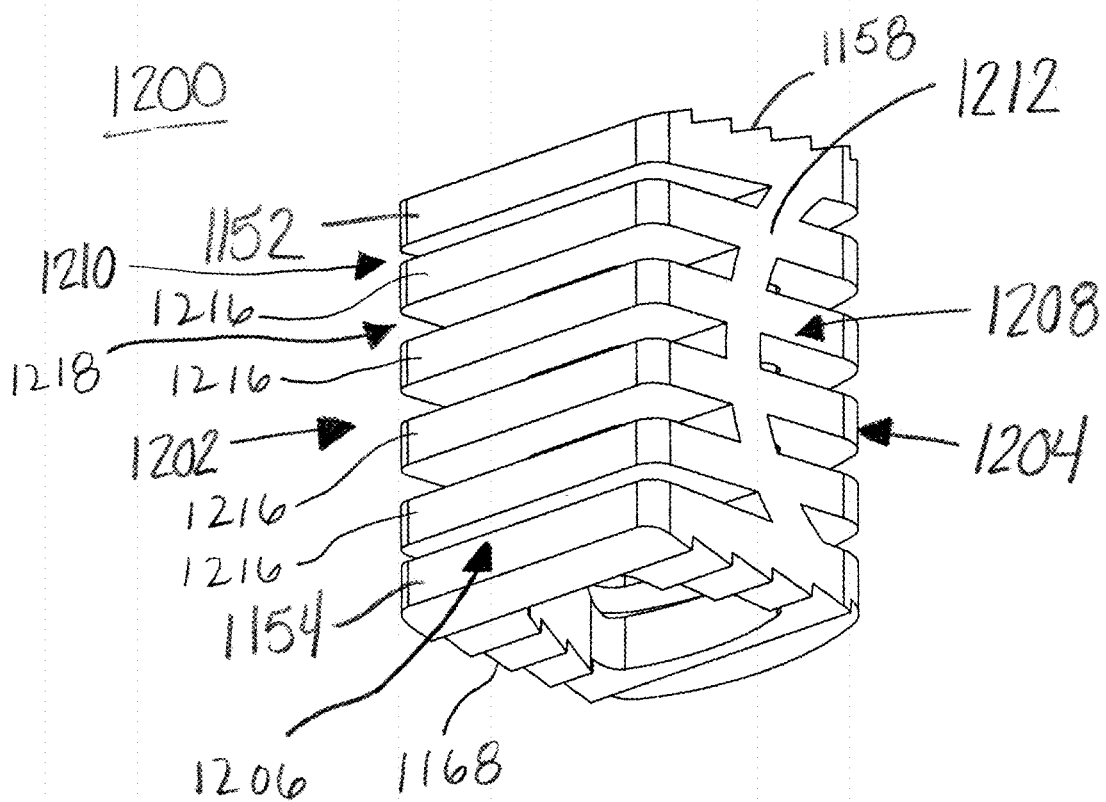
FIG. 61 is a second perspective view of the interbody spacer of FIG. 60, in accordance with an aspect of the present disclosure.
Figure 62:
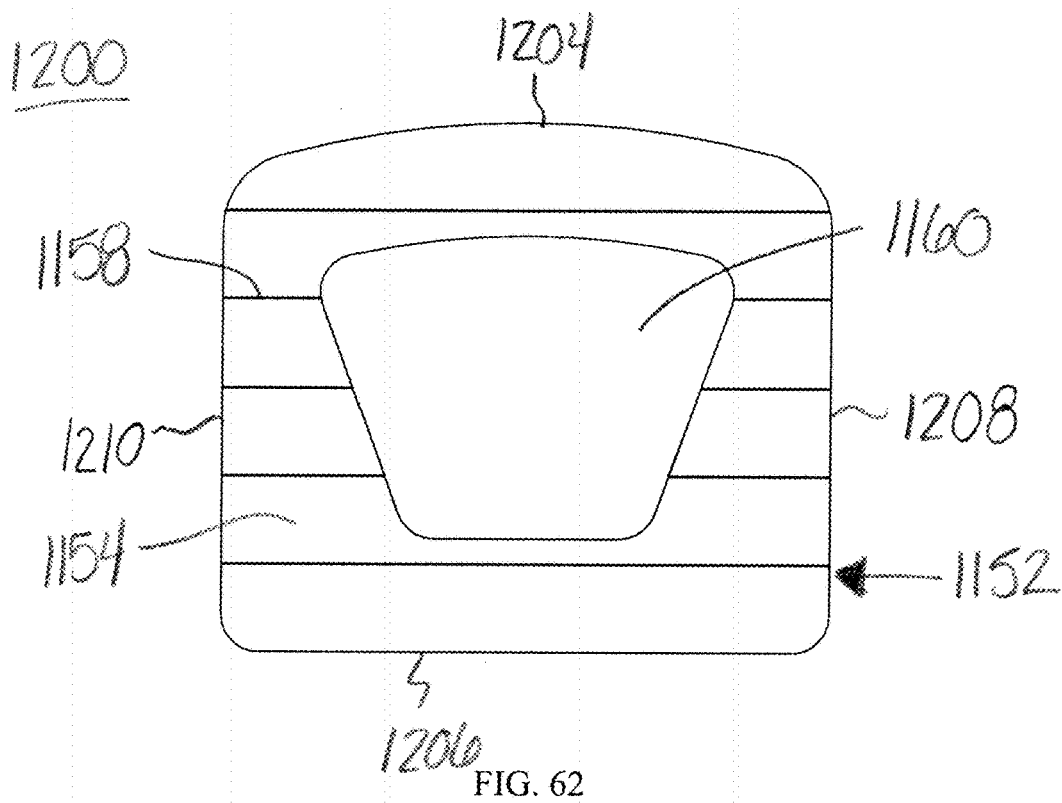
FIG. 62 is a top view of the interbody spacer of FIG. 60, in accordance with an aspect of the present disclosure.
Figure 63:
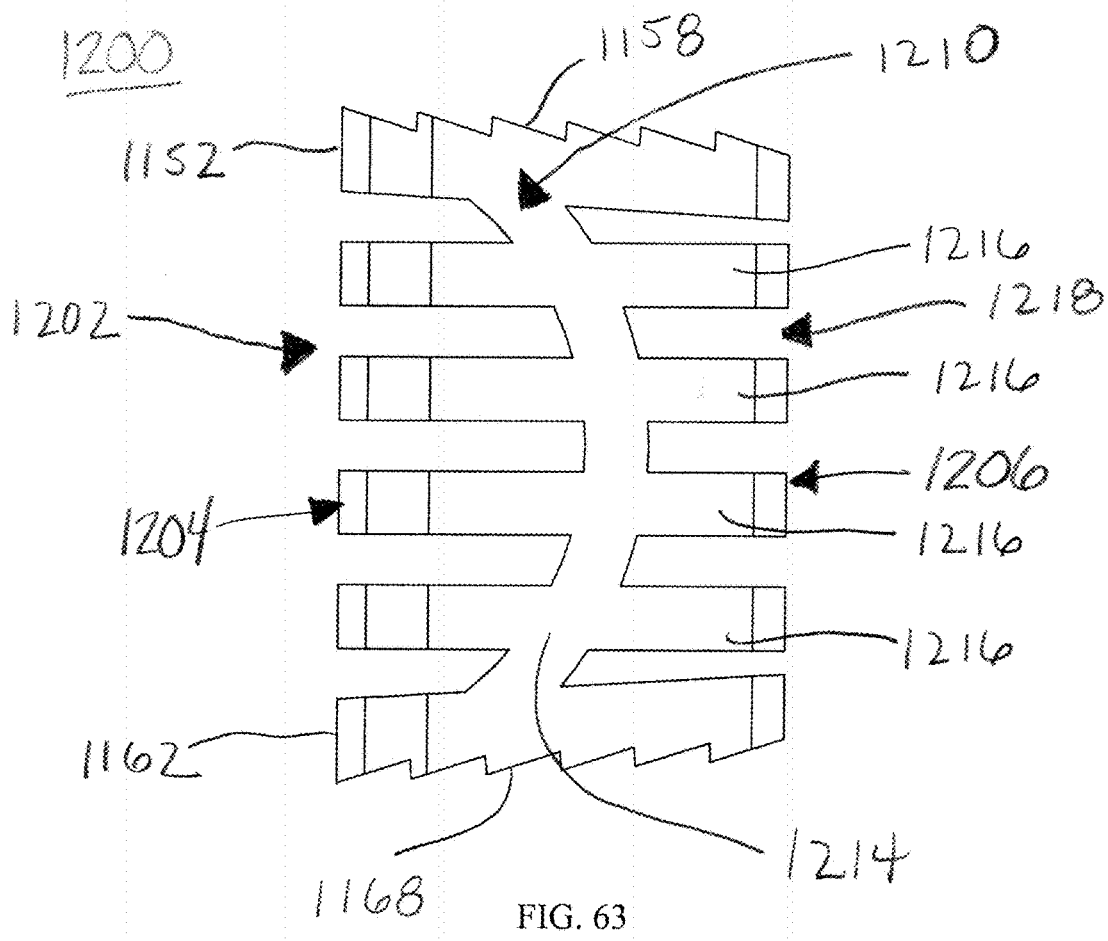
FIG. 63 is a first side view of the interbody spacer of FIG. 60, in accordance with an aspect of the present disclosure.
Figure 64:
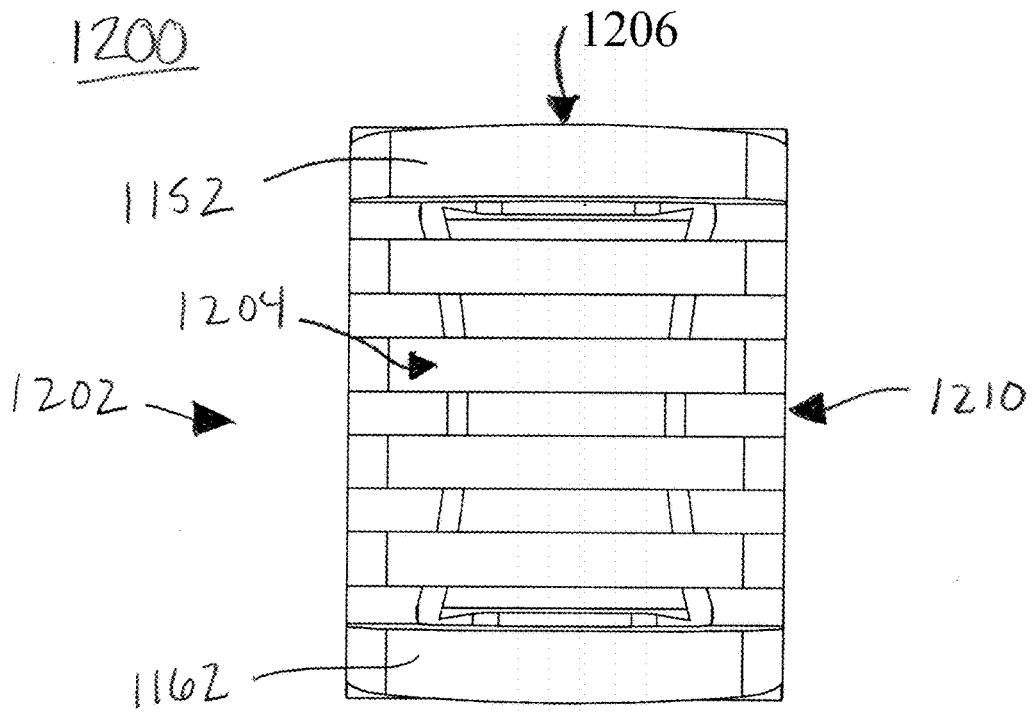
FIG. 64 is a first end view of the interbody spacer of FIG. 60, in accordance with an aspect of the present disclosure.
Figure 65:
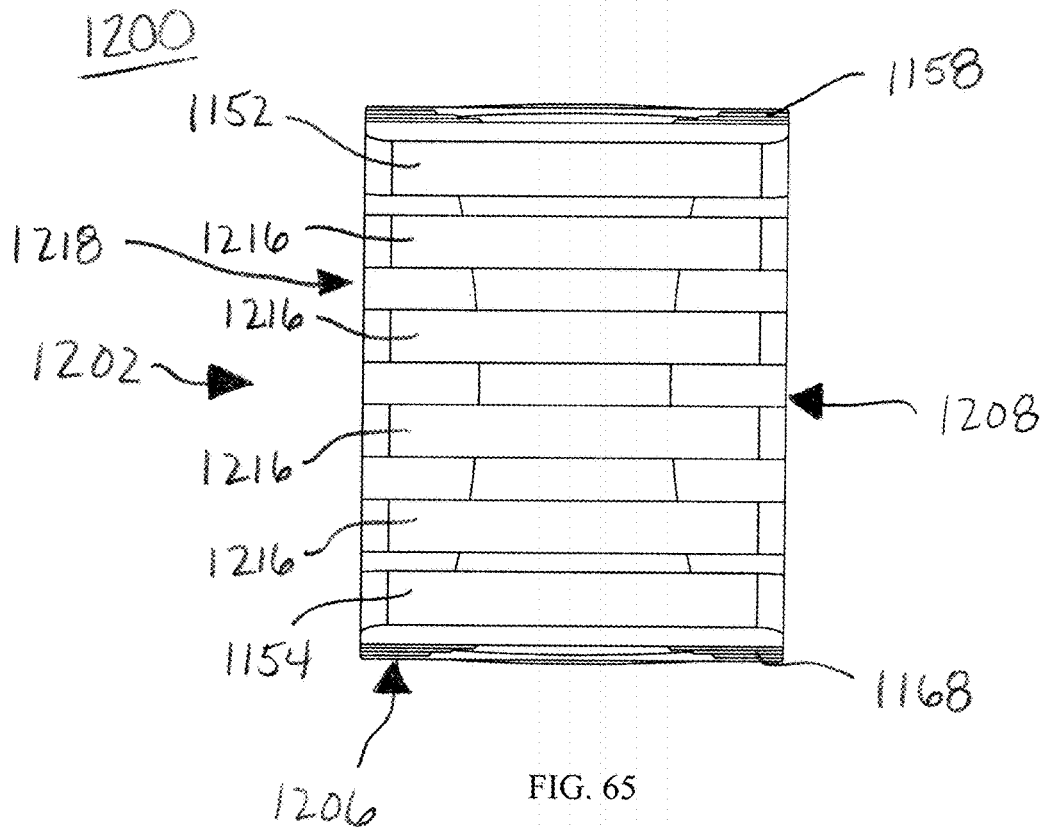
FIG. 65 is a second end view of the interbody spacer of FIG. 60, in accordance with an aspect of the present disclosure.

As shown in FIGS. 54, 55, and 58, the first lateral side 1176 may include first horizontal members, lateral members or straight members 1184 and at least one lateral vertical member, longitudinal members or curved members 1186. The horizontal members 1184 may extend away from each of the first and second vertical members 1180, 1182 on an angle from the posterior side 1174 of the connecting member 1172 toward an open anterior side of the connecting member 1172. The horizontal members 1184 may be coupled on a second end by the at least one lateral vertical member 1186. Although only two horizontal members 1184 and one lateral vertical member 1186 are shown on the first lateral side 1176, it is also contemplated that the first lateral side 1176 may include multiple sets of horizontal members 1184 and lateral vertical members 1186 positioned in, for example, a serpentine or zig-zag orientation between the first endplate 1152 and the second endplate 1162. As shown, the horizontal members 1184 may extend, for example, entirely between the anterior and posterior sides of the endplates 1152, 1162. Alternative lengths of the horizontal members 1184 are also contemplated, for example, the horizontal members 1184 may extend away from the vertical members 1180, 1182 positioned at the posterior side 1174 of the connecting member 1172 into an opening or cavity 1188 between the endplates 1152, 1162 to any length between the vertical members 1180, 1182 and the anterior front surface of the implant 1150.

As shown in FIGS. 54, 55, 57, and 58, the second lateral side 1178 may include second horizontal members, lateral members or straight members 1190 and at least one lateral vertical member, longitudinal member or curved member 1192. The horizontal members 1190 may extend away from each of the first and second vertical members 1180, 1182 on an angle from the posterior side 1174 of the connecting member 1172 toward an open anterior side of the connecting member 1172. The horizontal members 1190 may be coupled on a second end by the at least one lateral vertical member 1192. Although only two horizontal members 1190 and one lateral vertical member 1192 are shown on the second lateral side 1178, it is also contemplated that the second lateral side 1178 may include multiple sets of horizontal members 1190 and lateral vertical members 1192 positioned in, for example, a serpentine or zig-zag orientation between the first endplate 1152 and the second endplate 1162. As shown, the horizontal members 1190 may extend, for example, entirely between the anterior and posterior sides of the endplates 1152, 1162. Alternative lengths of the horizontal members 1190 are also contemplated, for example, the horizontal members 1190 may extend away from the vertical members 1180, 1182 positioned at the posterior side 1174 of the connecting member 1172 into an opening or cavity 1188 between the endplates 1152, 1162 to any length between the vertical members 1180, 1182 and the anterior front surface of the implant 1150.

Another implant 1200 is shown in FIGS. 60-65. The implant 1200 may include a first or superior endplate 1152, a second or inferior endplate 1162, and a coupling member 1202 positioned between the first endplate 1152 and the second endplate 1162. The first endplate 1152 and the second endplate 1162 are as described above with reference to implant 1150 and will not be described again here for brevity sake. The coupling member 1202 may include a first or anterior side 1204 opposite a posterior side 1206 and a first lateral side or third side 1208 opposite a second lateral side or fourth side 1210. The lateral sides 1208, 1210 may extend between the anterior side 1204 and the posterior side 1206. The coupling member 1202 may form, for example, a generally square or rectangular shape.

With continued reference to FIGS. 60-65, the coupling member 1202 may also include a first lateral connecting member 1212 positioned on a first lateral side 1208 of the coupling member 1202 and a second lateral connecting member 1214 positioned on a second lateral side 1210 of the coupling member 1202. A first end of each lateral connecting member 1212, 1214 may be coupled to the first endplate 1152 and a second end of each lateral connecting member 1212, 1214 may be coupled to the second endplate 1162. The lateral connecting members 1212, 1214 may, for example, curve or arc as they extend between the first endplate 1152 and the second endplate 1154. The coupling member 1202 may also include a plurality of horizontal members, lateral members or straight members 1216 positioned between the first endplate 1152 and the second endplate 1162. Each horizontal member 1216 may be separated by a space 1218. The horizontal members 1216 may be coupled to each of the lateral connecting members 1212, 1214. In addition, each horizontal member 1216 may be positioned parallel with every other horizontal member 1216.

Figure 66:
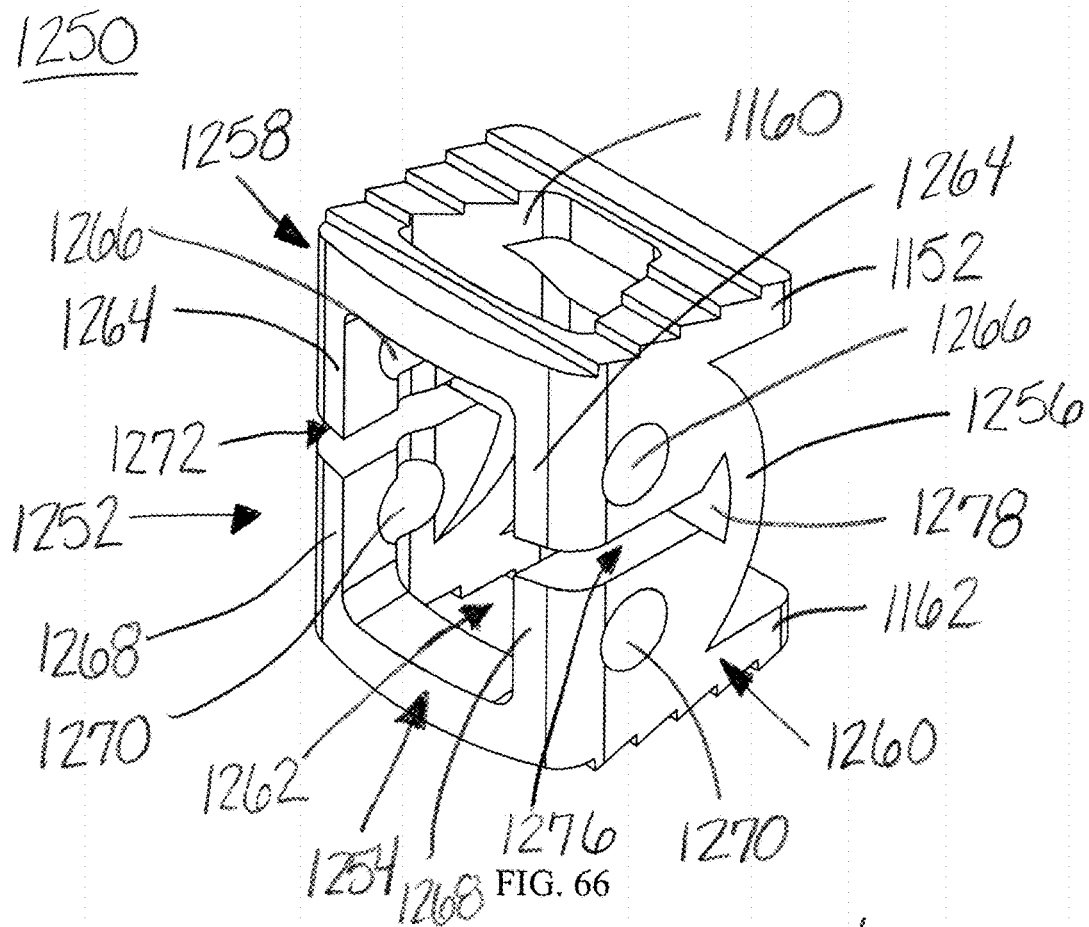
FIG. 66 is a first perspective view of another interbody spacer, in accordance with an aspect of the present disclosure.
Figure 67:
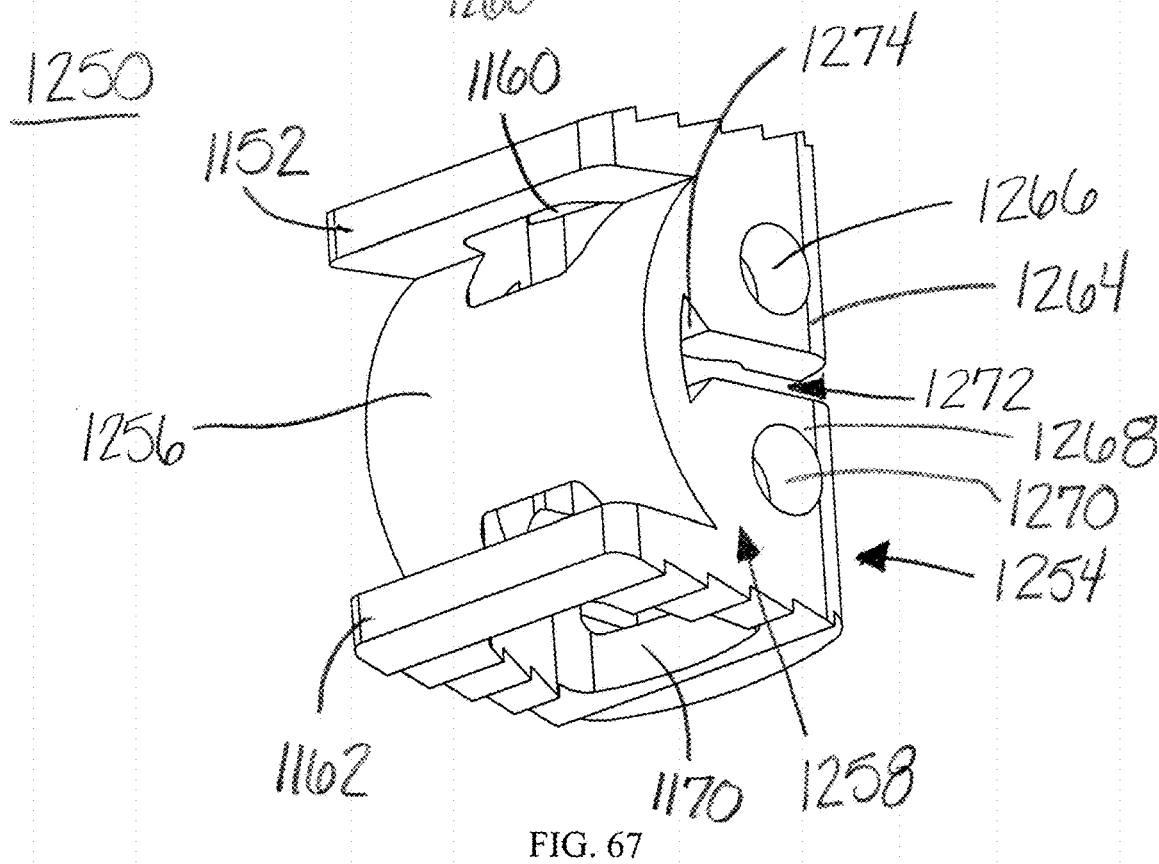
FIG. 67 is a second perspective view of the interbody spacer of FIG. 66, in accordance with an aspect of the present disclosure.
Figure 68:
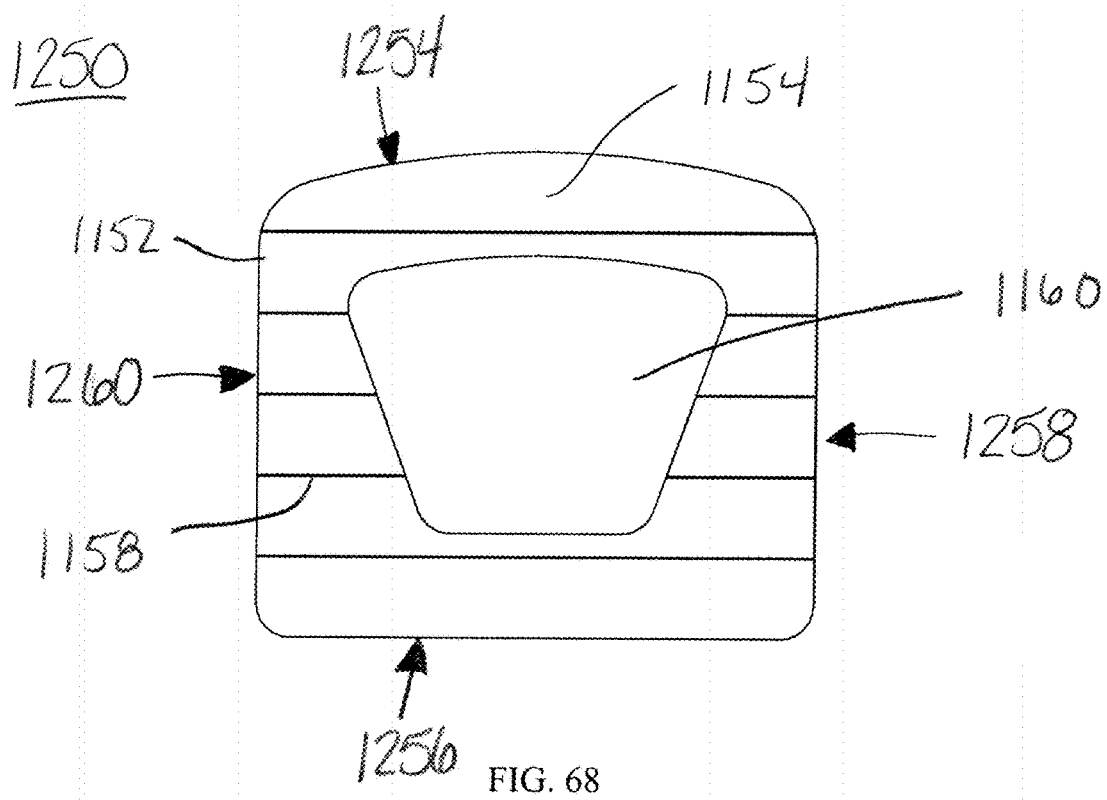
FIG. 68 is a top view of the interbody spacer of FIG. 66, in accordance with an aspect of the present disclosure.
Figure 69:
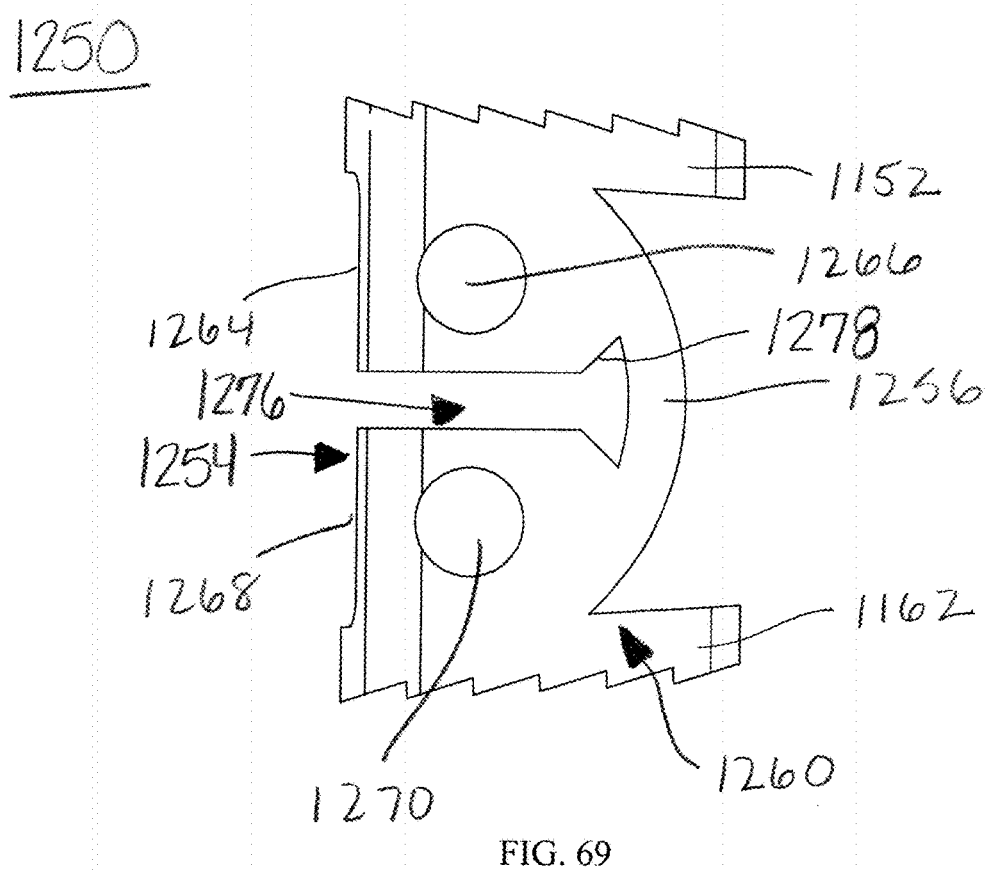
FIG. 69 is a first side view of the interbody spacer of FIG. 66, in accordance with an aspect of the present disclosure.
Figure 70:
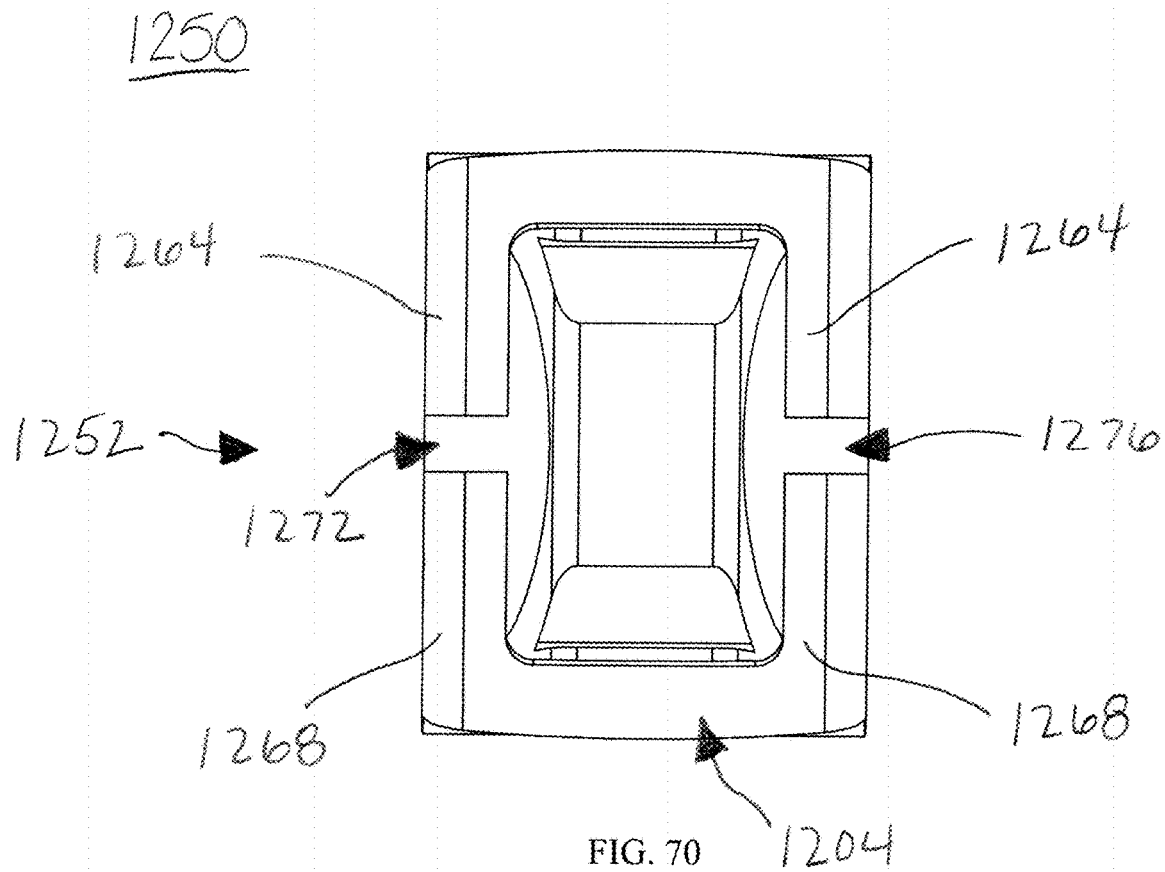
FIG. 70 is a first end view of the interbody spacer of FIG. 66, in accordance with an aspect of the present disclosure.
Figure 71:
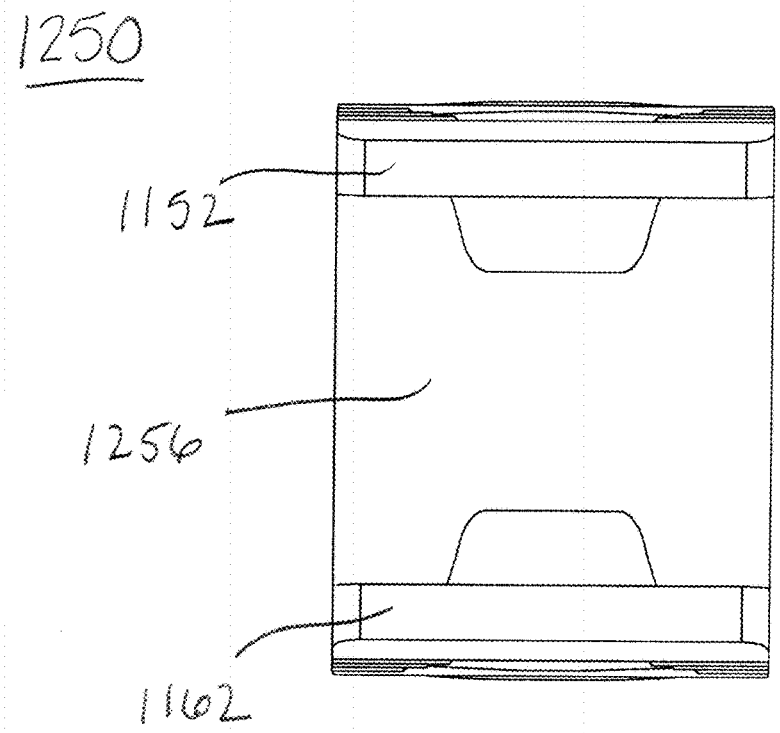
FIG. 71 is a second end view of the interbody spacer of FIG. 66, in accordance with an aspect of the present disclosure.
Figure 72:
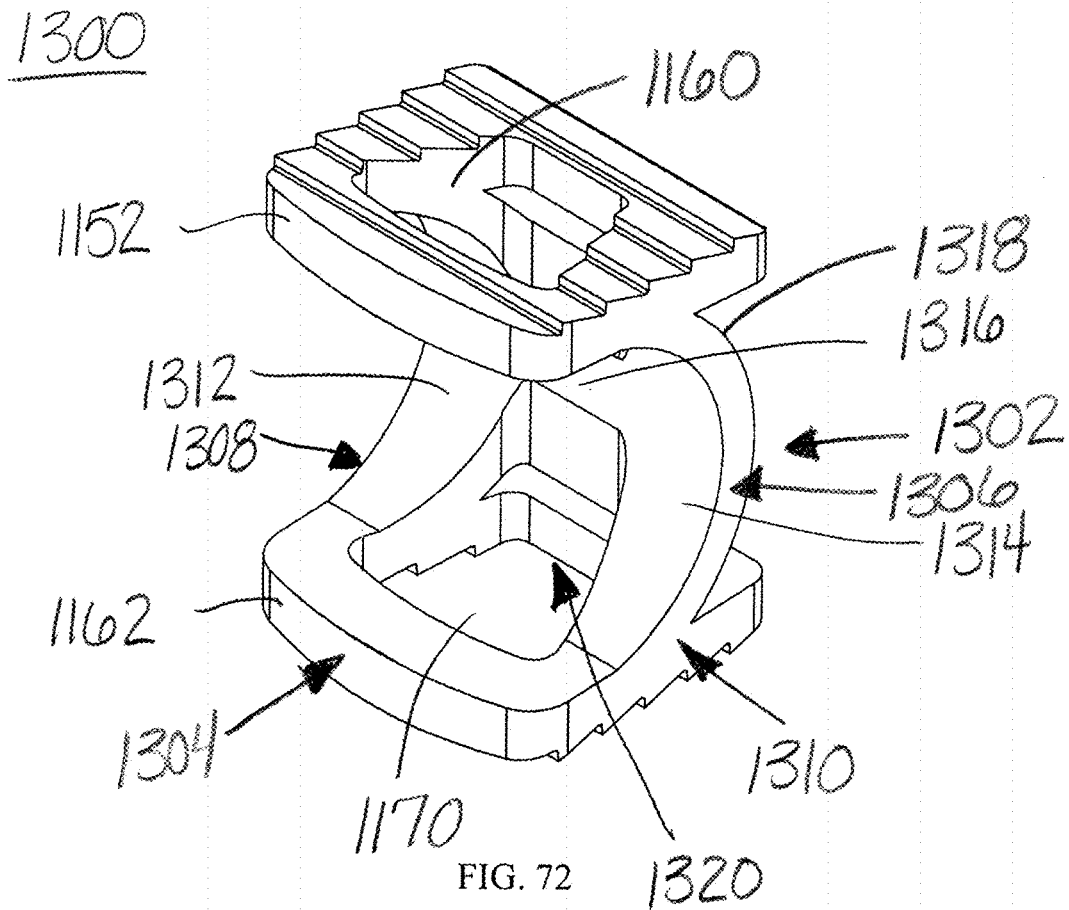
FIG. 72 is a first perspective view of another interbody spacer, in accordance with an aspect of the present disclosure.
Figure 73:
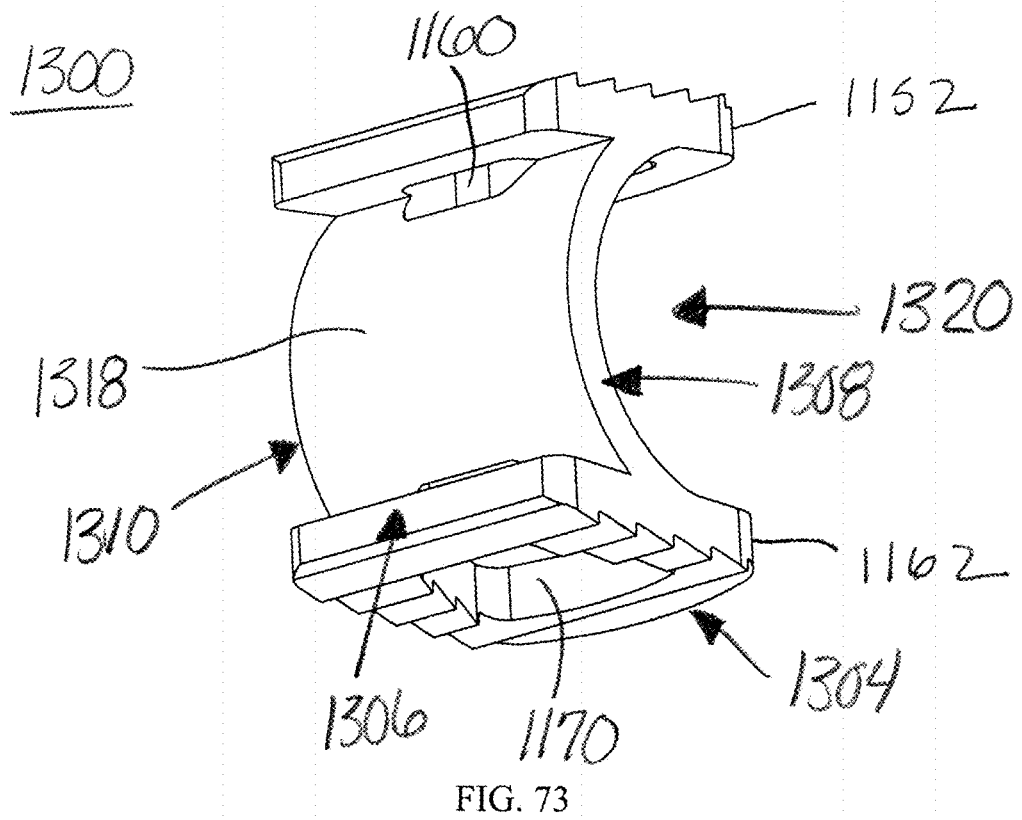
FIG. 73 is a second perspective view of the interbody spacer of FIG. 72, in accordance with an aspect of the present disclosure.
Figure 74:
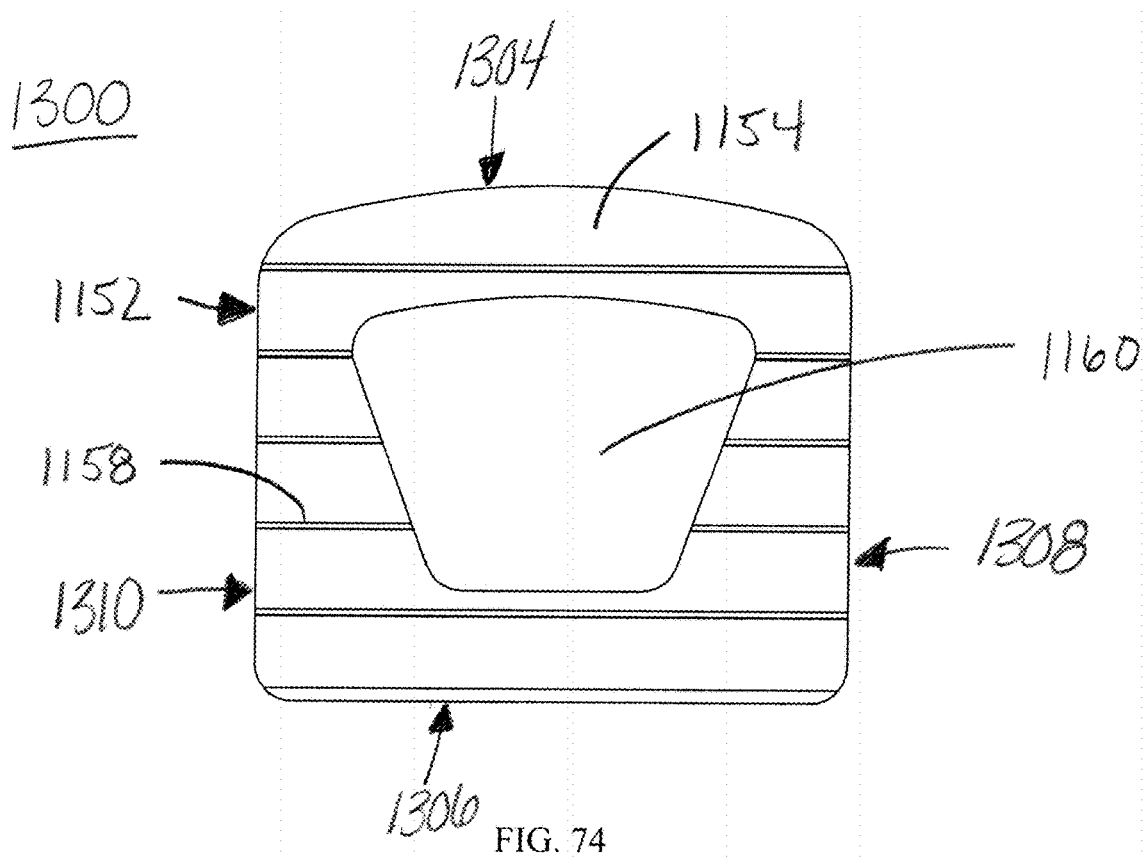
FIG. 74 is a top view of the interbody spacer of FIG. 72, in accordance with an aspect of the present disclosure.
Figure 75:
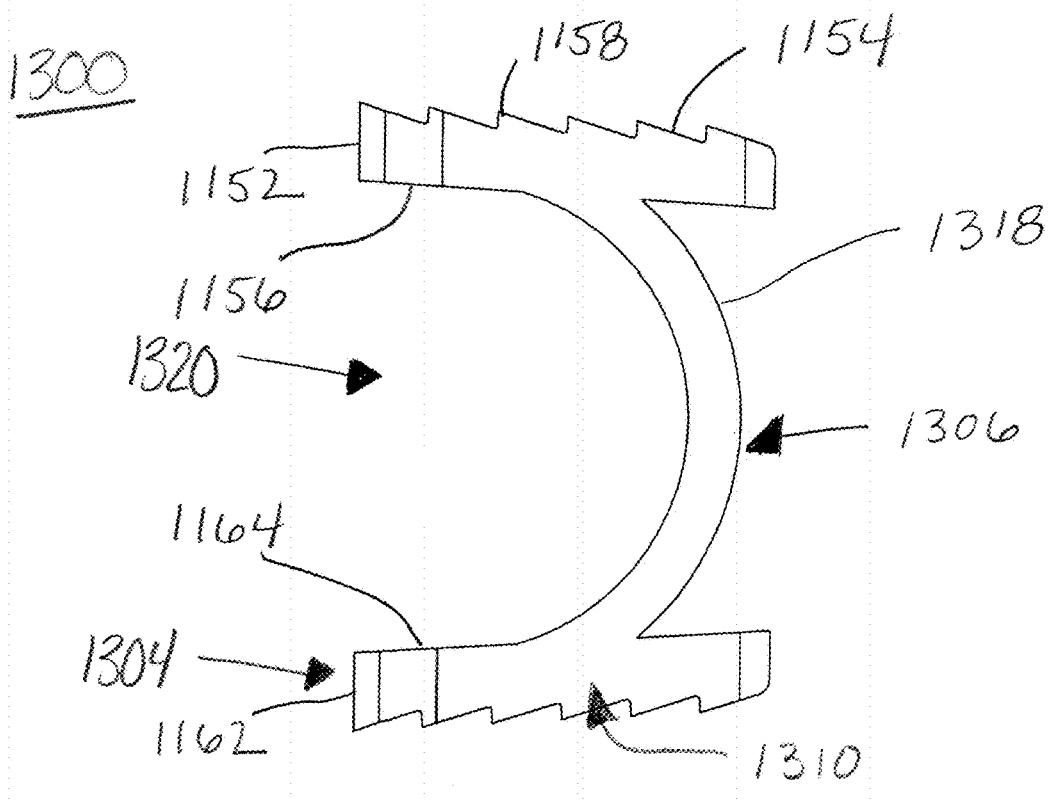
FIG. 75 is a first side view of the interbody spacer of FIG. 72, in accordance with an aspect of the present disclosure.
Figure 76:
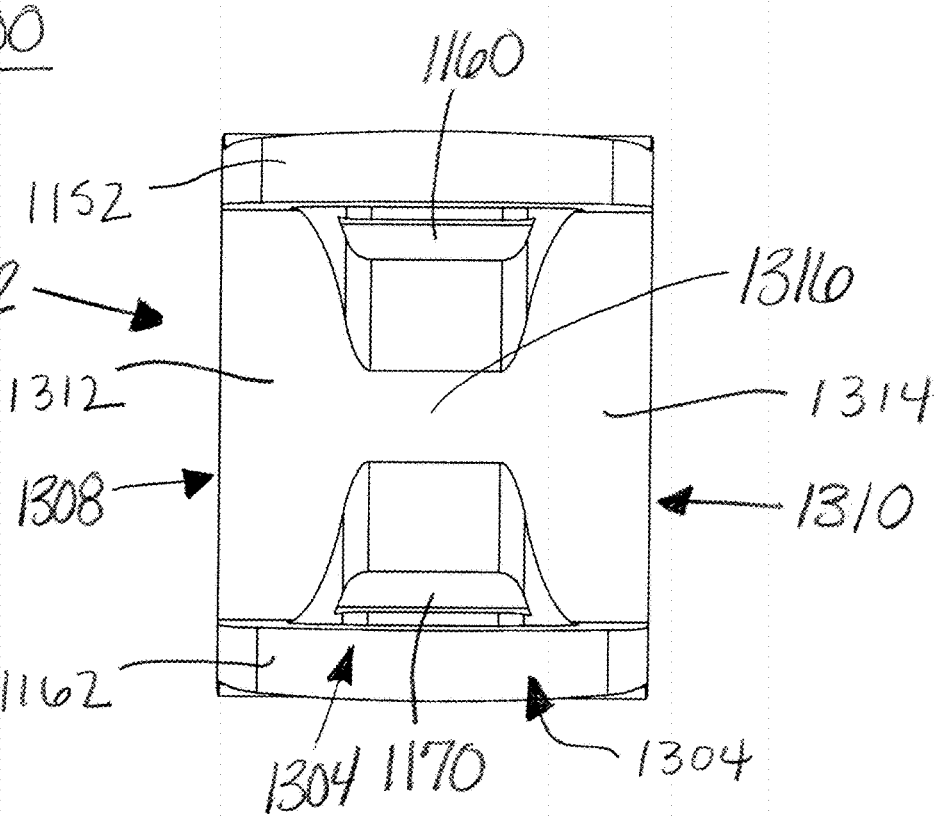
FIG. 76 is a first end view of the interbody spacer of FIG. 72, in accordance with an aspect of the present disclosure.

Referring now to FIGS. 66-71, an implant 1250 is shown. The implant 1250 may include a first or superior endplate 1152, a second or inferior endplate 1162, and a coupling member 1252 positioned between the first endplate 1152 and the second endplate 1162. The first endplate 1152 and the second endplate 1162 are as described above with reference to implant 1150 and will not be described again here for brevity sake. The coupling member 1252 may include a first or anterior side 1254 opposite a lateral connecting member 1256 and a first lateral side or third side 1258 opposite a second lateral side or fourth side 1260. The lateral sides 1258, 1260 may extend between the anterior side 1254 and the lateral connecting member 1256, as shown in FIGS. 66, 67 and 69. The coupling member 1252 may also include an opening or recess 1262 extending into the coupling member 1252 from the anterior side 1254 to the lateral connecting member 1256.

The coupling member 1252 may further include at least one first vertical member 1264 extending away from a bottom surface 1156 of the first endplate 1252 and into the opening 1262. The at least one first vertical member 1264 may be, for example, two first vertical members 1264, one positioned on the first lateral side 1258 and a second positioned on a second lateral side 1260. Each first vertical member 1264 may include a through hole 1266 extending through the first vertical member 1264 from an exterior surface of the implant 1250 and into the opening 1262. The coupling member 1252 may also include at least one second vertical member 1268 extending away from a top surface 1164 of the second endplate 1262 and into the opening 1262. The at least one second vertical member 1268 may be, for example, two second vertical members 1268, one positioned on the first lateral side 1258 and a second positioned on a second lateral side 1260. Each second vertical member 1268 may include a through hole 1270 extending through the second vertical member 1268 from an exterior surface of the implant 1250 and into the opening 1262.

With continued reference to FIGS. 66, 67, 69 and 70, the coupling member 1252 also includes a first channel 1272 extending into the implant 1250 from the anterior side 1254 to the lateral connecting member 1256. The first channel 1272 may be positioned between the first vertical member 1264 and the second vertical member 1268 on the first lateral side 1258 of the implant 1250. The first channel 1272 may terminate in a first cutout 1274 when the channel 1272 contacts the lateral connecting member 1256. The cutout 1274 may be, for example, triangularly shaped, although other shapes are contemplated which allow for deformation of the lateral connecting member 1256. In addition, the coupling member 1252 may include a second channel 1276 extending into the implant 1250 from the anterior side 1254 to the lateral connecting member 1256. The second channel 1276 may be positioned between the first vertical member 1264 and the second vertical member 1268 on the second lateral side 1260 of the implant 1250. The second channel 1276 may terminate in a second cutout 1278 when the channel 1278 contacts the lateral connecting member 1256. The cutout 1278 may be, for example, triangularly shaped, although other shapes are contemplated which allow for deformation of the lateral connecting member 1256.

FIGS. 72-77 show another implant 1300. The implant 1300 may include a first or superior endplate 1152, a second or inferior endplate 1162, and a connecting member 1302 coupling the superior endplate 1152 to the inferior endplate 1162. The first endplate 1152 and the second endplate 1162 are as described above with reference to implant 1150 and will not be described again here for brevity sake. The coupling member 1302 may include a first or anterior side 1304 opposite a lateral connecting member 1306 and a first lateral side or third side 1308 opposite a second lateral side or fourth side 1310. The coupling member 1302 may also include a recess 1320 extending into the coupling member 1302 from the anterior side to the lateral connecting member 1306.

As shown in FIGS. 72, 73, 75 and 76, the coupling member 1302 also includes a first lateral connecting member 1312 positioned on a first lateral side 1308 of the coupling member 1302 and a second lateral connecting member 1314 positioned on a second lateral side 1310 of the coupling member 1302. A first end of each lateral connecting member 1312, 1314 may be coupled to the first endplate 1152 and a second end of each lateral connecting member 1312, 1314 may be coupled to the second endplate 1162. The lateral connecting members 1312, 1314 may, for example, curve or arc as they extend between the first endplate 1152 and the second endplate 1154. The coupling member 1302 may also include a horizontal member, lateral member or straight member 1316 extending between the first lateral connecting member 1312 and the second lateral connecting member 1314 on the anterior side of the implant 1300. In addition, the coupling member 1302 may include a posterior surface 1318 forming a uniform surface between the first lateral side 1308 and the second lateral side 1310 as well as between the through hole 1160 and through hole 1170.

It is understood that the embodiments described herein may be used in the cervical, thoracic, or lumbar regions of the spine. It is also understood that these devices may be inserted through an anterior approach, such as during an ACDF or anterior lumbar interbody fusion (ALIF), or it may be inserted through other surgical approaches, such as lateral lumbar interbody fusion, posterior lumbar interbody fusion, transforaminal lumbar interbody fusion, etc. With the other surgical approaches, the implant may be oriented such that the open anterior portion of the cage is not aligned with the anterior portion of the patient.

Although the present disclosure focuses on use of the implants 100, 150, 200, 250, 300, 350, 400, 450, 500, 550, 600, 650, 700, 750, 800, 850, 900, 950, 1000, 1050, 1100, 1150, 1200, 1250, 1300 in a patient's spine, it is also contemplated that the implants 100, 150, 200, 250, 300, 350, 400, 450, 500, 550, 600, 650, 700, 750, 800, 850, 900, 950, 1000, 1050, 1100, 1150, 1200, 1250, 1300 may be used, for example, to connect any bone segments and/or to fill a bony defect that might result from trauma, tumor, infection, or another event. The bone segments may include bone segments of long bones, the ankle, and like bones, as would be known by one of ordinary skill in the art. When used with long bones and other non-vertebral bones the implants 100, 150, 200, 250, 300, 350, 400, 450, 500, 550, 600, 650, 700, 750, 800, 850, 900, 950, 1000, 1050, 1100, 1150, 1200, 1250, 1300 may be placed, for example, within the bone segments to assist with fusing the bone segments back together. The implant 100, 150, 200, 250, 300, 350, 400, 450, 500, 550, 600, 650, 700, 750, 800, 850, 900, 950, 1000, 1050, 1100, 1150, 1200, 1250, 1300 would be secured to each of the bone segments with or without bone graft material inserted within the implant. If additional support for the bone segments was needed a surgeon could also use, for example, bone plates or other external bone fixation devices for holding the bone segments in place while fusion occurs with the assistance of the implant 100, 150, 200, 250, 300, 350, 400, 450, 500, 550, 600, 650, 700, 750, 800, 850, 900, 950, 1000, 1050, 1100, 1150, 1200, 1250, 1300. Once the bone segments are sufficiently secured, the surgical procedure may be completed and the patient may be closed.

While the preferred and alternative embodiments described herein are made of a metallic material, it is understood that the same designs are achievable through use of alternative materials, for example, elastic, hyperelastic, or deformable polymers, ceramics, or composites. The figures and specification are meant to depict features present in alternative embodiments. It is understood that features depicted in certain embodiments may be used in conjunction with features depicted in other embodiments.

As may be recognized by those of ordinary skill in the art based on the teachings herein, numerous changes and modifications may be made to the above-described and other embodiments of the present disclosure without departing from the scope of the disclosure. The interbody spacers and other components of the interbody spacers and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the interbody spacers and systems may include more or fewer components or features than the embodiments as described and illustrated herein. For example, the components and features of FIGS. 1-8, FIGS. 9-10, FIGS. 11-13, FIGS. 14-20, FIGS. 21-24, FIGS. 25-27, FIG. 28, FIGS. 29-30, FIGS. 31-33, FIG. 34, FIGS. 35-37, FIG. 38, FIG. 39, FIG. 40, FIG. 41, FIG. 42, FIGS. 43-46, FIG. 47, FIG. 48, FIGS. 49-51, FIGS. 52-53, FIGS. 54-59, FIGS. 60-65, FIGS. 66-71, and FIGS. 72-77 may all be used interchangeably and in alternative combinations as would be modified or altered by one of skill in the art. Accordingly, this detailed description of the currently-preferred embodiments is to be taken as illustrative, as opposed to limiting the invention.

Moreover, approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value. When introducing elements of various embodiments, the articles "a," "an," "the," and "said" are intended to mean that there are one or more of the elements. The terms "comprising," "including," and "having" are intended to be inclusive and mean that there may be additional elements other than the listed elements. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. Any examples of operating parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. An interbody spacer, comprising:
at least one first endplate;
at least one second endplate; and
at least one connecting member coupled to and extending between the at least one first endplate and the at least one second endplate, wherein the connecting member comprises:
at least one arcuate member extending between the at least one first endplate and the at least one second endplate, and wherein the at least one arcuate member couples to the at least one first endplate and the at least one second endplate between a first side and a second side, wherein the at least one arcuate member comprises:
a first arcuate member coupled to and extending between a first side of the at least one first endplate and a first side of the at least one second endplate; and
a second arcuate member coupled to and extending between a second side of the at least one first endplate and a second side of the at least one second endplate; and
at least one reinforcement member connecting the first arcuate member and the second arcuate member.

2. The interbody spacer of claim 1, wherein a first end of the at least one arcuate member is coupled near a middle of the at least one first endplate and a second end of the at least one arcuate member is coupled near a middle of the at least one second endplate.

3. The interbody spacer of claim 1, wherein a first end of the at least one arcuate member is coupled near an anterior portion of the at least one first endplate and a second end of the at least one arcuate member is coupled near an anterior portion of the at least one second endplate.

4. The interbody spacer of claim 1, wherein the at least one reinforcement member is positioned on at least one of a posterior region of the interbody spacer and an anterior region of the interbody spacer.

5. The interbody spacer of claim 1, wherein the at least one connecting member extends between a first side of each of the at least one first endplate and the at least one second endplate and a second side of each of the at least one first endplate and at least one second endplate.

6. The interbody spacer of claim 5, wherein the at least one coupling member has a posterior surface forming a uniform surface between a first lateral side and a second lateral side of the interbody spacer.

7. The interbody spacer of claim 1, wherein at least one reinforcement member of the at least one connecting member extends between the first arcuate member and the second arcuate member.

8. The interbody spacer of claim 1, wherein the at least one first endplate comprises:
at least one aperture or through hole extending through the at least one first endplate.

9. The interbody spacer of claim 8, wherein the at least one second endplate comprises:
at least one aperture or through hole extending through the at least one second endplate.

10. An interbody spacer, comprising:
at least one first endplate;
at least one second endplate; and
at least one connecting member coupled to and extending between the at least one first endplate and the at least one second endplate, wherein the at least one connecting member comprises:
at least one arcuate member extending between the at least one first endplate and the at least one second endplate, and wherein the at least one arcuate member couples to the at least one first endplate and the at least one second endplate between a first side and a second side; and at least one coupling member connecting a first arcuate member of the at least one arcuate member and a second arcuate member of the at least one arcuate member.

11. The interbody spacer of claim 10, wherein the at least one coupling member is positioned on at least one of a posterior region of the interbody spacer and an anterior region of the interbody spacer.

12. The interbody spacer of claim 11, wherein the at least one coupling member is positioned on a posterior region of the interbody spacer and an anterior region of the interbody spacer.

13. The interbody spacer of claim 12, wherein the coupling member has a generally square or rectangular shape.

14. The interbody spacer of claim 10, wherein the at least one coupling member comprise:

a plurality of horizontal members, lateral members, or straight members extending between the first arcuate member and the second arcuate member.

15. The interbody spacer of claim 14, wherein each member of the plurality of horizontal members, lateral members, or straight members are separated by a space.

16. The interbody spacer of claim 14, wherein each member is positioned parallel to every other member.

17. A method for using an interbody spacer, comprising:
obtaining the interbody spacer; and
inserting the interbody spacer into a patient between two vertebral bodies, wherein at least one arcuate member of the interbody spacer couples to and extends from at least one of a middle and an anterior portion of an at least one first endplate and at least one of a middle and an anterior portion of an at least one second endplate toward a posterior portion of the interbody spacer.

18. The method of claim 17, further comprising:
inserting bone graft material into the interbody spacer after insertion of the interbody spacer into the patient.

19. The method of claim 17, wherein inserting the interbody spacer between two vertebral bodies positions a superior member of the interbody spacer to contact an inferior surface of a first vertebral body and an inferior member of the interbody spacer to contact a superior surface of a second vertebral body.

* * * * *